(12) United States Patent
Bhamidipati et al.

(10) Patent No.: US 8,163,902 B2
(45) Date of Patent: *Apr. 24, 2012

(54) PRODRUGS OF 2,4-PYRIMIDINEDIAMINE COMPOUNDS AND THEIR USES

(75) Inventors: Somasekhar Bhamidipati, Foster City, CA (US); Rajinder Singh, Belmont, CA (US); Thomas Sun, Fremont, CA (US); Esteban Masuda, Menlo Park, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 1163 days.

This patent is subject to a terminal disclaimer.

(21) Appl. No.: 11/943,506

(22) Filed: Nov. 20, 2007

(65) Prior Publication Data

US 2011/0144059 A1 Jun. 16, 2011

Related U.S. Application Data

(60) Provisional application No. 60/866,722, filed on Nov. 21, 2006.

(51) Int. Cl.
C07D 498/02 (2006.01)
A61K 31/535 (2006.01)
(52) U.S. Cl. .................................. 544/105; 514/230.5
(58) Field of Classification Search .................. 544/105
See application file for complete search history.

(56) References Cited

U.S. PATENT DOCUMENTS

| | | | |
|---|---|---|---|
| 7,060,827 B2 * | 6/2006 | Singh et al. ................ 544/323 |
| 7,122,542 B2 | 10/2006 | Singh et al. |
| 7,329,671 B2 | 2/2008 | Singh et al. |
| 7,329,672 B2 | 2/2008 | Singh et al. |
| 7,332,484 B2 | 2/2008 | Singh et al. |
| 2004/0029902 A1 | 2/2004 | Singh et al. |
| 2005/0209230 A1 | 9/2005 | Singh et al. |
| 2005/0234049 A1 | 10/2005 | Singh et al. |
| 2006/0058525 A1 | 3/2006 | Singh et al. |
| 2006/0135543 A1 | 6/2006 | Singh et al. |
| 2006/0167254 A1 | 7/2006 | Cooper et al. |
| 2006/0211657 A1 | 9/2006 | Singh et al. |
| 2006/0234983 A1 | 10/2006 | Singh et al. |
| 2006/0270694 A1 | 11/2006 | Wong |
| 2006/0293311 A1 | 12/2006 | Li et al. |
| 2007/0004626 A1 | 1/2007 | Masuda et al. |
| 2007/0060603 A1 | 3/2007 | Singh et al. |
| 2007/0117775 A1 | 5/2007 | Payan |
| 2007/0129360 A1 | 6/2007 | Bamidipati et al. |
| 2007/0129362 A1 | 6/2007 | Bhamidipati et al. |
| 2007/0167439 A1 | 7/2007 | Singh et al. |
| 2007/0197782 A1 | 8/2007 | Clough et al. |
| 2007/0203161 A1 | 8/2007 | Argade et al. |
| 2007/0203162 A1 | 8/2007 | Li et al. |
| 2007/0225321 A1 | 9/2007 | Singh et al. |
| 2007/0225495 A1 | 9/2007 | Singh et al. |
| 2007/0293520 A1 | 12/2007 | Singh et al. |
| 2007/0293521 A1 | 12/2007 | Singh et al. |
| 2007/0293522 A1 | 12/2007 | Singh et al. |
| 2007/0293523 A1 | 12/2007 | Singh et al. |
| 2007/0293524 A1 | 12/2007 | Singh et al. |
| 2007/0299095 A1 | 12/2007 | Singh et al. |
| 2008/0039622 A1 | 2/2008 | Singh et al. |
| 2008/0194603 A1 | 8/2008 | Li et al. |
| 2008/0221089 A1 | 9/2008 | Argade et al. |
| 2008/0260754 A1 | 10/2008 | Li et al. |
| 2008/0279867 A1 | 11/2008 | Atuegbu et al. |

FOREIGN PATENT DOCUMENTS

WO WO 2006/078846 7/2006

OTHER PUBLICATIONS

Braselmann et al Journal of Pharmacology and Experimental Therapeutics, 319(3)998-1008 (2006).*
U.S. Appl. No. 11/539,142, filed Oct. 5, 2006, Singh et al.
U.S. Appl. No. 11/539,074, filed Oct. 5, 2006, Singh et al.
U.S. Appl. No. 12/028,581, filed Feb. 8, 2008, Argade et al.
U.S. Appl. No. 12/030,031, filed Feb. 12, 2008, Li et al.
U.S. Appl. No. 12/175,441, filed Jul. 17, 2008, Singh et al.
U.S. Appl. No. 12/193,627, filed Aug. 18, 2008, Li et al.
U.S. Appl. No. 12/199,705, filed Aug. 27, 2008, Singh et al.
U.S. Appl. No. 12/268,235, filed Nov. 10, 2008, Singh et al.
U.S. Appl. No. 12/268,218, filed Nov. 10, 2008, Singh et al.
U.S. Appl. No. 12/273,357, filed Nov. 18, 2008, Singh et al.

* cited by examiner

*Primary Examiner* — Brandon Fetterolf
*Assistant Examiner* — Shirley V Gembeh
(74) *Attorney, Agent, or Firm* — Travis Young; McDonnell Boehnen Hulbert & Berghoff LLP

(57) ABSTRACT

The present disclosure provides prodrugs of biologically active 2,4-pyrimidinediamine compounds, salts and hydrates of the prodrugs, compositions comprising the prodrugs, intermediates and methods for synthesizing the prodrugs and methods of using the prodrugs in a variety of applications.

22 Claims, 16 Drawing Sheets

Rat PK Profiles for Prodrug Compound 4

FIG. 5

PK Summary

| Mode of Delivery | Analyte | Parameter | Value | Comments |
|---|---|---|---|---|
| IV | Prodrug 4 | Clearance, ml/min/kg | 93.1 | AUC of 4 = 182<br>AUC of 1 = 327 |
| | | T1/2, hr | 0.2 | |
| PO | Drug 1 | %F | 29.9 | Total absorbed and converted to Drug 1 |
| | | Cmax, ng/ml | 331 | |
| | Prodrug 4 | %F | 0.3 | |
| | | Cmax, ng/ml | 5.23 | |

Comparison of Drug Exposure – Prodrug 4 vs Drug 1 in PEG-400 cLogD vs pH (Pallas) and Measured Solubility

Chemical Stability of Prodrug 4

Plasma Stability (Rat) of Prodrug 4 and PNP

US 8,163,902 B2

PRODRUGS OF 2,4-PYRIMIDINEDIAMINE COMPOUNDS AND THEIR USES

CROSS-REFERENCE TO RELATED APPLICATIONS

This application claims benefit of U.S. provisional application Ser. No. 60/866,722, filed 21 Nov. 2006, which is incorporated herein by reference.

BACKGROUND OF THE INVENTION

1. Field of the Invention

The present disclosure relates to prodrugs of biologically active 2,4-pyrimidinediamine compounds, pharmaceutical compositions comprising the prodrugs, intermediates and synthetic methods of making the prodrugs and methods of using the prodrugs and compositions in a variety of contexts, such as in the treatment or prevention of various diseases.

2. Description of the Related Art

Crosslinking of Fc receptors, such as the high affinity receptor for IgE (FcεRI) and/or the high affinity receptor for IgG (FcγRI) activates a signaling cascade in mast, basophil and other immune cells that results in the release of chemical mediators responsible for numerous adverse events. For example, such crosslinking leads to the release of preformed mediators of Type I (immediate) anaphylactic hypersensitivity reactions, such as histamine, from storage sites in granules via degranulation. It also leads to the synthesis and release of other mediators, including leukotrienes, prostaglandins and platelet-activating factors (PAFs), that play important roles in inflammatory reactions. Additional mediators that are synthesized and released upon crosslinking Fc receptors include cytokines and nitric oxide.

The signaling cascade(s) activated by crosslinking Fc receptors such as FcεRI and/or FcγRI comprises an array of cellular proteins. Among the most important intracellular signal propagators are the tyrosine kinases. And, an important tyrosine kinase involved in the signal transduction pathways associated with crosslinking the FcεRI and/or FcγRI receptors, as well as other signal transduction cascades, is Syk kinase (see Valent et al., 2002, Intl. J. Hematol. 75(4):257-362 for review).

The mediators released as a result of FcεRI and FcγRI receptor cross-linking are responsible for, or play important roles in, the manifestation of numerous adverse events. Recently, various classes of 2,4-pyrimidinediamine compounds have been discovered that inhibit the FcεRI and/or FcγRI signaling cascades, and that have myriad therapeutic uses. See, e.g., U.S. application Ser. No. 10/355,543 filed Jan. 31, 2003 (US 2004/0029902), international application Serial No. PCT/US03/03022 filed Jan. 31, 2003 (WO 03/063794), U.S. application Ser. No. 10/631,029 filed Jul. 29, 2003 (US 2005/0028212), international application Serial No. PCT/US03/24087 (WO 2004/014382), U.S. application Ser. No. 10/903,263 filed Jul. 30, 2004 (US2005/0234049), and international application Serial No. PCT/US2004/24716 (WO 2005/016893). While many of these compounds exhibit good bioavailability properties, in some instances it may be desirable to tailor their solubility or other properties such that their bioavailability via specified routes of administration is optimized.

SUMMARY OF THE INVENTION

The present disclosure provides prodrugs of 2,4-pyrimidinediamine compounds that have myriad biological activities, and hence therapeutic uses, compositions comprising the prodrugs, methods and intermediates useful for synthesizing the prodrugs and methods of using the prodrugs in a variety of in vitro and in vivo contexts, including in the treatment and/or prevention of diseases mediated, at least in part, by the activation of Fc receptor signaling cascades.

The prodrugs generally comprise a biologically active 2,4-pyrimidinediamine compound that is substituted at the nitrogen atom of one or more primary or secondary amine groups with a progroup $R^p$ that metabolizes or otherwise transforms under conditions of use to yield the active 2,4-pyrimidinediamine. In some embodiments, the progroup $R^p$ is a phosphorous-containing progroup. In some embodiments, the progroup includes a group or moiety that is metabolized under the conditions of use to yield an unstable α-hydroxymethyl, α-aminomethyl or α-thiomethyl intermediate, which then further metabolized in vivo to yield the active 2,4-pyrimidinediamine drug. In some embodiments, the progroup includes an α-hydroxyalkyl, α-aminoalkyl or α-thioalkyl moiety, for example an α-hydroxymethyl, α-aminomethyl, α-thiomethyl moiety, that metabolizes under the conditions of use to yield the active 2,4 pyrimidinediamine drug. For example, in some embodiments the progroup $R^p$ is of the formula —$CR^dR^d$-$AR^3$, where each $R^d$ is, independently of the other, selected from hydrogen, cyano, optionally substituted (C1-C20) alkyl, (C1-C20) perfluoroalkyl, optionally substituted (C7-C30) arylalkyl and optionally substituted 6-30 membered heteroarylalkyl, where each optional substituent is, independently of the others, selected from hydrogen, alkyl, aryl, arylalkyl, heteroaryl and heteroalkyl, or, alternatively, the two $R^d$ are taken together with the carbon atom to which they are bonded to form a cycloalkyl containing from 3 to 8 carbon atoms; A is selected from O, S and $NR^{50}$, where $R^{50}$ is selected from hydrogen, alkyl, aryl, arylalkyl, heteroaryl, heteroarylalkyl and cycloheteroalkyl, or alternatively is combined with $R^3$, and, together with the nitrogen to which they are attached, form a three to seven membered ring; and $R^3$ represents a group that can be metabolized in vivo to yield a group of the formula —$CR^dR^d$-AH, where $R^d$ and A are as previously defined.

The identity of $R^3$ is not critical, provided that it can be metabolized under the desired conditions of use, for example under the acidic conditions found in the stomach and/or by enzymes found in vivo, to yield a group of the formula —$CR^dR^d$-AH, where A and $R^d$ are as previously defined. Thus, skilled artisans will appreciate that $R^3$ can comprise virtually any known or later-discovered hydroxyl, amine or thiol protecting group. Non-limiting examples of suitable protecting groups can be found, for example, in Protective Groups in Organic Synthesis, Greene & Wuts, 2nd Ed., John Wiley & Sons, New York, 1991 (especially pages 10-142 (alcohols), 277-308 (thiols) and 309-405 (amines) the disclosure of which is incorporated herein by reference).

In a specific embodiment, $R^3$ includes, together with A, an ether, a thioether, a silyl ether, a silyl thioether, an ester, a thioester, an amide, a carbonate, a thiocarbonate, a carbamate, a thiocarbamate, or a urea linkage, —$OCH_2SO_3R$, where R is hydrogen, alkyl, aryl, arylalkyl or a metal salt (e.g., sodium, lithium, potassium); -$GCH_2{}^+N(R^{51})_3M^-$, where G is absent, —$OPO_3$—, $OSO_3$— or —$CO_2$—, $R^{51}$ is hydrogen, alkyl, aryl, arylalkyl, cycloheteroalkyl or cycloheteroalkylalkyl and M– is a counterion, usually a halide ion or the like (acetate, sulfate, phosphate, etc.). Specific exemplary embodiments include, but are not limited to, progroups $R^p$ in which $R^3$ is selected from $R^f$, —C(O)$R^f$, —C(O)O$R^f$, —C(O)N$R^fR^f$ and —Si$R^fR^fR^f$, where each $R^f$ is, independently of the others, selected from hydrogen, optionally substituted lower alkyl, optionally substituted lower heteroalkyl, optionally substituted lower cycloalkyl, optionally substituted lower heterocycloalkyl, optionally substituted (C6-C10) aryl, optionally substituted 5-10 membered heteroaryl, optionally substituted (C7-C18) arylalkyl and optionally substituted 6-18 membered heteroarylalkyl. In a specific embodiment, each $R^f$ is the same.

The identity of the progroup(s) $R^p$ can be selected to tailor the water-solubility and other properties of the underlying active 2,4-pyrimidinediamine compound to be optimized for a particular mode of administration. It can also be selected to provide for removal at specified organs and/or tissues within the body, such as, for example, in the digestive tract, in blood and/or serum, or via enzymes residing in specific organs, such as the liver.

In some embodiments, progroups $R^p$ that are phosphorous-containing progroups include phosphate moieties that can be cleaved in vitro by enzymes such as esterases, lipases and/or phosphatases. Such enzymes are prevalent throughout the body, residing in, for example, the stomach and digestive tract, blood and/or serum, and in virtually all tissues and organs. Such phosphate-containing progroups $R^p$ will generally increase the water-solubility of the underlying active 2,4-pyrimidinediamine compound, making such phosphate-containing prodrugs ideally suited for modes of administration where water-solubility is desirable, such as, for example, oral, buccal, intravenous, intramuscular and ocular modes of administration.

In some embodiments, each phosphate-containing progroup $R^p$ in the prodrug is of the formula —$(CR^dR^d)_y$—O—P(O)(OH)(OH), or a salt thereof, wherein $R^d$ is as previously defined and y is an integer ranging from 1 to 3, typically 1 or 2. In one specific embodiment, each $R^d$ is, independently of the others, selected from hydrogen, substituted or unsubstituted lower alkyl, substituted or unsubstituted phenyl, substituted or unsubstituted methyl and substituted or unsubstituted benzyl. In another specific embodiment, each $R^d$ is, independently of the others, selected from hydrogen and unsubstituted lower alkyl. Specific exemplary phosphate-containing progroups $R^p$ include —$CH_2$—O—P(O)(OH)(OH) and —$CH_2CH_2$—O—P(O)(OH)(OH) and/or the corresponding salts.

While not intending to be bound by any theory of operation, when y is 1 in the exemplary phosphate-containing progroups $R^p$, it is believed that the phosphate-containing prodrugs are converted in vivo by enzymes such as phosphatases, lipases and/or esterases to the corresponding hydroxymethylamines, which are then further metabolized in vivo by the elimination of formaldehyde to yield the active 2,4-pyrimidinediamine drug compound. The phosphate and formaldehyde metabolic by-products are innocuous.

When y is 2 in the exemplary phosphate-containing prodrugs, it is believed that the prodrugs are metabolized to the active 2,4-pyrimidinediamine drug compound in vivo by elimination of enol phosphate, which further metabolizes to acetaldehyde and phosphate. The phosphate and acetaldehyde metabolic by-products are innocuous.

Skilled artisans will appreciate that certain types of precursors can be converted in vivo to phosphate groups. Such precursors include, by way of example and not limitation, phosphate esters, phosphites and phosphite esters. For example, phosphites can be oxidized in vivo to phosphates. Phosphate esters can be hydrolyzed in vivo to phosphates. Phosphite esters can be oxidized in vivo to phosphate esters, which can in turn be hydrolyzed in vivo to phosphates. As a consequence of the ability of these phosphate precursor groups to convert to phosphates in vivo, the prodrugs can also include progroups that comprise such phosphate precursors. In some embodiments, the phosphate precursor groups may be directly metabolized to the active 2,4-pyrimidinediamine drug, without first being converted into a phosphate prodrug. In other embodiments, prodrugs comprising progroups that include such phosphate precursors are first metabolized into the corresponding phosphate prodrug, which then metabolizes to the active 2,4-pyrimidinediamine drug via a hydroxymethylamine, as discussed above. In some embodiments, such phosphate precursor groups are phosphate esters. The phosphate esters can be acyclic or cyclic, and can be phosphate triesters or phosphate diesters. Such esters are generally less water-soluble than the corresponding phosphate acid prodrugs and the corresponding active 2,4-pyrimidinediamine compounds, and are therefore typically suitable for modes of delivering prodrugs of active 2,4-pyrimidinediamine compounds where low water-solubility is desired, including, by way of example and not limitation, administration via inhalation. The solubility of the prodrug can be specifically tailored for specific modes of administration by appropriate selection of the number and identity(ies) of the esterifying groups in the phosphate ester.

The mechanism by which the phosphate ester group metabolizes to the corresponding phosphate group can be controlled by appropriate selection of the esterifying moieties. For example, it is well-known that certain esters are acid (or base) labile, generating the corresponding phosphate under the acidic conditions found in the stomach and digestive tract. In instances where it is desirable for the phosphate ester prodrug to metabolize to the corresponding phosphate prodrug in the digestive tract (such as, for example, where the prodrugs are administered orally), phosphate ester progroups that are acid-labile can be selected. Other types of phosphate esters are acid and base stable, being converted into the corresponding phosphates via enzymes found in certain tissues and organs of the body (see, e.g., the various cyclic phosphate esters described in Erion et al., 2004, J. Am. Chem. Soc. 126:5154-5163, incorporated herein by reference). In instances where it is desirable to convert a phosphate ester prodrug into the corresponding phosphate prodrug within a desired target tissue or site within the body, phosphate esters having the desired metabolic properties can be selected.

In some embodiments, each phosphate ester-containing progroup $R^p$ in the prodrug is an acyclic phosphate ester of the formula —$(CR^dR^d)_y$—O—P(O)(OH)($OR^e$) or —$(CR^d$-$R^d)_y$—O—P(O)($OR^e$)($OR^e$), or a salt thereof, wherein each $R^e$ is, independently of the others, selected from substituted or unsubstituted lower alkyl, substituted or unsubstituted (C6-C14) aryl (e.g., phenyl, naphthyl, 4-loweralkoxyphenyl, 4-methoxyphenyl), substituted or unsubstituted (C7-C20) arylalkyl (e.g., benzyl, 1-phenylethan-1-yl, 2-phenylethan-1-yl), —$(CR^dR^d)_y$—$OR^f$, —$(CR^dR^d)_y$—O—C(O)$R^f$, —$(CR^dR^d)_y$—O—C(O)$OR^f$, —$(CR^dR^d)_y$—S—C(O)$R^f$, —$(CR^dR^d)_y$—S—C(O)$OR^f$, —$(CR^dR^d)_y$—NH—C(O)$R^f$, —$(CR^dR^d)_y$—NH—C(O)$OR^f$ and —Si($R^d$)$_3$, wherein $R^d$, $R^f$ and y are as defined above. In a specific embodiment, each $R^d$ is selected from hydrogen and unsubstituted lower alkyl and/or each $R^e$ is an unsubstituted lower alkanyl or benzyl. Specific exemplary phosphate ester progroups include, but are not limited to, —$CH_2$—O—P(O)(OH)($OR^e$), —$CH_2CH_2$—O—P(O)(OH)($OR^e$), —$CH_2$—O—P(O)($OR^e$)($OR^e$) and —$CH_2CH_2$—O—P(O)($OR^e$)($OR^e$), where $R^e$ is selected from lower alkanyl, i-propyl and t-butyl.

In other embodiments, each phosphate ester-containing progroup $R^p$ is a cyclic phosphate ester of the formula

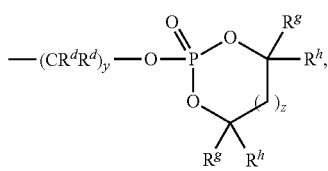

where each $R^g$ is, independently of the others, selected from hydrogen and lower alkyl; each $R^h$ is, independently of the others, selected from hydrogen, substituted or unsubstituted lower alkyl, substituted or unsubstituted lower cycloheteroalkyl, substituted or unsubstituted (C6-C14) aryl, substituted or unsubstituted (C7-C20) arylalkyl and substituted or unsubstituted 5-14 membered heteroaryl; z is an integer ranging from 0 to 2; and $R^d$ and y are as previously defined. In a specific embodiment, each phosphate ester-containing progroup $R^p$ is a cyclic phosphate ester of the formula

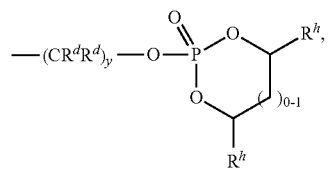

where $R^d$, $R^h$ and y are as previously defined.

The mechanism by which cyclic phosphate ester prodrugs including such cyclic phosphate ester progroups metabolize in vivo to the active drug compound depends, in part, on the identity of the $R^h$ substituent. For example, cyclic phosphate ester progroups in which each $R^h$ is, independently of the others, selected from hydrogen and lower alkyl are cleaved in vivo by esterases. Thus, in some embodiments, the cyclic phosphate ester progroups are selected such that they are cleavable in vivo by esterases. Specific examples of such cyclic phosphate ester progroups include, but are not limited to, progroups selected from

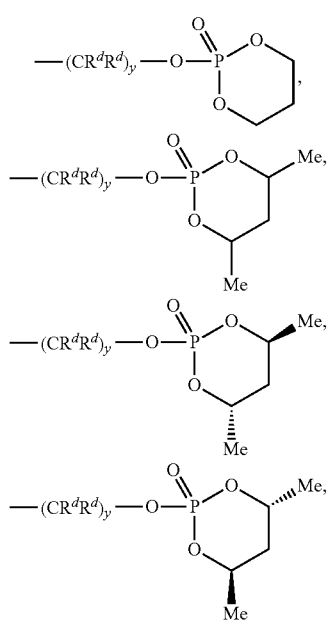

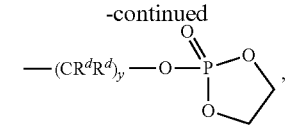

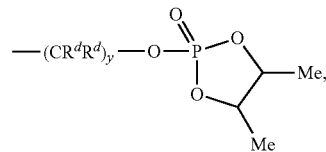

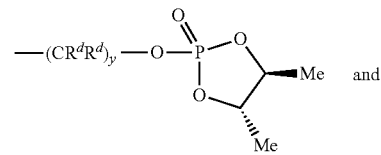

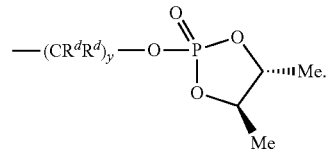

Alternatively, cyclic phosphate ester prodrugs having progroups in which the $R^h$ substituents are substituted or unsubstituted aryl, arylalkyl and heteroaryl groups, are not typically cleaved by esterases, but are instead metabolized to the active prodrug by enzymes, such as cytochrome $P_{450}$ enzymes, that reside in the liver. For example, a series of cyclic phosphate ester nucleotide prodrugs that undergo an oxidative cleavage reaction catalyzed by a cytochrome $P_{450}$ enzyme (CYP) expressed predominantly in the liver are described in Erion et al., 2004, J. Am. Chem. Soc. 126:5154-5163. In some embodiments, the cyclic phosphate ester progroups are selected such that they are cleavable by CYP enzymes expressed in the liver. Specific exemplary embodiments of such cyclic phosphate ester-containing progroups $R^p$ include, but are not limited to, progroups having the formula

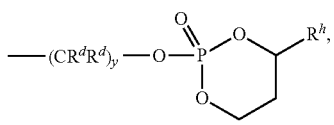

where $R^h$ is selected from phenyl, 3-chlorophenyl, 4-pyridyl and 4-methoxyphenyl.

As skilled artisans will appreciate, phosphites and phosphite esters can undergo oxidation in vivo to yield the corresponding phosphate and phosphate ester analogs. Such reactions can be carried out in vivo by, for example, oxidase enzymes, oxoreductase enzymes and other oxidative enzymes. Thus, the phosphorous-containing progroups $R^p$ can also include phosphite and phosphite ester analogs of any of the phosphate and phosphate ester progroups described above. In some embodiments the phosphorous-containing progroups $R^p$ include, but are not limited to, groups of the formula —$(CR^dR^d)_y$—O—P(OH)(OH), —$(CR^dR^d)_y$—O—P(OH)(OR$^e$) and —$(CR^dR^d)_y$—O—P(OR$^e$)(R$^e$), or salts thereof, where $R^d$, $R^e$ and y are as previously defined. Specific exemplary embodiments include groups in which each $R^d$ is, independently of the others, selected from hydrogen and unsubstituted lower alkyl and/or each $R^e$ is, independently of the others, selected from unsubstituted lower alkanyl and benzyl. Specific exemplary acyclic phosphite and phosphite-ester progroups include, but are not limited to, —CH$_2$—O—P(OH)(OH), —CH$_2$CH$_2$—O—P(OH)(OH), —CH$_2$—O—P(OH)(OR$^e$), and —CH$_2$CH$_2$—O—P(OR$^e$)(OR$^e$), where each $R^e$ is selected from lower alkanyl, i-propyl and t-butyl. Specific exemplary cyclic phosphite ester prodrugs include phosphite analogs of the above-described cyclic phosphate ester progroups. Conceptually, prodrug compounds including such phosphite and/or phosphite ester progroups can be thought of as prodrugs of the corresponding phosphate and phosphate ester prodrugs.

As mentioned above, it is believed that certain phosphate-containing prodrugs metabolize in vivo through the corresponding hydroxymethylamines. Although these hydroxymethylamines metabolize in vivo to the corresponding active 2,4-pyrimidinediamine compounds, they are stable at pH 7 and can be prepared and administered as hydroxyalkyl-containing prodrugs. In some embodiments, each hydroxyalkyl-containing progroup $R^p$ of such prodrugs is of the formula —CR$^d$R$^d$—OH, where $R^d$ is as previously defined. A specific exemplary hydroxyalkyl-containing progroup $R^p$ is —CH$_2$OH.

Virtually any known 2,4-pyrimidinediamine compound that has biological, and hence therapeutic, activity can be protected at an available primary or secondary amine with one or more progroups $R^p$ as described herein. Suitable active 2,4-pyrimidinediamine compounds are described, for example, in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003 (US 2005/0028212), international application Serial No. PCT/US03/24087 (WO2004/014382), U.S. application Ser. No. 10/903,263 filed Jul. 30, 2004 (US2005/0234049), and international application Serial No. PCT/US2004/24716 (WO 2005/016893), the disclosures of which are incorporated herein by reference. In such 2,4-pyrimidinediamine compounds, the progroup(s) $R^p$ can be attached to any available primary or secondary amine, including, for example, the N2 nitrogen atom of the 2,4-pyrimidinediamine moiety, the N4 nitrogen atom of the 2,4-pyrimidinediamine moiety, and/or a primary or secondary nitrogen atom included in a substituent on the 2,4-pyrimidinediamine compound. The use of phosphate-containing progroups $R^p$ is especially useful for 2,4-pyrimidinediamine compounds that exhibit poor water solubility under physiological conditions (for example, solubilities of less than about 10 μg/ml). While not intending to be bound by any theory of operation, it is believed that the phosphate-containing progroups aid the solubility of the underlying active 2,4-pyrimidinediamine compound, which in turn increases its bioavailability when administered orally. It is believed that the phosphate progroups $R^p$ are metabolized by phosphatase enzymes found in the digestive tract, permitting uptake of the underlying active drug.

It has been discovered that the water solubility and oral bioavailability of a particular biologically active 2,4-pyrimidinediamine compound, illustrated below (Compound 1), increased dramatically when formulated to include a progroup $R^p$ of the formula —CH$_2$—O—P(O)(OH)$_2$ at the ring nitrogen atom highlighted with the asterisk (Compound 4):

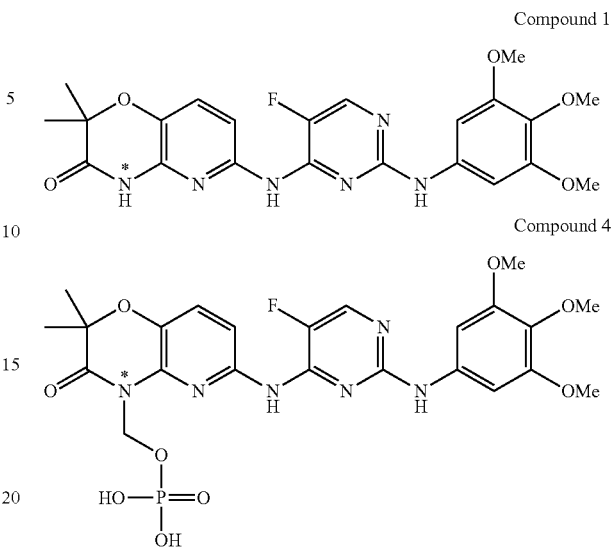

Significantly, whereas the water solubility of the active drug (Compound 1) is in the range of about <1 μg/ml in aqueous buffer under physiological conditions, the solubility of the corresponding phosphate prodrug (Compound 4) is greater than 5 mg/ml under the same conditions, or approximately 2000 times greater. This increased water-solubility allows for better dissolution in the gut, thereby facilitating oral administration. Other active 2,4-pyrimidinediamine compounds having similarly poor water solubilities are expected to exhibit similar increases in water solubility and oral bioavailability when formulated as phosphate prodrugs.

As mentioned above, phosphate ester prodrugs are generally less water-soluble than the corresponding phosphate prodrugs, and are therefore generally useful in applications where low water-solubility is desired, such as, for example, administration via inhalation. The same holds true for the relative water-solubility of phosphite ester and phosphite prodrugs.

In some embodiments, the prodrugs described herein are 2,4-pyrimidinediamine compounds that are substituted at the N4 nitrogen of the 2,4-pyrimidinediamine moiety with a substituted or unsubstituted nitrogen-containing bicyclic ring that includes at least one progroup $R^p$ as described herein at one or more of: the nitrogen atom(s) of the bicyclic ring, the N2 nitrogen of the 2,4-pyrimidinediamine moiety and/or the N4 nitrogen of the 2,4-pyrimidinediamine moiety. In a specific illustrative exemplary embodiment, the prodrug is a compound according to structural formula (I):

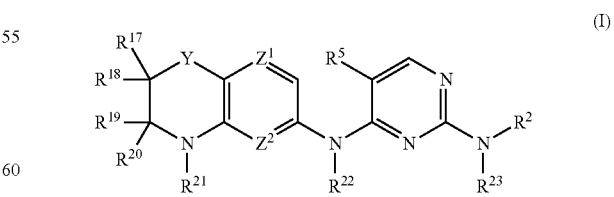

including salts, solvates, hydrates and N-oxides thereof, wherein:

Y is selected from CH$_2$, NR$^{24}$, O, S, S(O) and S(O)$_2$;

$Z^1$ and $Z^2$ are each, independently of one another, selected from CH and N;

$R^2$ is an optionally substituted lower alkyl, lower cycloalkyl, lower heteroalkyl, lower cycloheteroalkyl, aryl, phenyl, or heteroaryl group;

$R^5$ is an electronegative group, such as, for example, a halo, fluoro, cyano, nitro, trihalomethyl or trifluoromethyl group;

$R^{17}$ is selected from hydrogen, halogen, fluoro, lower alkyl and methyl or, alternatively, $R^{17}$ may be taken together with $R^{18}$ to form an oxo (=O) group or, together with the carbon atom to which they are attached, a spirocycle containing from 3 to 7 carbon atoms;

$R^{18}$ is selected from hydrogen, halogen, fluoro, lower alkyl and methyl or, alternatively, $R^{18}$ may be taken together with $R^{17}$ to form an oxo (=O) group or, together with the carbon atom to which they are attached, a spirocycle containing from 3 to 7 carbon atoms;

$R^{19}$ is selected from hydrogen, lower alkyl, and methyl or, alternatively, $R^{19}$ may be taken together with $R^{20}$ to form an oxo (=O) group or, together with the carbon atom to which they are attached, a spirocycle containing from 3 to 7 carbon atoms;

$R^{20}$ is selected from hydrogen, lower alkyl and methyl or, alternatively, $R^{20}$ may be taken together with $R^{19}$ to form an oxo (=O) group or, together with the carbon atom to which they are attached, a spirocycle containing from 3 to 7 carbon atoms;

$R^{21}$, $R^{22}$ and $R^{23}$ are each, independently of one another, selected from hydrogen and a progroup $R^p$ as described herein; and $R^{24}$ is selected from hydrogen, lower alkyl and a progroup $R^p$ as described herein, with the proviso that at least one of $R^{21}$, $R^{22}$, $R^{23}$ and $R^{24}$ must be a progroup $R^p$. In some embodiments, each of $R^{21}$, $R^{22}$ and $R^{23}$ is one of the specific progroups exemplified above and $R^{24}$ is hydrogen. In some embodiments $R^{21}$ is one of the specific progroups exemplified above and $R^{22}$, $R^{23}$ and $R^{24}$ are each hydrogen. In some embodiments, $R^{21}$, $R^{22}$ and $R^{23}$ are each one of the specific progroups exemplified above and $R^{24}$ is lower alkyl.

In another aspect, the present disclosure provides compositions comprising one or more of the prodrugs described herein and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds.

In still another aspect, the present disclosure provides intermediates useful for synthesizing the prodrugs described herein. In the case of phosphate- or phosphite-containing prodrugs, the intermediates generally comprise prodrugs in which the oxygen atoms of the phosphate- and/or phosphite-containing progroups are masked with protecting groups that are selectively removable under specified conditions. In some embodiments, the protecting groups are selectively removable under mildly acidic conditions. In some embodiments, the intermediates are phosphate or phosphite esters which are themselves prodrugs that can be metabolized into active 2,4-pyrimidinediamine compounds. In one illustrative embodiment, the intermediates include prodrugs in which each $R^p$ progroup is, independently of the others, of the formula —$(CR^dR^d)_y$—O—P(O)(OR$^i$)(OR$^i$), —$(CR^dR^d)$y-O—P(O)(OR$^i$)(OH), —$(CR^dR^d)$y-O—P(OR$^i$)(OR$^i$) or —$(CR^dR^d)$y-O—P(OR$^i$)(OH), where each R$^i$ is, independently of the others, selected from lower unsubstituted alkanyl, substituted or unsubstituted phenyl and substituted or unsubstituted benzyl, and R$^d$ and y are as previously defined. In a specific embodiment, the intermediates include phosphate and/or phosphite esters in which each R$^i$ is, independently of the others, selected from lower linear alkanyl, lower branched alkanyl, i-propyl, t-butyl and lower cyclic alkanyl.

In some embodiments, the intermediates comprise an active 2,4-pyrimidinediamine that is substituted at a nitrogen atom of a primary or secondary amine group with a group of the formula —$CR^dR^d$-AH, where $R^d$ and A are as previously defined.

Another aspect of the invention relates to salts of the above-described prodrug compounds. For example, in one aspect of the invention the prodrug is a prodrug salt, or a hydrate, solvate or N-oxide thereof, comprising a 2,4-pyrimidinediamine moiety and at least one progroup salt $R^q$ linked covalently to a primary or secondary amino nitrogen atom of the 2,4-pyrimidinediamine moiety. The 2,4-pyrimidinediamine moiety may be, for example, any of the 2,4-pyrimidinediamine moieties described above. The progroup salt $R^q$ may be any suitable salt of any acidic progroup $R^p$. For example, the progroup salt $R^q$ may be a salt of a phosphate progroup, a carbonate progroup, or a sulfonate progroup. The counterion may be, for example, an alkali cation, an alkaline earth cation or an ammonium cation. Examples of suitable progroup salts $R^q$ include: —$(CR^dR^d)_y$—O—P(O)(O$^-$)$_2$M$^+_2$, —$(CR^dR^d)_y$—O—P(O)(OR$^e$)(O$^-$)M$^+$, —$(CR^dR^d)_y$—O—P(O$^-$)$_2$M$^+_2$, —$(CR^dR^d)_y$—O—P(OR$^e$)(O$^-$)M$^+$, and —$(CR^dR^d)_y$—O—COO$^-$M$^-$, wherein R$^d$, R$^e$, and y are as described above and M$^+$ is as described below.

As used herein, the term "salt" refers not only to species comprised of anions and cations, but also to other forms in which the bonds among atoms are not entirely ionic, e.g., coordination complexes. Similarly, for convenience, chemical structures may be drawn as combinations of anions and cations, e.g., A$^-$B$^+$, but this is not intended to imply that the bonds are necessarily purely ionic.

Another aspect of the invention relates to methods for producing crystalline forms of the salts of the above-described prodrug compounds. In one embodiment of this aspect, the crystalline form of the salt of the prodrugs described herein may contain solvent in the crystal. In a preferred embodiment, the solvent in the crystalline form of the salt of the prodrug is one or more molecules of water per molecule of prodrug.

In yet another aspect, the present disclosure provides methods of synthesizing the intermediates and/or prodrugs described herein. Phosphate-containing prodrugs can be synthesized by reacting an active 2,4-pyrimidinediamine compound with a phosphate ester halide, for example, a phosphate ester halide of the formula X—$(CR^dR^d)_y$—O—P(O)(OR$^j$)(OR$^j$) or X—$(CR^dR^d)_y$—O—P(O)(OR$^j$)(OH), where each R$^j$ is, independently of the others, a selectively removable protecting group; X is a halide, such as, for example, chloride; and R$^d$ and y are as previously defined. In some embodiments, each R$^j$ is R$^e$, where as previously defined. Removal of the selectively removable protecting groups R$^j$ yields a phosphate prodrug. In some embodiments each R$^j$ is the same and is selected from lower linear alkyl, lower branched alkyl and lower cycloalkyl. In some embodiments, each R$^j$ is isopropyl or t-butyl. In embodiments in which mixtures of intermediates are obtained, for example, mixtures of intermediates which contain different numbers of progroups or progroups at different positions on the 2,4-pyrimidinediamine molecule, the desired intermediate can be isolated from the mixture using standard separation and/or isolation techniques (e.g., column chromatography). Alternatively, a desired prodrug can be isolated from a mixture of different prodrugs using standard separation and/or isolation techniques.

Acyclic phosphate ester prodrugs can be obtained in an analogous manner by reacting the active 2,4-pyrimidinediamine with a phosphate ester halide, for example a phosphate ester halide of the formula $X—(CR^dR^d)_y—O—P(O)(OH)(OR^e)$ or $X—(CR^dR^d)_y—O—P(O)(OR^e)(OR^e)$, where X, $R^d$, y and $R^e$ are as previously defined. In this instance, removal of the esterifying groups $R^e$ is not necessary.

Acyclic phosphite and phosphite ester prodrugs can be prepared in an analogous manner from the corresponding phosphite ester halides, for example phosphite ester halides of the formula $X—(CR^dR^d)_y—O—P(OR^j)(OR^j)$, $X—(CR^dR^d)_y—O—P(OR^e)(OH)$, $X—(CR^dR^d)_y—O—P(OR^e)(OR^e)$, where X, $R^d$, y, $R^e$ and $R^j$ are as previously defined.

Cyclic phosphate ester and phosphite ester prodrugs can be prepared by reacting the active 2,4-pyrimidinediamine compound with the corresponding cyclic phosphate ester or phosphite ester halide, for example, a cyclic phosphate ester halide of the formula

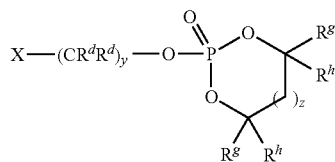

or a cyclic phosphite ester halide of the formula

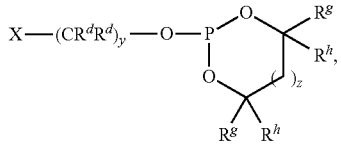

where X, $R^d$, y, z, $R^g$ and $R^h$ are as previously defined.

Embodiments in which $R^p$ is $—CR^dR^d-AR^3$ can be prepared from the corresponding 2,4-pyrimidinediamine drug using conventional methods. For example, when A is O, the intermediates can be synthesized by reacting an active 2,4-pyrimidinediamine compound, with an aldehyde or ketone of the formula $R^d—C(O)—R^d$, where $R^d$ is as previously defined, to yield a corresponding hydroxymethylamine intermediate (where $R^p$ is $—CR^dR^d—OH$). The hydroxymethylamine intermediate can then be converted into the prodrug using standard techniques. In accordance with the definition of $R^p$, the hydroxymethylamine intermediate is also a prodrug of the invention. For example, other drug substances containing secondary amines have been added to formaldehyde to afford their corresponding isolable hydroxymethylamine adducts, Bansal et al., *J. Pharmaceutical Sci.* 1981, 70: (8), 850-854; Bansal et al., *J. Pharmaceutical Sci.* 1981, 70: (8), 855-856; Khan et al., *J. Pharmaceutical and Biomedical Analysis* 1989, 7 (6), 685-691. Alternatively, hydroxyalkyl-containing prodrugs can be prepared in two steps by first reacting the active 2,4-pyrimidinediamine with a bis-functional electrophile, such as a halide of the formula $X^1—CR^dR^d—X^2$, where $X^1$ represents a first halide, $X^2$ represents a second halide and $R^d$ is as previously defined. In a specific exemplary embodiment, the halide is of the formula $I—CR^dR^d—Cl$. The unreacted halide is then hydroxylated to yield the hydroxyalkyl-containing prodrug using standard techniques.

Prodrugs in which A is O, S or $NR^{50}$ can be synthesized from corresponding N-methyl phosphate esters. According to this embodiment, the phosphate ester groups can be displaced with a group of the formula $R^3$-AH, where $R^3$ and A are as previously defined, to yield the prodrug, as discussed in further detail below.

Prodrug salts can be prepared by treating an appropriate conjugate acid prodrug compound with a base, performing any desired cation replacements, and isolating the desired prodrug salt through standard techniques such as precipitation or concentration, or according to the methods described herein.

Crystalline forms of prodrug salts can be prepared according to methods known in the art, or according to the methods described herein. Such crystalline forms may contain only the prodrug salt in the crystal, or may contain a second chemical species in the crystal. For example, crystal forms of the prodrug salts of the present invention may contain one or more solvent molecules per prodrug salt molecule, i.e. a solvate. Examples of solvents which may be contained in the crystalline forms of the prodrugs of the instant invention are water, methanol, ethanol, isopropanol, acetone, and the like. A preferred embodiment of the invention is a hydrate of the prodrug salts described herein.

Many of the prodrugs described herein, and in particular the prodrugs according to structural formula (I), metabolize to yield 2,4-pyrimidinediamine compounds that are potent inhibitors of degranulation of immune cells, such as mast, basophil, neutrophil and/or eosinophil cells. Additional 2,4-pyrimidinediamine compounds that exert similar biological activities that can be formulated as prodrugs as described herein and used in the various methods described herein are described in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003 (US 2005/0028212), international application Serial No. PCT/US03/24087 (WO2004/014382), U.S. application Ser. No. 10/903,263 filed Jul. 30, 2004 (US2005/0234049), and international application Serial No. PCT/US2004/24716 (WO 2005/016893), the disclosures of which are incorporated herein by reference. Thus, in still another aspect, the present disclosure provides methods of regulating, and in particular inhibiting, degranulation of such cells. The method generally involves contacting a cell that degranulates with an amount of a suitable prodrug described herein, or an acceptable salt, hydrate, solvate, N-oxide and/or composition thereof, effective to regulate or inhibit degranulation of the cell. The method may be practiced in in vitro contexts provided that the contacting is performed under conditions in which the progroup(s) metabolize to yield the active 2,4-pyrimidinediamine compound, or in in vivo contexts as a therapeutic approach towards the treatment or prevention of diseases characterized by, caused by or associated with cellular degranulation.

While not intending to be bound by any theory of operation, biochemical data confirm that many of these active 2,4-pyrimidinediamine compounds exert their degranulation inhibitory effect, at least in part, by blocking or inhibiting the signal transduction cascade(s) initiated by crosslinking of the high affinity Fc receptors for IgE ("FcεRI") and/or IgG ("FcγRI") (see, e.g., U.S. application Ser. No. 10/631,029 filed Jul. 29, 2003 (US 2005/0028212), international application Serial No. PCT/US03/24087 (WO2004/014382), U.S. application Ser. No. 10/903,263 filed Jul. 30, 2004 (US2005/0234049), and international application Serial No. PCT/US2004/24716 (WO 2005/016893), the disclosures of which are incorporated herein by reference. Indeed, these active 2,4-pyrimidinediamine compounds are potent inhibitors of both FcεRI-mediated and FcγRI-mediated degranulation. As a consequence, the prodrugs described herein may be used to inhibit these Fc receptor signaling cascades in any cell type expressing such FcεRI and/or FcγRI receptors including but not limited to macrophages, mast, basophil, neutrophil and/or eosinophil cells.

The methods also permit the regulation of, and in particular the inhibition of, downstream processes that result as a consequence of activating such Fc receptor signaling cascade(s). Such downstream processes include, but are not limited to, FcεRI-mediated and/or FcγRI-mediated degranulation, cytokine production and/or the production and/or release of lipid mediators such as leukotrienes and prostaglandins. The method generally involves contacting a cell expressing an Fc receptor, such as one of the cell types discussed above, with an amount of a prodrug described herein, or an acceptable salt, hydrate, solvent, N-oxide and/or composition thereof, effective to regulate or inhibit the Fc receptor signaling cascade and/or a downstream process effected by the activation of this signaling cascade. The method may be practiced in in vitro contexts provided that the contacting is performed under conditions under which the progroup(s) metabolize to yield the active 2,4-pyrimidinediamine compound, or in in vivo contexts as a therapeutic approach towards the treatment or prevention of diseases characterized by, caused by or associated with the Fc receptor signaling cascade, such as diseases effected by the release of granule specific chemical mediators upon degranulation, the release and/or synthesis of cytokines and/or the release and/or synthesis of lipid mediators such as leukotrienes and prostaglandins.

In yet another aspect, the present disclosure provides methods of treating and/or preventing diseases characterized by, caused by or associated with the release of chemical mediators as a consequence of activating Fc receptor signaling cascades, such as FcεRI and/or FcγRI-signaling cascades. The methods may be practiced in animals in veterinary contexts or in humans. The methods generally involve administering to an animal subject or a human an amount of a prodrug described herein, or an acceptable salt, hydrate, solvate, N-oxide and/or composition thereof, effective to treat or prevent the disease. As discussed previously, activation of the FcεRI or FcγRI receptor signaling cascade in certain immune cells leads to the release and/or synthesis of a variety of chemical substances that are pharmacological mediators of a wide variety of diseases. Any of these diseases may be treated or prevented according to the methods of the invention.

For example, in mast cells and basophil cells, activation of the FcεRI or FcγRI signaling cascade leads to the immediate (i.e., within 1-3 min. of receptor activation) release of preformed mediators of atopic and/or Type I hypersensitivity reactions (e.g., histamine, proteases such as tryptase, etc.) via the degranulation process. Such atopic or Type I hypersensitivity reactions include, but are not limited to, anaphylactic reactions to environmental and other allergens (e.g., pollens, insect and/or animal venoms, foods, drugs, contrast dyes, etc.), anaphylactoid reactions, hay fever, allergic conjunctivitis, allergic rhinitis, allergic asthma, atopic dermatitis, eczema, urticaria, mucosal disorders, tissue disorders and certain gastrointestinal disorders.

The immediate release of the preformed mediators via degranulation is followed by the release and/or synthesis of a variety of other chemical mediators, including, among other things, platelet activating factor (PAF), prostaglandins and leukotrienes (e.g., LTC4) and the de novo synthesis and release of cytokines such as TNFα, IL-4, IL-5, IL-6, IL-13, etc. The first of these two processes occurs approximately 3-30 min. following receptor activation; the latter approximately 30 min.-7 hrs. following receptor activation. These "late stage" mediators are thought to be in part responsible for the chronic symptoms of the above-listed atopic and Type I hypersensitivity reactions, and in addition are chemical mediators of inflammation and inflammatory diseases (e.g., osteoarthritis, inflammatory bowel disease, ulcerative colitis, Crohn's disease, idiopathic inflammatory bowel disease, irritable bowel syndrome, spastic colon, etc.), low grade scarring (e.g., scleroderma, increased fibrosis, keloids, post-surgical scars, pulmonary fibrosis, vascular spasms, migraine, reperfusion injury and post myocardial infarction), and sicca complex or syndrome. All of these diseases may be treated or prevented according to the methods described herein.

Additional diseases that can be treated or prevented according to the methods described herein include diseases associated with basophil cell and/or mast cell pathology. Examples of such diseases include, but are not limited to, diseases of the skin such as scleroderma, cardiac diseases such as post myocardial infarction, pulmonary diseases such as pulmonary muscle changes or remodeling and chronic obstructive pulmonary disease (COPD), diseases of the gut such as inflammatory bowel syndrome (spastic colon), acute mycloid leukemia (AML) and immune thrombocytopenic purpura.

Many of the active 2,4-pyrimidinediamine compounds are also potent inhibitors of the tyrosine kinase Syk kinase. Examples of such 2,4-pyrimidinediamine are described, for example, in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003 (US 2005/0028212), international application Serial No. PCT/US03/24087 (WO2004/014382), U.S. application Ser. No. 10/903,263 filed Jul. 30, 2004 (US2005/0234049), and international application Serial No. PCT/US2004/24716 (WO 2005/016893), the disclosures of which are incorporated herein by reference. Thus, in still another aspect, the present disclosure provides methods of regulating, and in particular inhibiting, Syk kinase activity. The method generally involves contacting a Syk kinase or a cell comprising a Syk kinase with an amount of a suitable prodrug, or an acceptable salt, hydrate, solvate, N-oxide and/or composition thereof, effective to regulate or inhibit Syk kinase activity. In one embodiment, the Syk kinase is an isolated or recombinant Syk kinase. In another embodiment, the Syk kinase is an endogenous or recombinant Syk kinase expressed by a cell, for example a mast cell or a basophil cell. The method may be practiced in in vitro contexts provided that the contacting is performed under conditions under which the progroup(s) metabolize to yield the active 2,4-pyrimidinediamine compound, or in in vivo contexts as a therapeutic approach towards the treatment or prevention of diseases characterized by, caused by or associated with Syk kinase activity.

While not intending to be bound by any particular theory of operation, it is believed that such active 2,4-pyrimidinediamine compounds inhibit cellular degranulation and/or the release of other chemical mediators primarily by inhibiting Syk kinase that gets activated through the gamma chain homodimer of FcεRI. This gamma chain homodimer is shared by other Fc receptors, including FcγRI, FcγRIII and FcαRI. For all of these receptors, intracellular signal transduction is mediated by the common gamma chain homodimer. Binding and aggregation of those receptors results in the recruitment and activation of tyrosine kinases such as Syk kinase. As a consequence of these common signaling activities, the prodrugs described herein that metabolize to such active 2,4-pyrimidinediamine compounds may be used to regulate, and in particular inhibit, the signaling cascades of Fc receptors having this gamma chain homodimer, such as FcεRI, FcγRI, FcγRIII and FcαRI, as well as the cellular responses elicited through these receptors.

Syk kinase is known to play a critical role in other signaling cascades. For example, Syk kinase is an effector of B-cell receptor (BCR) signaling (Turner et al., 2000, Immunology Today 21:148-154) and is an essential component of integrin beta(1), beta(2) and beta(3) signaling in neutrophils (Mocsai et al., 2002, Immunity 16:547-558). Active 2,4-pyrimidinediamine compounds that are potent inhibitors of Syk kinase can be used to regulate, and in particular inhibit, any signaling cascade where Syk plays a role, such as, for example, the Fc receptor, BCR and integrin signaling cascades, as well as the cellular responses elicited through these signaling cascades. Thus, the prodrugs described herein that metabolize to such active 2,4-pyrimidinediamine compounds can be used to regulate such activities. The particular cellular response regulated or inhibited will depend, in part, on the specific cell type and receptor signaling cascade, as is well known in the art. Non-limiting examples of cellular responses that may be regulated or inhibited with such prodrugs include a respiratory burst, cellular adhesion, cellular degranulation, cell spreading, cell migration, phagocytosis (e.g., in macrophages), calcium ion flux (e.g., in mast, basophil, neutrophil, eosinophil and B-cells), platelet aggregation, and cell maturation (e.g., in B-cells).

Thus, in another aspect, the present disclosure provides methods of regulating, and in particular inhibiting, signal transduction cascades in which Syk plays a role. The method generally involves contacting a Syk-dependent receptor or a cell expressing a Syk-dependent receptor with an amount of a suitable prodrug described herein, or an acceptable salt, hydrate, solvate, N-oxide and/or composition thereof, effective to regulate or inhibit the signal transduction cascade. The methods may also be used to regulate, and in particular inhibit, downstream processes or cellular responses elicited by activation of the particular Syk-dependent signal transduction cascade. The methods may be practiced to regulate any signal transduction cascade where Syk is now known or later discovered to play a role. The methods may be practiced in in vitro contexts provided that the contacting is performed under conditions under which the progroup(s) metabolize to yield the active 2,4-pyrimidinediamine compound, or in in vivo contexts as a therapeutic approach towards the treatment or prevention of diseases characterized by, caused by or associated with activation of the Syk-dependent signal transduction cascade. Non-limited examples of such diseases include those previously discussed.

Recent studies have shown that activation of platelets by collagen is mediated through the same pathway used by immune receptors, with an immunoreceptor tyrosine kinase motif on the FcRγ playing a pivotal role (Watson & Gibbons, 1998, Immunol. Today 19:260-264), and also that FcRγ plays a pivotal role in the generation of neointimal hyperplasia following balloon injury in mice, most likely through collagen-induced activation of platelets and leukocyte recruitment (Konishi et al., 2002, Circulation 105:912-916). Thus, the prodrugs described herein can also be used to inhibit collagen-induced platelet activation and to treat or prevent diseases associated with or caused by such platelet activation, such as, for example, intimal hyperplasia and restenosis following vascular injury.

Cellular and animal data also confirm that many of these active 2,4-pyrimidinediamine compounds may also be used to treat or prevent autoimmune diseases and/or symptoms of such diseases (see, e.g., U.S. application Ser. No. 10/631,029 filed Jul. 29, 2003 (US 2005/0028212), international application Serial No. PCT/US03/24087 (WO2004/014382), U.S. application Ser. No. 10/903,263 filed Jul. 30, 2004 (US2005/0234049), and international application Serial No. PCT/US2004/24716 (WO 2005/016893), the disclosures of which are incorporated herein by reference. As a consequence, prodrugs of such active 2,4-pyrimidinediamine compounds can likewise be used to treat or prevent such autoimmune diseases and/or symptoms. The methods generally involve administering to a subject suffering from an autoimmune disease or at risk of developing an autoimmune disease an amount of a suitable prodrug described herein, or an acceptable salt, N-oxide, hydrate, solvate or composition thereof, effective to treat or prevent the autoimmune disease and/or its associated symptoms. Autoimmune diseases that can be treated or prevented with the prodrugs include those diseases that are commonly associated with nonanaphylactic hypersensitivity reactions (Type II, Type III and/or Type IV hypersensitivity reactions) and/or those diseases that are mediated, at least in part, by activation of the FcγR signaling cascade in monocyte cells. Such autoimmune disease include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. Additional autoimmune diseases, which can be β-cell (humoral) based or T-cell based, include autoimmune alopecia, Type I or juvenile onset diabetes, and thyroiditis.

BRIEF DESCRIPTION OF THE FIGURES

FIGS. 4-11 provide graphs illustrating various pharmacokinetic data for drug Compound 1 and/or prodrug Compound 4.

DETAILED DESCRIPTION OF THE INVENTION

Definitions

Figure 1A:
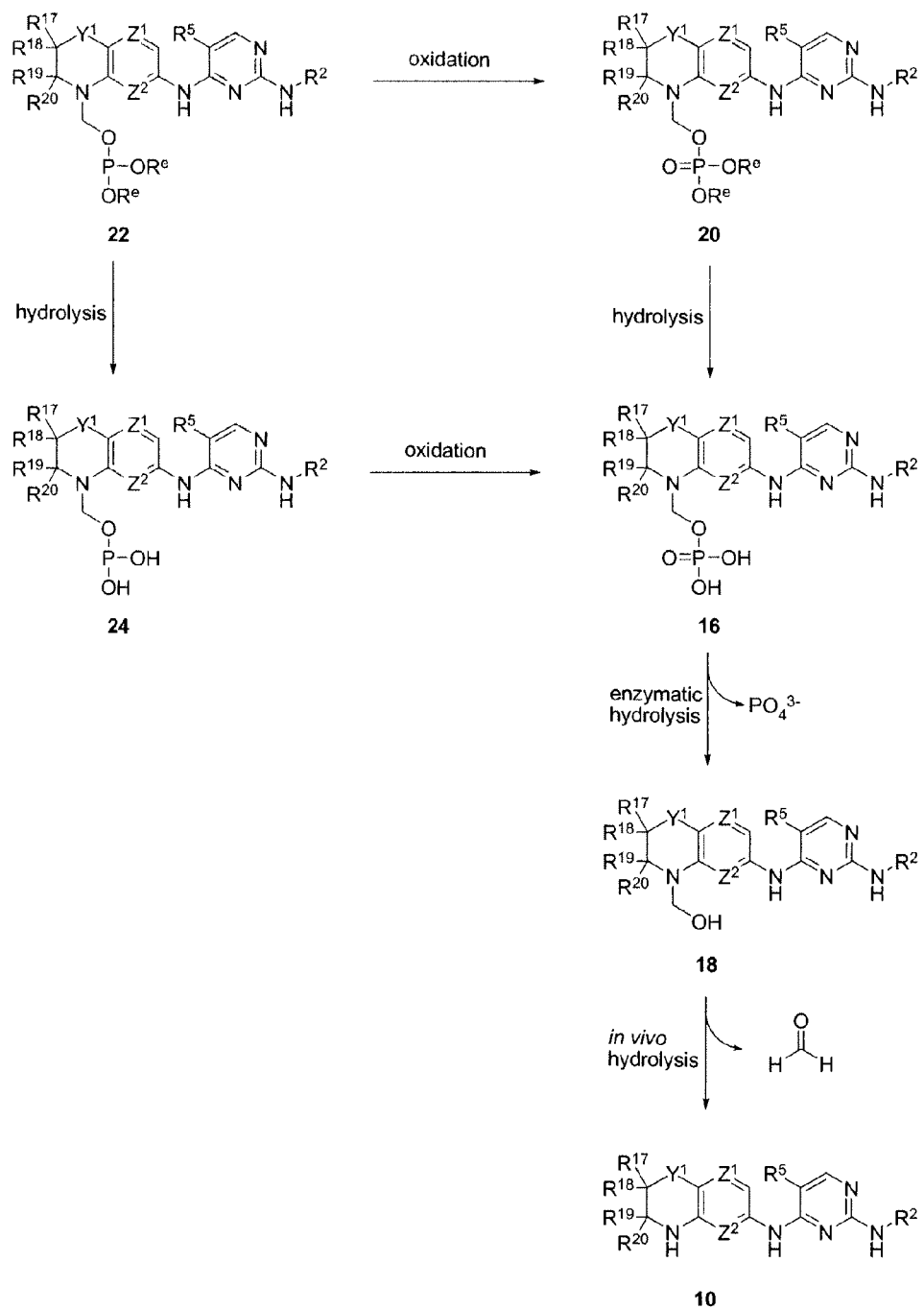
FIG. 1 provides schemes illustrating metabolic pathways of exemplary phosphorous-containing prodrugs.

As used herein, the following terms are intended to have the following meanings:

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. As used herein, "lower alkyl" means (C1-C8) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. As used herein, "lower alkanyl" means (C1-C8) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. As used herein, "lower alkenyl" means (C2-C8) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. As used herein, "lower alkynyl" means (C2-C8) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cyclopropan-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but -1-en-1,4-diyl, 2-methyl-prop-1-en-1,1-diyl, 2-methanylidene-propan-1,1-diyl, buta -1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien -1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In some embodiments, the alkyldiyl group is (C1-C8) alkyldiyl. Specific embodiments include saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In some embodiments, the alkyleno group is (C1-C8) or (C1-C3) alkyleno. Specific embodiments include straight-chain saturated alkano groups, e.g., methano, ethano, propano, butano, and the like.

"Heteroalkyl," Heteroalkanyl," Heteroalkenyl," Heteroalkynyl," Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C8) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C8) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like.

"Aryl" by itself or as part of another substituent refers to a monovalent aromatic hydrocarbon group having the stated number of carbon atoms (i.e., C6-C 15 means from 6 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C6-C15) aryl, with (C6-C10) being more typical. Specific exemplary aryls include phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C6-C15) arylaryl is an arylaryl group in which each aromatic ring comprises from 6 to 15 carbons, e.g., biphenyl, triphenyl, binaphthyl, phenylnaphthyl, etc. In some embodiments, each parent aromatic ring system of an arylaryl group is independently a (C6-C15) aromatic, more preferably a (C6-C10) aromatic. Specific exemplary arylaryl groups include those in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. In some embodiments, the aromatic ring systems are (C6-C15) aromatic rings, more typically (C6-C 10) aromatic rings. A particular exemplary biaryl group is biphenyl.

"Arylalkyl" by itself or as part of another substituent refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In some embodiments, the arylalkyl group is (C7-C21) arylalkyl, e.g., the alkanyl, alkenyl or alkynyl moiety of the arylalkyl group is (C1-C6) and the aryl moiety is (C6-C15). In some specific embodiments the arylalkyl group is (C7-C13), e.g., the alkanyl, alkenyl or alkynyl moiety of the arylalkyl group is (C1-C3) and the aryl moiety is (C6-C10).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Specifically excluded from the definition of "parent heteroaromatic ring system" are benzene rings fused to cyclic polyalkylene glycols such as cyclic polyethylene glycols. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. In some embodiments, each parent heteroaromatic ring system is independently a 5-15 membered heteroaromatic, more typically a 5-10 membered heteroaromatic. Specific exemplary heteroaryl-heteroaryl groups include those in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. In some embodiments, the heteroaromatic ring systems are 5-15 membered heteroaromatic rings, more typically 5-10 membered heteroaromatic rings.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In some specific exemplary embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR'', "alkylamine" refers to a group of the formula —NHR'' and "dialkylamine" refers to a group of the formula —NR''R''', where each R'' is independently an alkyl. As another example, "haloalkoxy" or "haloalkyloxy" refers to a group of the formula —OR''', where R''' is a haloalkyl.

"Substituted," when used to modify a specified group or radical, means that one or more hydrogen atoms of the specified group or radical are each, independently of one another, replaced with the same or different substituent(s). Substituent groups useful for substituting for hydrogens on saturated carbon atoms in the specified group or radical include, but are not limited to —$R^{60}$, halo, —$O^-M^+$, =O, —$OR^{70}$, —$SR^{70}$, —$S^-M^+$, =S, —$NR^{80}R^{80}$, =$NR^{70}$, =N—$OR^{70}$, trihalomethyl, —$CF_3$, —CN, —OCN, —SCN, —NO, —$NO_2$, =$N_2$, —$N_3$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —OC(O)$R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}C(O)O^-M^+$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of alkyl, cycloalkyl, heteroalkyl, cycloheteroalkyl, aryl, arylalkyl, heteroaryl and heteroarylalkyl; each $R^{70}$ is independently hydrogen or $R^{60}$; each $R^{80}$ is independently $R^{70}$ or alternatively, the two $R^{80}$'s, taken together with the nitrogen atom to which they are bonded, form a 5-, 6- or 7-membered cycloheteroalkyl which may optionally include from 1 to 4 of the same or different additional heteroatoms selected from the group consisting of O, N and S; and each M is a counter ion with a single positive charge. Each M+ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$. As specific examples, —$NR^{80}R^{80}$ is meant to include —$NH_2$, —NH-alkyl, N-pyrrolidinyl and N-morpholinyl.

Similarly, substituent groups useful for substituting for hydrogens on unsaturated carbon atoms in the specified group or radical include, but are not limited to, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —OC(O)$R^{70}$, —$OC(S)R^{70}$, —$OC(O)O^-M^|$, —$OC(O)OR^{70}$, —$OC(S)OR^{70}$, —$NR^{70}C(O)R^{70}$, —$NR^{70}C(S)R^{70}$, —$NR^{70}C(O)O^-M^+$, —$NR^{70}C(O)OR^{70}$, —$NR^{70}C(S)OR^{70}$, —$NR^{70}C(O)NR^{80}R^{80}$, —$NR^{70}C(NR^{70}R^{70}$ and —$NR^{70}C(NR^{70})NR^{80}R^{80}$, where $R^{60}$, $R^{70}$, $R^{80}$ and $M^+$ are as previously defined.

Substituent groups, other than $R^p$, useful for substituting for hydrogens on nitrogen atoms in heteroalkyl and cycloheteroalkyl groups include, but are not limited to, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

Substituent groups from the above lists useful for substituting other groups or atoms specified as "substituted" will be apparent to those of skill in the art.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated or alkylated such as benzyl and trityl ethers, as well as alkyl ethers, tetrahydropyranyl ethers, trialkylsilyl ethers (e.g., TMS or TIPPS groups) and allyl ethers.

"Fc Receptor" refers to a member of the family of cell surface molecules that binds the Fc portion (containing the specific constant region) of an immunoglobulin. Each Fc receptor binds immunoglobulins of a specific type. For example the Fcα receptor ("FcαR") binds IgA, the FcεR binds IgE and the FcγR binds IgG.

The FcαR family includes the polymeric Ig receptor involved in epithelial transport of IgA/IgM, the myeloid specific receptor RcαRI (also called CD89), the Fcα/μR and at least two alternative IgA receptors (for a recent review see Monteiro & van de Winkel, 2003, Annu Rev. Immunol, advanced e-publication). The FcγRI is expressed on neutrophils, eosinophils, monocytes/macrophages, dendritic cells and kupfer cells. The FcαRI includes one alpha chain and the FcR gamma homodimer that bears an activation motif (ITAM) in the cytoplasmic domain and phosphorylates Syk kinase.

The FcεR family includes two types, designated FcεRI and FcεRII (also known as CD23). FcεRI is a high affinity receptor (binds IgE with an affinity of about $10^{10}M^{-1}$) found on mast, basophil and eosinophil cells that anchors monomeric IgE to the cell surface. The FcεRI possesses one alpha chain, one beta chain and the gamma chain homodimer discussed above. The FcεRII is a low affinity receptor expressed on mononuclear phagocytes, B lymphocytes, eosinophils and platelets. The FcεRII comprises a single polypeptide chain and does not include the gamma chain homodimer.

The FcγR family includes three types, designated FcγRI (also known as CD64), FcγRII (also known as CD32) and FcγRIII (also known as CD16). FcγRI is a high affinity receptor (binds IgG1 with an affinity of $10^8M^{-1}$) found on mast, basophil, mononuclear, neutrophil, eosinophil, dendritic and phagocyte cells that anchors nomomeric IgG to the cell surface. The FcγRI includes one alpha chain and the gamma chain dimer shared by FcαRI and FcεRI.

The FcγRII is a low affinity receptor expressed on neutrophils, monocytes, eosinophils, platelets and B lymphocytes. The FcγRII includes one alpha chain, and does not include the gamma chain homodimer discussed above.

The FcγRIII is a low affinity (binds IgG1 with an affinity of $5\times10^5M^{-1}$) expressed on NK, eosinophil, macrophage, neutrophil and mast cells. It comprises one alpha chain and the gamma homodimer shared by FcαRI, FcεRI and FcγRI.

Skilled artisans will recognize that the subunit structure and binding properties of these various Fc receptors, as well as the cell types expressing them, are not completely characterized. The above discussion merely reflects the current state-of-the-art regarding these receptors (see, e.g., Immunobiology: The Immune System in Health & Disease, 5$^{th}$ Edition, Janeway et al., Eds, 2001, ISBN 0-8153-3642-x, FIG. 9.30 at pp. 371), and is not intended to be limiting with respect to the myriad receptor signaling cascades that can be regulated with the prodrugs described herein.

"Fc Receptor-Mediated Degranulation" or "Fc Receptor-Induced Degranulation" refers to degranulation that proceeds via an Fc receptor signal transduction cascade initiated by crosslinking of an Fc receptor.

"IgE-Induced Degranulation" or "FcεRI-Mediated Degranulation" refers to degranulation that proceeds via the IgE receptor signal transduction cascade initiated by crosslinking of FcεR1-bound IgE. The crosslinking may be induced by an IgE-specific allergen or other multivalent binding agent, such as an anti-IgE antibody. In mast and/or basophil cells, the FcεRI signaling cascade leading to degranulation may be broken into two stages: upstream and downstream. The upstream stage includes all of the processes that occur prior to calcium ion mobilization. The downstream stage includes calcium ion mobilization and all processes downstream thereof. Compounds that inhibit FcεRI-mediated degranulation may act at any point along the FcεRI-mediated signal transduction cascade. Compounds that selectively inhibit upstream FcεRI-mediated degranulation act to inhibit that portion of the FcεRI signaling cascade upstream of the point at which calcium ion mobilization is induced. In cell-based assays, compounds that selectively inhibit upstream FcεRI-mediated degranulation inhibit degranulation of cells such as mast or basophil cells that are activated or stimulated with an IgE-specific allergen or binding agent (such as an anti-IgE antibody) but do not appreciably inhibit degranulation of cells that are activated or stimulated with degranulating agents that bypass the FcεRI signaling pathway, such as, for example the calcium ionophores ionomycin and A23187.

"IgG-Induced Degranulation" or "FcγRI-Mediated Degranulation" refers to degranulation that proceeds via the FcγRI signal transduction cascade initiated by crosslinking of FcγRI-bound IgG. The crosslinking may be induced by an IgG-specific allergen or another multivalent binding agent, such as an anti-IgG or fragment antibody. Like the FcεRI signaling cascade, in mast and basophil cells the FcγRI signaling cascade also leads to degranulation which may be broken into the same two stages: upstream and downstream. Similar to FcγRI-mediated degranulation, compounds that selectively inhibit upstream FcγRI-mediated degranulation act upstream of the point at which calcium ion mobilization is induced. In cell-based assays, compounds that selectively inhibit upstream FcγRI-mediated degranulation inhibit degranulation of cells such as mast or basophil cells that are activated or stimulated with an IgG-specific allergen or binding agent (such as an anti-IgG antibody or fragment) but do not appreciably inhibit degranulation of cells that are activated or stimulated with degranulating agents that bypass the FcγRI signaling pathway, such as, for example the calcium ionophores ionomycin and A23187.

"Ionophore-Induced Degranulation" or "Ionophore-Mediated Degranulation" refers to degranulation of a cell, such as a mast or basophil cell, that occurs upon exposure to a calcium ionophore such as, for example, ionomycin or A23187.

"Syk Kinase" refers to the well-known 72 kDa non-receptor (cytoplasmic) spleen protein tyrosine kinase expressed in B-cells and other hematopoetic cells. Syk kinase includes two consensus Src-homology 2 (SH2) domains in tandem that bind to phosphorylated immunoreceptor tyrosine-based activation motifs ("ITAMs"), a "linker" domain and a catalytic domain (for a review of the structure and function of Syk kinase see Sada et al., 2001, J. Biochem. (Tokyo) 130:177-186); see also Turner et al., 2000, Immunology Today 21:148-154). Syk kinase has been extensively studied as an effector of B-cell receptor (BCR) signaling (Turner et al., 2000, supra). Syk kinase is also critical for tyrosine phosphorylation of multiple proteins which regulate important pathways leading from immunoreceptors, such as $Ca^{2+}$ mobilization and mitogen-activated protein kinase (MAPK) cascades and degranulation. Syk kinase also plays a critical role in integrin signaling in neutrophils (see, e.g., Mocsai et al. 2002, Immunity 16:547-558).

As used herein, Syk kinase includes kinases from any species of animal, including but not limited to, homosapiens, simian, bovine, porcine, rodent, etc., recognized as belonging to the Syk family. Specifically included are isoforms, splice variants, allelic variants, mutants, both naturally occurring and man-made. The amino acid sequences of such Syk kinases are well known and available from GENBANK. Specific examples of mRNAs encoding different isoforms of human Syk kinase can be found at GENBANK accession no. gi|21361552|ref|NM_003177.2|, gi|496899|emb|Z29630.1|HSSYKPTK[496899] and gi|15030258|gb|BC011399.1|BC011399[15030258], which are incorporated herein by reference.

Skilled artisans will appreciate that tyrosine kinases belonging to other families may have active sites or binding pockets that are similar in three-dimensional structure to that of Syk. As a consequence of this structural similarity, such kinases, referred to herein as "Sykmimics," are expected to catalyze phosphorylation of substrates phosphorylated by Syk. Thus, it will be appreciated that such Syk mimics, signal transduction cascades in which such Syk mimics play a role, and biological responses effected by such Syk mimics and Syk mimic-dependent signaling cascades may be regulated, and in particular inhibited, with many of the prodrugs described herein.

"Syk-Dependent Signaling Cascade" refers to a signal transduction cascade in which Syk kinase plays a role. Non-limiting examples of such Syk-dependent signaling cascades include the FcαRI, FcεRI, FcγRI, FcγRIII, BCR and integrin signaling cascades.

"Autoimmune Disease" refers to those diseases which are commonly associated with the nonanaphylactic hypersensitivity reactions (Type II, Type III and/or Type IV hypersensitivity reactions) that generally result as a consequence of the subject's own humoral and/or cell-mediated immune response to one or more immunogenic substances of endogenous and/or exogenous origin. Such autoimmune diseases are distinguished from diseases associated with the anaphylactic (Type I or IgE-mediated) hypersensitivity reactions.

The Prodrug Compounds

As described in the Summary, the instant disclosure provides prodrugs of biologically active 2,4-pyrimidinediamine compounds, such as the various 2,4-pyrimidinediamine compounds described in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003 2005/0028212), international application Serial No. PCT/US03/24087 (WO2004/014382), U.S. application Ser. No. 10/903,263 filed Jul. 30, 2004 (US2005/0234049), and international application Serial No. PCT/US2004/24716 (WO 2005/016893), the disclosures of which are incorporated herein by reference. Prodrugs of these 2,4-pyrimidinediamine compounds are of particular interest, as these compounds inhibit upstream Fc receptor signaling cascades as well as Syk kinase and Syk kinase-dependent signaling cascades. The prodrugs generally include such active 2,4-pyrimidinediamine compounds in which one or more of the available primary or secondary amine groups is masked with a progroup $R^p$ that metabolizes in vivo to yield the active 2,4 pyrimidinediamine drug. As also discussed in the Summary section, and as will be discussed in more detail, below, the nature of the progroup can vary, and will depend upon, among other factors, the desired water solubility of the prodrug, its intended mode of administration and/or its intended mechanism or site of metabolism to the active 2,4-pyrimidinediamine compound.

For example, it has been discovered that a specific active 2,4-pyrimidinediamine drug (Compound 1, below), exhibits vastly superior water solubility when formulated as a phosphate prodrug (Compound 4, below):

| Compound | Structure | Solubility |
|---|---|---|
| Compound 1 | [chemical structure] | <1 μg/ml |
| Compound 4 | [chemical structure] | >5 mg/ml |

This prodrug Compound 4 also exhibits superior bioavailability compared to the corresponding active drug Compound 1 when administered orally to test animals. In fact, unlike the drug Compound 1, absorption of the prodrug Compound 4 is not dependent upon formulation. In pharmacokinetics studies carried out in rats, the prodrug Compound 4 was absorbed equally well from solutions (e.g., PEG-400 solutions and carboxymethylcellulose solutions) and powders (packed in hard gelatin capsules). While not intending to be bound by any particular theory of operation, it is believed that the improved oral bioavailability of the prodrug Compound 4, as well as its formulation-independent absorption, is due, at least in part, to its higher water-solubility. It is expected that other active 2,4-pyrimidinediamine compounds that have similarly low water solubilities, and hence oral bioavailabilities, will exhibit similar increases in water solubility and oral bioavailability when formulated as phosphate prodrugs. As will be described more fully below, it may be desirable to formulate the active 2,4-pyrimidinediamine compounds as phosphate salts in order to provide high solubility and stability.

Conversely, the corresponding phosphate ester prodrug of active drug Compound 1 would be expected to have lower water-solubility than the active Compound 1 compound. Thus, it is expected that phosphate ester prodrugs of active 2,4-pyrimidinediamine compounds that have lower water-solubility than the corresponding active 2,4-pyrimidinediamine compounds will be especially useful in applications and formulations where low water-solubility is desirable, such as formulations adapted for delivery via inhalation.

One class of active 2,4-pyrimidinediamine compounds that is expected to benefit from formulation as prodrugs, and in particular as phosphate prodrugs, includes 2,4-pyrimidinediamines in which the N4-substituent of the 2,4-pyrimidinediamine moiety is a substituted or unsubstituted nitrogen-containing heteroaryl ring of the formula

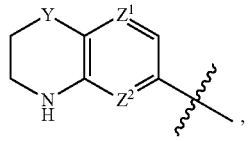

where $Z^1$ and $Z^2$ are each, independently of one another, selected from CH and N and Y is selected from $CH_2$, NH, O, S, S(O) and $S(O)_2$. Such prodrugs can include progroups $R^p$ at: one or both of the non-aromatic ring nitrogens of the heteroaryl ring, the N2-nitrogen of the 2,4-pyrimidinediamine moiety, the N4-nitrogen atom of the 2,4-pyrimidinediamine moiety and/or any available nitrogen atoms in the substituent attached to the N2 nitrogen atom of the 2,4-pyrimidinediamine moiety.

In one illustrative embodiment, the prodrugs are compounds according to structural formula (I):

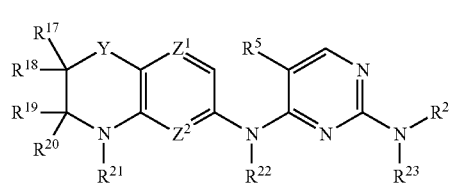

(I)

including salts, solvates, hydrates and N-oxides thereof, wherein:

Y is selected from $CH_2$, $NR^{24}$, O, S, S(O) and $S(O)_2$;

$Z^1$ and $Z^2$ are each, independently of one another, selected from CH and N;

$R^2$ is selected from lower alkyl optionally substituted with one or more of the same or different $R^8$ groups, lower cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C6-C14) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups;

$R^5$ is selected from halo, fluoro, cyano, nitro, trihalomethyl and trifluoromethyl;

$R^8$ is selected from $R^a$, $R^b$, $R^a$ substituted with one or more, for example, from one to four, of the same or different $R^a$ or $R^b$, —$OR^a$ substituted with one or more of the same or different $R^a$ or $R^b$, —$B(OR^a)_2$, —$B(NR^cR^c)_2$, —$(CH_2)_m$—$R^b$, —$(CHR^a)_m$—$R^b$, —O—$(CH_2)_m$—$R^b$, —S—$(CH_2)_m$—$R^b$, —O—$CHR^aR^b$, —O—$CR^a(R^b)_2$, —O—$(CHR^a)_m$—$R^b$, —O—$(CH_2)_m$—$CH[(CH_2)_mR^b]R^b$, —S—$(CHR^a)_m$—$R^b$, —C(O)NH—$(CH_2)_m$—$R^b$, —C(O)NH—$(CHR^a)_m$—$R^b$, —O—$(CH_2)_m$—C(O)NH—$(CH_2)_m$—$R^b$, —S—$(CH_2)_m$—C(O)NH—$(CH_2)_m$—$R^b$, —O—$(CHR^a)_m$—C(O)NH—$(CHR^a)_m$—$R^b$, —S—$(CHR^a)_m$—C(O)NH—$(CHR^a)_m$—$R^b$, —NH—$(CH_2)_m$—$R^b$, —NH—$(CHR^a)_m$—$R^b$, —NH[$(CH_2)_mR^b$], —N[$(CH_2)_mR^b$]$_2$, —NH—C(O)—NH—$(CH_2)_m$—$R^b$, —NH—C(O)—$(CH_2)_m$—$CHR^bR^b$ and —NH—$(CH_2)_m$—C(O)—NH—$(CH_2)_m$—$R^b$;

$R^{17}$ is selected from hydrogen, halogen, fluoro, lower alkyl and methyl or, alternatively, $R^{17}$ may be taken together with $R^{18}$ to form an oxo (=O) group or, together with the carbon atom to which they are attached, a spirocycle containing from 3 to 7 carbon atoms;

$R^{18}$ is selected from hydrogen, halogen, fluoro, lower alkyl and methyl or, alternatively, $R^{18}$ may be taken together with $R^{17}$ to form an oxo (=O) group or, together with the carbon atom to which they are attached, a spirocycle containing from 3 to 7 carbon atoms;

$R^{19}$ is selected from hydrogen, lower alkyl, and methyl or, alternatively, $R^{19}$ may be taken together with $R^{20}$ to form an oxo (=O) group or, together with the carbon atom to which they are attached, a spirocycle containing from 3 to 7 carbon atoms;

$R^{20}$ is selected from hydrogen, lower alkyl and methyl or, alternatively, $R^{20}$ may be taken together with $R^{19}$ to form an oxo (=O) group or, together with the carbon atom to which they are attached, a spirocycle containing from 3 to 7 carbon atoms;

each $R^a$ is, independently of the others, selected from hydrogen, lower alkyl, lower cycloalkyl, cyclohexyl, (C4-C11) cycloalkylalkyl, (C6-C10) aryl, phenyl, (C7-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

each $R^b$ is a suitable group independently selected from =O, —$OR^a$, (C1-C3) haloalkyloxy, =S, —$SR^a$, =$NR^a$, =$NOR^a$, —$NR^cR^c$, halogen, —$CF_3$, —CN, —NC, —OCN, —SCN, —NO, —$NO_2$, =$N_2$, —$N_3$, —$S(O)R^a$, —$S(O)_2R^a$, —$S(O)_2OR^a$, —$S(O)NR^cR^c$, —$S(O)_2NR^cR^c$, —$OS(O)R^a$, —$OS(O)_2R^a$, —$OS(O)_2OR^a$, —$OS(O)_2NR^cR^c$, —$C(O)R^a$, —$C(O)OR^a$, —$C(O)NR^cR^c$, —C(NH)$NR^cR^c$, —C($NR^a$)$NR^cR^c$, —C(NOH)$R^a$, —C(NOH)$NR^cR^c$, —$OC(O)R^a$, —$OC(O)OR^a$, —$OC(O)NR^cR^c$, —$OC(NH)NR^cR^c$, —$OC(NR^a)NR^cR^c$, —[NHC(O)]$_nR^a$, —[$NR^aC(O)$]$_nR^a$, —[NHC (O)]$_n$OR$^a$, —[NR$^a$C(O)]$_n$OR$^a$, —[NHC(O)]$_n$NR$^c$R$^c$, —[NR$^a$C(O)]$_n$NR$^c$R$^c$, —[NHC(NH)]$_n$NR$^c$R$^c$ and —[NR$^a$C(NR$^a$)]$_n$NR$^c$R$^c$;

each R$^c$ is, independently of the others, selected from a protecting group and R$^a$, or, alternatively, the two R$^c$ bonded to the same nitrogen atom are taken together with that nitrogen atom to form a 5 to 8-membered cycloheteroalkyl or heteroaryl which may optionally include one or more of the same or different additional heteroatoms and which may optionally be substituted with one or more, for example, from one to four, of the same or different R$^a$ groups;

R$^{21}$, R$^{22}$ and R$^{23}$ are each, independently of one another, selected from hydrogen and a progroup R$^p$;

R$^{24}$ is selected from hydrogen, lower alkyl and progroup R$^p$;

each m is, independently of the others, an integer from 1 to 3; and each n is, independently of the others, an integer from 0 to 3, with the proviso that at least one of R$^{21}$, R$^{22}$, R$^{23}$ and R$^{24}$ is a progroup.

In the prodrugs described herein, and in particular in the prodrugs of structural formula (I), R$^{21}$, R$^{22}$ and R$^{23}$ each represent either hydrogen or a progroup R$^p$. Also, R$^{24}$ represents hydrogen, a lower alkyl or a progroup R$^p$. Thus, the prodrugs can include a single R$^p$ progroup, two R$^p$ progroups, three R$^p$ progroups, or even more R$^p$ progroups, depending, in part, on the identity of Y and whether the R$^2$ substituent includes any R$^p$ progroups. In some embodiments, it is preferred that the prodrugs described herein, and in particular the prodrugs of structural formula (I), include only one R$^p$ group. Without intending to be bound by any theory of operation, it is possible that the different R$^p$ groups in prodrugs including more than one R$^p$ progroup may metabolize at different rates. Prodrugs including a single R$^p$ progroup would avoid such differential metabolic kinetics. A specific embodiment of prodrugs according to structural formula (I) that include a single progroup R$^p$ are compounds according to structural formula (Ia):

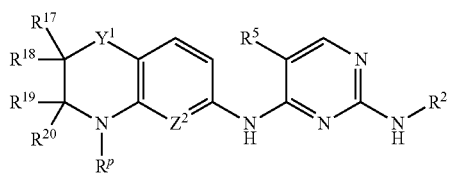
(Ia)

wherein Y$^1$ is selected from CH$_2$, NR$^{24}$, O, S, S(O) and S(O)$_2$; and Z$^2$, R$^2$, R$^5$, R$^{17}$, R$^{18}$, R$^{19}$, R$^{20}$, R$^{24}$ and R$^p$ are as previously defined, with the proviso that R$^2$ does not include any R$^p$ groups.

The identity of any R$^p$ progroups present in the prodrugs described herein is not critical for success, provided that it hydrolyzes under the conditions of use to yield the active 2,4-pyrimidinediamine compound. As will be described more fully below, in certain embodiments of the invention, the R$^p$ progroup is a progroup salt R$^q$.

It has recently been discovered that a phosphate-containing prodrug (Compound 4) according to the structure illustrated below:

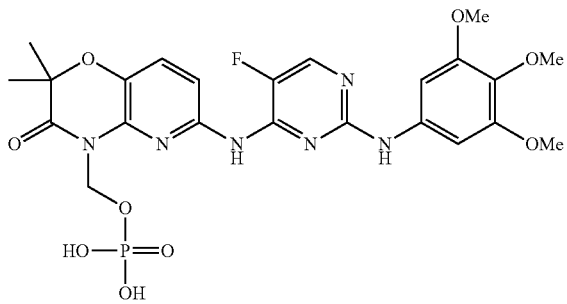

metabolizes in vivo to the corresponding active 2,4-pyrimidinediamine compound (Compound 1), illustrated below:

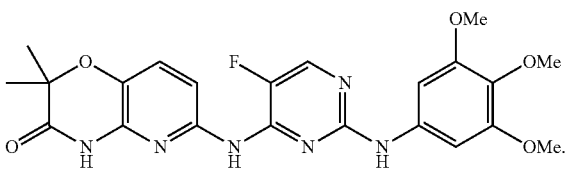

While not intending to be bound by any particular theory of operation, it is believed that this prodrug metabolizes to active Compound 1 via the corresponding hydroxymethylamine intermediate illustrated below:

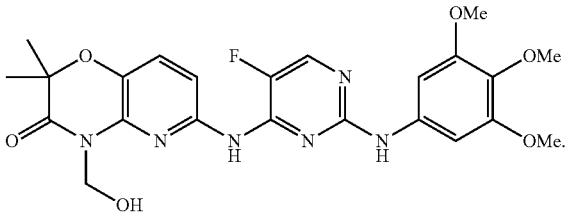

Such hydroxymethylamine compound are known to be unstable under physiological conditions and various pH ranges where they hydrolyze in vivo to yield formaldehyde and the active drug substance. Based on this observation, it is believed that prodrugs that include hydroxyl "protecting" groups that can be metabolized in vivo, for example by the acidic conditions of the stomach and/or by enzymes present in the digestive tract or other organs and/or tissues or fluids with the body, to yield the hydroxymethylamine intermediate illustrated above will likewise metabolize to the active 2,4 pyrimidinediamine drug.

Moreover, it is expected that the amino and thio analogs of this hydroxymethylamine intermediate, will be similarly unstable at physiological conditions and also hydrolyze in vivo to the active 2,4-pyrimidinediamine drug. Accordingly, it is also expected that the corresponding amino and thio compounds, as well as compounds in which the α-amino and α-thio groups are masked with "protecting" groups that are removed under physiological conditions of use to yield the α-amino and α-thio groups, will likewise make suitable prodrugs.

Thus, in some embodiments, the progroup(s) R$^p$ in the prodrugs of structural formulae (I) and (Ia) are of the formula —CR$^d$R$^d$-A-R$^3$, where each R$^d$ is, independently of the other, selected from hydrogen, cyano, —C(O)R$^e$, —C(O)OR$^e$, —C(O)NR$^e$R$^e$, —C(OR$^e$)(OR$^e$), optionally substituted (C1-

C20) alkyl, (C1-C20) perfluoroalkyl, optionally substituted (C7-C30) arylalkyl and optionally substituted 6-30 membered heteroarylalkyl, where each $R^e$ is, independently of the others, selected from hydrogen, alkyl (for example lower alkyl), aryl (for example phenyl or naphthyl, arylalkyl (for example benzyl), heteroaryl and heteroarylalkyl; A is selected from O, S and $NR^{50}$, where $R^{50}$ is selected from $R^d$ and cycloalkyl, or, alternatively, is taken together with $R^3$ such that $R^{50}$ and $R^3$, together with nitrogen atom to which they are attached, form a three-to seven-membered ring; and $R^3$ is a group that, together with A, metabolizes under the conditions of use to yield an intermediate group of the formula —$CR^dR^d$AH, where $R^d$ and A are as previously defined. As mentioned above, compounds of structural formula (I) and (Ia) in which the $R^p$ groups are of the formula —$CR^dR^d$-AH spontaneously hydrolyze in vivo to yield the active 2,4-pyrimidinediamine drug.

The mechanism by which the $R^3$ group metabolizes to yield intermediate group —$CR^dR^d$-A-H is not critical, and can be caused by, for example, hydrolysis under the acidic conditions of the stomach, and/or by enzymes present in the digestive tract and/or tissues or organs of the body. Indeed, the $R^3$ group(s) can be selected to metabolize at a particular site within the body. For example, many esters are cleaved under the acidic conditions found in the stomach. Prodrugs designed to cleave chemically in the stomach to the active 2,4-pyrimidinediamine can employ progroups including such esters. Alternatively, the progroups may be designed to metabolize in the presence of enzymes such as esterases, amidases, lipolases, phosphatases including ATPases and kinase etc., to yield the intermediate group of formula —$CR^dR^d$-A-H. Progroups including linkages capable of metabolizing in vivo to yield such an intermediate group are well-known, and include, by way of example and not limitation, ethers, thioethers, silylethers, silylthioethers, esters, thioesters, carbonates, thiocarbonates, carbamates, thiocarbamates, ureas, thioureas, carboxamides, etc. In some instances, a "precursor" group that is oxidized by oxidative enzymes such as, for example, cytochrome P450 of the liver, to a metabolizable group, can be selected.

The identity of the $R^3$ group can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The $R^3$ group can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, targeting-specific transporters, etc. Groups capable of imparting prodrugs with these characteristics are well-known, and are described, for example, in Ettmayer et al., 2004, J. Med. Chem. 47(10:2393-2404), the disclosure of which is incorporated by reference. All of the various groups described in these references can be utilized in the prodrugs described herein.

In some embodiments, $R^3$ is selected from —$R^f$, —$C(O)R^f$, —$C(O)NR^fR^f$ and —$SiR^fR^fR^f$, where the $R^f$ groups are selected so as to impart the prodrugs with desired bioavailability, cleavage and/or targeting properties. In a specific embodiment, the $R^f$ groups are selected to impart the prodrug with higher water-solubility than the underlying active 2,4-pyrimidinediamine drug. Thus, in some embodiments, the $R^f$ groups are selected such that they, taken together with the heteroatom or group to which they are bonded, are hydrophilic in character. Such hydrophilic groups can be charged or uncharged, as is well-known in the art. As specific examples, the $R^f$ groups may be selected from hydrogen, optionally substituted lower alkyl, optionally substituted lower heteroalkyl, optionally substituted lower cycloalkyl, optionally substituted lower heterocycloalkyl, optionally substituted (C6-C10) aryl, optionally substituted 5-10 membered heteroaryl, optionally substituted (C7-C18) arylalkyl and optionally substituted 6-18 membered heteroarylalkyl. The nature of any present substituents can vary widely, as is known in the art. In some embodiments any present substituents are, independently of one another, selected from $R^b$, defined above.

In a specific embodiment, the progroups on the prodrugs of formula (I) and/or (Ia) are of the formula —$CR^dR^d$-A-$R^3$, where $R^3$ is selected from —$(CH_2)_i$—$R^b$, —$C(O)R^a$, —$C(O)$—$(CH_2)_i$—$R^b$, —$C(O)O$—$R^a$ and —$C(O)O$—$(CH_2)_i$—$R^b$, where X, $R^a$, $R^b$ and $R^d$ are as previously defined, and i is an integer ranging from 0 to 6. Specific, non-limiting, examples of exemplary water-solubility increasing progroups include by the way of example and not limitation, hydrophilic groups such as alkyl, aryl, arylalkyl, or cycloheteroalkyl groups substituted with one or more of an amine, alcohol, a carboxylic acid, a phosphorous acid, a sulfoxide, a sugar, an amino acid, a thiol, a polyol, a ether, a thioether and a quaternary amine salt.

One important class of progroups includes progroups that contain a phosphate group, for example, phosphate-containing progroups of the formula —$(CR^dR^d)_y$—O—$P(O)(OH)_2$, where $R^d$ is as defined above and y is an integer ranging from 1 to 3, typically 1 or 2. In a specific embodiment, each $R^d$ is, independently of the others, selected from hydrogen, substituted or unsubstituted lower alkyl, substituted or unsubstituted (C6-C14) aryl and substituted or unsubstituted (C7-C20) arylalkyl.

While not intending to be bound by any theory of operation, it is believed that such phosphate-containing progroups $R^p$ act as substrates for both alkaline and acid phosphatase enzymes, leading to their removal from the prodrugs under physiological conditions of use. As alkaline phosphatases are abundant in the digestive tract of humans, phosphate-containing progroups $R^p$ that can be cleaved in the presence of alkaline phosphatases are particularly suitable for formulating phosphate-containing prodrugs intended for oral administration. Specific examples of phosphate-containing progroups $R^p$ suitable for use in prodrugs intended for oral administration include, but are not limited to, groups of the formula —$(R^dR^d)_y$—O—$P(O)(OH)_2$ in which each $R^d$ is, independently of the others, selected from hydrogen and unsubstituted lower alkanyl. Exemplary embodiments of such phosphate-containing progroups include, but are not limited to, —$CH_2$—O—$P(O)(OH)_2$ and —$CH_2CH_2$—O—$P(O)(OH)_2$.

Although phosphate-containing prodrugs suitable for oral administration are of interest, skilled artisans will appreciate that prodrugs including phosphate-containing progroups $R^p$ can be administered via other routes of administration, as phosphatases are distributed throughout the body. For example, exemplary prodrug Compound 4 has been found to metabolize to the active drug Compound 1 in in vitro experiments carried out with rat plasma, as well as with rat hepatic and intestinal microsomal preparations, indicating that phosphatases are also present in plasma. Thus, the only requirement is that the particular phosphate-containing progroup $R^p$ selected should be removable under the conditions of intended use.

While not intending to be bound by any theory of operation, it is believed that when y is 1, phosphate-containing prodrugs, such as those according to structural formula (Ia), are metabolized to the active 2,4-pyrimidinediamine compound via the corresponding hydroxymethylamine. This metabolism is illustrated in FIG. 1A. Referring to FIG. 1A, removal of phosphoric acid from phosphate prodrug 16 via enzymatic hydrolysis yields the corresponding hydroxymethylamine 18, which undergoes hydrolysis in vivo to yield formaldehyde and active 2,4-pyrimidinediamine compound 10.

Figure 1B:
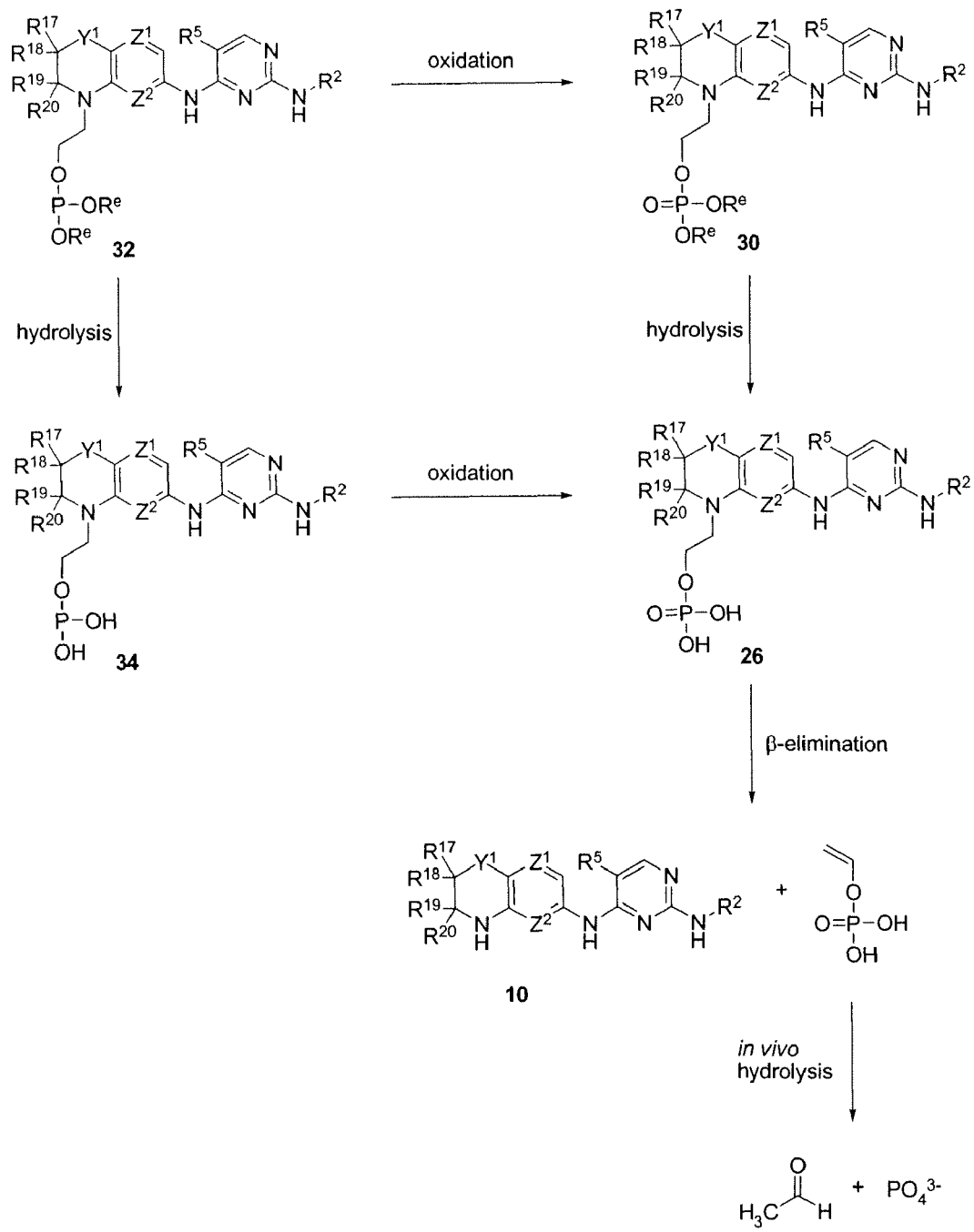
Figure 2:
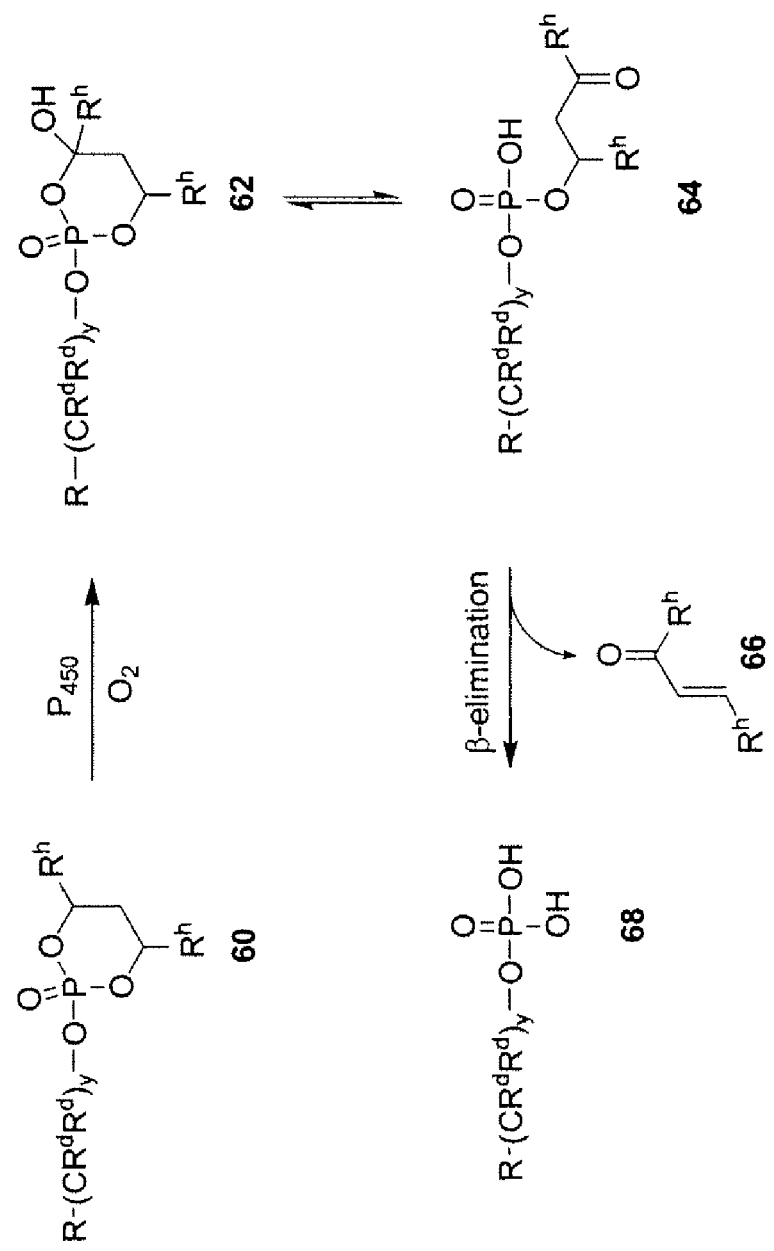
FIG. 2 provides a scheme illustrating a metabolic pathway of an exemplary cyclic phosphate ester prodrug.

Referring to FIG. 1B, when y is 2, it is believed that in vivo hydrolysis of phosphate prodrug 26 yields active 2,4-pyrimidinediamine 10 and enol phosphate, which then hydrolyses in vivo to acetaldehyde and phosphoric acid.

Referring again to FIG. 1A, skilled artisan will appreciate that while hydroxymethylamine 18 metabolizes under physiological conditions to yield active 2,4-pyrimidinediamine compound 10, it is stable at pH 7 and can therefore be prepared and administered as a hydroxyalkyl-containing prodrug of active compound 10. Thus, in some embodiments of the prodrugs of structural formula (I), $R^p$ is a hydroxyalkyl-containing progroup of the formula —$CR^dR^d$—OH, where $R^d$ is as previously defined. In a specific exemplary embodiment, $R^p$ is —$CH_2OH$.

Still referring again to FIG. 1A, skilled artisans will also appreciate that phosphate prodrugs can be generated by in vivo hydrolysis of phosphate ester prodrugs, such as phosphate ester prodrugs 20 and/or by in vivo oxidation of phosphite prodrugs, such as phosphite prodrugs 24. Such phosphate ester and phosphite prodrugs can in turn be generated by either in vivo oxidation or hydrolysis of phosphite ester prodrugs such as phosphite ester prodrugs 22. The corresponding phosphate ester, phosphite and phosphite ester prodrugs of phosphate prodrug 26 are illustrated in FIG. 1B as compounds 30, 34 and 32, respectively. Thus, as will be appreciated by skilled artisans, prodrugs that include precursors of phosphates that can metabolize into phosphate groups in vivo are also included in the present invention.

In some embodiments of such prodrugs, the phosphorous-containing progroup $R^p$ comprises a phosphite group. A specific exemplary embodiment of such phosphite-containing prodrugs includes prodrug compounds in which the progroup $R^p$ is of the formula —$(CR^dR^d)_y$—O—P(OH)(OH), where $R^d$ and y are as previously defined. In other embodiments of such prodrugs, the phosphorous-containing progroup $R^p$ comprises an acyclic phosphate ester or phosphite ester group. Specific exemplary embodiments of such acyclic phosphate ester and phosphite ester prodrugs include progroups $R^p$ of the formula —$(CR^dR^d)_y$—O—P(O)(OH)(OR$^e$), —$(CR^d-R^d)_y$—O—P(O)(OR$^e$)_2, —$(CR^dR^d)_y$—O—P(OH)(OR$^e$) and —$(CR^dR^d)_y$—O—P(OR$^e$)_2, where $R^e$ is selected from substituted or unsubstituted lower alkyl, substituted or unsubstituted (C6-C14) aryl (e.g., phenyl, naphthyl, 4-lower alkoxyphenyl, 4-methoxyphenyl), substituted or unsubstituted (C7-C20) arylalkyl (e.g., benzyl, 1-phenylethan-1-yl, 2-phenylethan-1-yl), —$(CR^dR^d)_y$—OR$^f$, —$(CR^dR^d)_y$—O—C(O)R$^f$, —$(CR^dR^d)_y$—O—C(O)OR$^f$, —$(CR^dR^d)_y$—S—C(O)R$^f$, —$(CR^dR^d)_y$—S—C(O)OR$^f$, —$(CR^dR^d)_y$—NH—C(O)R$^f$, —$(CR^dR^d)_y$—NH—C(O)OR$^f$ and —Si(R$^d$)_3, wherein each $R^f$ is, independently of the others, selected from hydrogen, unsubstituted or substituted lower alkyl, substituted or unsubstituted (C6-C14) aryl, and substituted or unsubstituted (C7-C20) arylalkyl, and $R^d$ and y are as previously defined.

In still other embodiments, phosphorous-containing prodrugs that include phosphate precursors are prodrugs in which the phosphorous-containing progroup $R^p$ comprises a cyclic phosphite ester of the formula

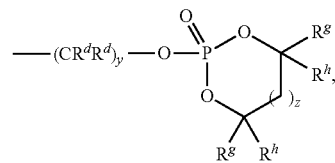

where each $R^g$ is, independently of the others, selected from hydrogen and lower alkyl; each $R^h$ is, independently of the others, selected from hydrogen, substituted or unsubstituted lower alkyl, substituted or unsubstituted lower cycloheteroalkyl, substituted or unsubstituted (C6-C14) aryl, substituted or unsubstituted (C7-C20) arylalkyl and substituted or unsubstituted 5-14 membered heteroaryl; z is an integer ranging from 0 to 2; and $R^d$ and y are as previously defined.

In still other embodiments, phosphorous-containing prodrugs that include phosphate precursors are prodrugs in which the phosphorous-containing progroup $R^p$ comprises a cyclic phosphite ester of the formula

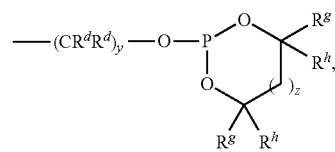

where $R^g$, $R^h$, $R^d$, y and z are as previously defined.

In some embodiments, the substituents $R^h$ on such cyclic phosphate ester and phosphite ester prodrugs are selected such that the progroup is metabolized in vitro by esterase enzymes. Specific examples of such phosphate ester and phosphite ester progroups include those in which each $R^h$ is, independently of the others, selected from hydrogen, lower alkyl, methyl, ethyl and propyl. In some embodiments, such progroups are selected from

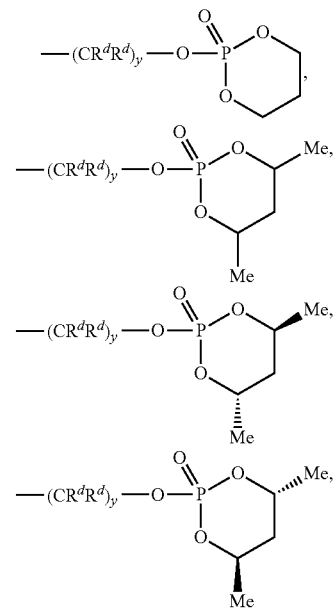

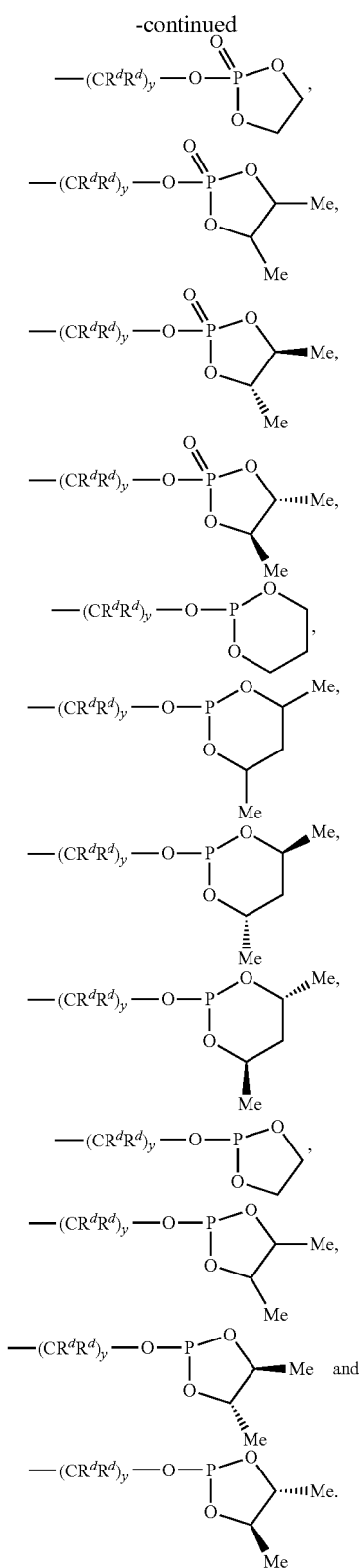

Many of these phosphate esters and phosphite esters are acid label and, when administered orally, metabolize to the corresponding phosphates and phosphites under the acidic conditions of the stomach and/or gut.

Thus, in the phosphorous-containing prodrugs described herein, the identity of the particular phosphorous-containing progroups $R^p$ employed can be selected to tailor the prodrugs for particular modes of delivery, etc.

The suitability of any particular progroup $R^p$ for a desired mode of administration can be confirmed in biochemical assays. For example, if a prodrug is to be administered by injection into a particular tissue or organ, and the identities of the various phosphatases expressed in the tissue or organ are known, the particular prodrug can be tested for metabolism in biochemical assays with the isolated phosphatase(s). Alternatively, the particular prodrug can be tested for metabolism to the active 2,4-pyrimidinediamine compound with tissue and/or organ extracts. Using tissue and/or organ extracts can be of particular convenience when the identity(ies) of the phosphatases expressed in the target tissues or organs are unknown, or in instances when the isolated phosphatases are not conveniently available. Skilled artisans will be able to readily select progroups $R^p$ having metabolic properties (such as kinetics) suitable for particular applications using such in vitro tests. Of course, specific prodrugs could also be tested for suitable metabolism in in vitro animal models.

In some embodiments, the prodrugs are prodrugs according to structural formula (I) or (Ia) that have one or more features selected from:

(i) $R^5$ is fluoro;

(ii) $R^2$ is a phenyl optionally substituted with one or more of the same or different $R^8$ groups;

(iii) $R^2$ is 3,4,5-tri(loweralkoxy)phenyl;

(iv) $R^2$ is 3,4,5-trimethoxyphenyl;

(v) Y or $Y^1$ is O; $Z^1$ is CH, $Z^2$ is N; $R^{17}$ and $R^{18}$ are each methyl; and $R^{19}$ and $R^{20}$ are taken together to form an oxo group; and (vi) $R^p$ is a hydroxyalkyl-containing progroup of the formula —$CH_2OH$, or a phosphate-containing progroup of the formula —$(CR^dR^d)_y$—O—$P(O)(OH)_2$, or a phosphate ester, phosphite or phosphite ester analog thereof, wherein y is 1 or 2 and each $R^d$ is, independently of the others, selected from hydrogen and unsubstituted lower alkyl, or (vii) $R^p$ is selected from —$CH_2OH$, $CH_2$—SH, —$CH_2$—$NH_2$, —$CH_2$—$NHR^{50}$, —$CH_2$—$N(R^{50})_2$, —$CH_2$-A-$R^f$, —$CH_2$-A-$C(O)R^f$, —$CH_2$-A-$C(O)OR^f$ and —$CH_2$-A-$C(O)NR^fR^f$, where A, $R^{50}$ and $R^f$ are as previously defined.

In some embodiments, the prodrugs of structural formulae (I) and (Ia) have two or three of the above-delineated features. In one specific embodiment, the prodrugs have features (i), (iii) and (v). In another specific embodiment, the prodrugs have features (i), (iv) and (v). In still another specific embodiment, the prodrugs have features (i), (iii), (v) and (vi) or (vii). In still another specific embodiment, the prodrugs have features (i), (iv), (v) and (vi) or (vii). In still another specific embodiment, $R^p$ is a phosphate-containing progroup of the formula —$(CR^dR^d)_y$—O—$P(O)(OH)_2$.

In all of the compounds described herein that include substituent alternatives that may be substituted, such as, for example, some of the substituent alternatives delineated for $R^d$, $R^e$, $R^f$, $R^g$, $R^h$, $R^i$ and $R^j$, the substitutions are typically, independently of one another, selected from amongst the $R^b$ groups described in connection with structural formula (I). In a specific embodiment, any present substitutions are, independently of one another, selected from hydroxyl, lower alkoxy, (C6-C14) aryloxy, lower alkoxyalkyl, methoxymethyl, methoxyethyl, ethoxymethyl, ethoxyethyl and halogen.

Those of skill in the art will appreciate that many of the prodrugs described herein, as well as the various prodrug species specifically described and/or illustrated herein, may exhibit the phenomena of tautomerism, conformational isomerism, geometric isomerism and/or optical isomerism. For example, the prodrugs may include one or more chiral centers and/or double bonds and as a consequence may exist as stereoisomers, such as double-bond isomers (i.e., geometric isomers), enantiomers and diasteromers and mixtures thereof, such as racemic mixtures. As another example, the prodrugs may exist in several tautomeric forms, including the enol form, the keto form and mixtures thereof. As the various compound names, formulae and drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the prodrugs having one or more of the utilities described herein, as well as mixtures of these various different isomeric forms. In cases of limited rotation around the 2,4-pyrimidinediamine moiety, atrop isomers are also possible and are also specifically included in the compounds of the invention.

Moreover, skilled artisans will appreciate that when lists of alternative substituents include members which, owing to valency requirements or other reasons, cannot be used to substitute a particular group, the list is intended to be read in context to include those members of the list that are suitable for substituting the particular group. For example, skilled artisans will appreciate that while all of the listed alternatives for $R^b$ can be used to substitute an alkyl group, certain of the alternatives, such as =O, cannot be used to substitute a phenyl group. It is to be understood that only possible combinations of substituent-group pairs are intended.

The prodrugs described herein may be identified by either their chemical structure or their chemical name. When the chemical structure and the chemical name conflict, the chemical structure is determinative of the identity of the specific prodrug.

Depending upon the nature of the various substituents, the prodrugs described herein may be in the form of salts. Such salts include salts suitable for pharmaceutical uses ("pharmaceutically-acceptable salts"), salts suitable for veterinary uses, etc. Such salts may be derived from acids or bases, as is well-known in the art.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethanedisulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, etc.).

The prodrugs described herein, as well as the salts thereof, may also be in the form of hydrates, solvates and N-oxides, as are well-known in the art. Unless specifically indicated otherwise, the expression "prodrug" is intended to encompass such salts, hydrates, solvates and/or N-oxides. Specific exemplary salts include, but are not limited to, mono- and di-sodium salts, mono- and di-potassium salts, mono- and di-lithium salts, mono- and di-alkylamino salts, mono-magnesium salts, mono-calcium salts and ammonium salts.

Another aspect of the invention provides a prodrug salt, i.e., a salt of a prodrug compound described above. For example, one embodiment of the invention provides a prodrug salt, or a hydrate, solvate or N-oxide thereof, comprising a 2,4-pyrimidineamine moiety and at least one progroup salt $R^q$ linked covalently to a primary or secondary amino nitrogen atom of the 2,4-pyrimidinediamine moiety.

The progroup salt $R^q$ may be any suitable salt of any acidic progroup $R^p$. For example, the progroup salt $R^q$ may be a salt of a phosphate-containing progroup, a carbonate-containing progroup, or a sulfonate-containing progroup. The counterion may be, for example, an alkali cation (e.g., Na$^+$), alkaline earth cation (e.g. [Ca$^{2+}$]$_{0.5}$), or an ammonium cation (e.g., NH$_4^+$). Examples of suitable progroup salts $R^q$ include: —(CR$^d$R$^d$)$_y$-A-P(O)(O$^-$)$_2$M$^+_2$, —(CR$^d$R$^d$)$_y$-A-P(O)(OR$^e$)(O$^-$)M$^+$, —(CR$^d$R$^d$)$_y$-A-P(O)(OH)(O$^-$)M$^+$, —(CR$^d$R$^d$)$_y$-A-P(O)$_2$M$^+_2$, —(CR$^d$R$^d$)$_y$-A-P(OR$^e$)(O$^-$)M$^+$, —(CR$^d$R$^d$)$_y$-A-P(OH)(O$^-$)M$^+$, and —(CR$^d$R$^d$)$_y$-A-COO$^-$M$^+$, wherein A, R$^d$, R$^e$, and y are as described above and M$^+$ is as described below. In one embodiment of the invention, A is O.

In one aspect of the invention, the prodrug salt has the structural formula (IX),

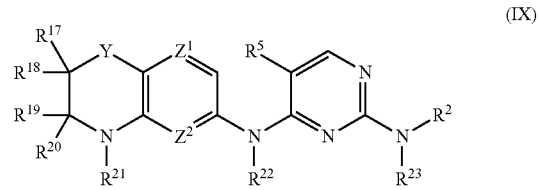

(IX)

in which Y, Z$^1$, Z$^2$, R$^2$, R$^5$, R$^8$, R$^{17}$, R$^{18}$, R$^{19}$, R$^{20}$, R$^a$, R$^b$, R$^c$ and R$^{24}$ are as described above for formula (I), R$^{21}$, R$^{22}$ and R$^{23}$ are each, independently of one another, selected from hydrogen, a progroup R$^p$ and a progroup salt R$^q$;

R$^{24}$ is selected from hydrogen, lower alkyl, a progroup R$^p$ and a progroup salt R$^q$;

each m is, independently of the others, an integer from 1 to 3; and each n is, independently of the others, an integer from 0 to 3, with the proviso that at least one of R$^{21}$, R$^{22}$, R$^{23}$ and R$^{24}$ is a progroup salt R$^q$.

As described above in connection with formula (Ia), in certain embodiments of the invention the prodrug salt includes only one progroup salt R$^q$. A specific embodiment of prodrug salts that include a single progroup salt $R^q$ are compounds according to structural formula (IXa):

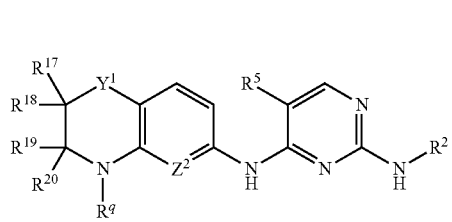

(IXa)

wherein $Y^1$ is selected from $CH_2$, $NR^{24}$, O, S, S(O) and $S(O)_2$; and $Z^2$, $R^2$, $R^5$, $R^{17}$, $R^{18}$, $R^{19}$, $R^{20}$, $R^{24}$ and $R^q$ are as previously defined, with the proviso that $R^2$ does not include any $R^p$ or $R^q$ groups.

In some embodiments, the prodrug salts are prodrug salts according to structural formula (IX) or (IXa) that have one or more features selected from:

(i) $R^5$ is fluoro;

(ii) $R^2$ is a phenyl optionally substituted with one or more of the same or different $R^8$ groups;

(iii) $R^2$ is 3,4,5-tri(loweralkoxy)phenyl;

(iv) $R^2$ is 3,4,5-trimethoxyphenyl;

(v) Y or $Y^1$ is O; $Z^1$ is CH, $Z^2$ is N; $R^{17}$ and $R^{18}$ are each methyl; and $R^{19}$ and $R^{20}$ are taken together to form an oxo group; and (vi) $R^q$ is a phosphate-containing progroup salt of the formula $-(CR^dR^d)_y-O-P(O)(O^-)_2M^+_2$, or a phosphate monoester, phosphite or phosphite monoester analog thereof, wherein y is 1 or 2 and each $R^d$ is, independently of the others, selected from hydrogen and unsubstituted lower alkyl, or (vii) $R^q$ is $-CH_2-A-C(O)O^-M^-$.

In some embodiments of the invention, the prodrug salts of structural formulae (IX) and (IXa) have two or three of the above-delineated features (i)-(vii). In one specific embodiment, the prodrugs have features (i), (iii) and (v). In another specific embodiment, the prodrugs have features (i), (iv) and (v). In still another specific embodiment, the prodrugs have features (i), (iii), (v) and (vi) or (vii). In still another specific embodiment, the prodrugs have features (i), (iv), (v) and (vi) or (vii). In still another specific embodiment, $R^q$ is a phosphate-containing progroup salt of the formula $-(CR^dR^d)_y-O-P(O)(O^-)_2M^l_2$. In another embodiment of the invention, a prodrug salt of formula (IXa) has features (iv) and (v) and the progroup salt $R^q$ is a salt of $-(CR^dR^d)_y-O-P(O)(O^-)_2$, where y is an integer ranging from 1 to 3; each $R^d$ is, independently of the others, selected from hydrogen, optionally substituted lower alkyl, optionally substituted (C6-C14) aryl and optionally substituted (C7-C20) arylalkyl; where the optional substituents are, independently of one another, selected from hydroxyl, lower alkoxy, (C6-C14) aryloxy, lower alkoxyalkyl, methoxymethyl, methoxyethyl, ethoxymethyl, ethoxyethyl and halogen, or, alternatively, two $R^d$ bonded to the same carbon atom are taken together with the carbon atom to which they are bonded to form a cycloalkyl group containing from 3 to 8 carbon atoms. Alternatively, a prodrug salt of formula (IXa) has features (iv) and (v), and the progroup salt $R^q$ is selected from $-CH_2-O-P(O)(O^-)_2M^+_2$ and $-CH_2CH_2-O-P(O)(O^-)_2M^+_2$.

Another aspect of the invention provides prodrug salts having the structure (X):

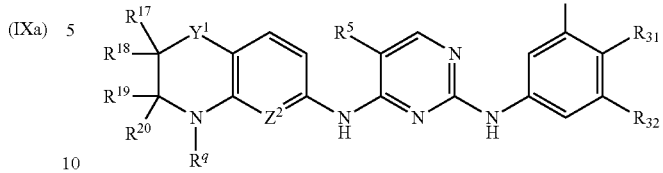

(X)

wherein $Y_1$, $Z_2$, $R_5$, $R_{17}$, $R_{18}$, $R_{19}$ and $R_{20}$ are as described above, $R^{30}$, $R^{31}$ and $R^{32}$ are each, independently of one another, selected from hydrogen, lower alkyl, lower alkenyl, lower alkynyl, (C6-C14) aryl, phenyl, 5-14 membered heteroaryl, (C7-C20) arylalkyl, benzyl, 7-20 membered heteroarylalkyl, —OR, chloro, fluoro, bromo, cyano, nitro, —C(O)R, —C(O)OR, —NRR, —S(O)$_2$NRR, —C(O)NRR, —N(R)S(O)$_2$R and —NC(O)OR, where each R is, independently of the others, selected from hydrogen and lower alkyl; and $R^q$ is selected from $-CH_2-O-P(O)(O^-)_2M^+_2$, $-CH_2CH_2-O-P(O)(O^-)_2\ M^+_2$, $-CH_2-O-P(O)(OH)(O^-)M^+$, and $-CH_2CH_2-O-P(O)(OH)(O^-)M^+$. In one embodiment of the invention, $R^{30}$, $R^{31}$ and $R^{32}$ are each methoxy.

Another aspect of the invention relates to prodrug salts having the structure (XI):

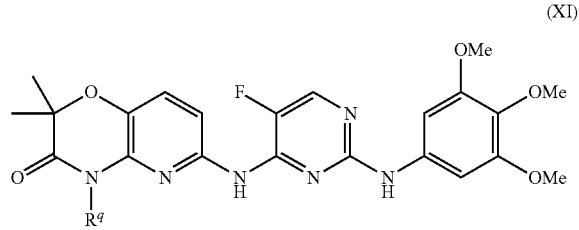

(XI)

in which $R^q$ is $-CH_2-O-P(O)(O^-)_2M^+_2$, $-CH_2CH_2-O-P(O)(O^-)_2\ M^+_2$, $-CH_2-O-P(O)(OH)(O^-)M^+$, or $-CH_2CH_2-O-P(O)(OH)(O^-)M$, and hydrates thereof. $M^+$ may be, for example, an alkali cation, an alkaline earth cation, or an ammonium cation (e.g., a lysine cation or an arginine cation). For example, according to certain embodiments of the invention, $R^q$ may be is $-CH_2-O-P(O)(O^-)_2Na^+_2$; $-CH_2-O-P(O)(OH)(O^-)Na^+$; $-CH_2-O-P(O)(O^-)_2K^+_2$; $-CH_2-O-P(O)(OH)(O^-)K^+$; $-CH_2-O-P(O)(O^-)_2Ca^{2+}$; $-CH_2-O-P(O)(OH)(O^-)[Ca^{2+}]_{0.5}$; $-CH_2-O-P(O)(O^-)_2Mg^{2+}$; or $-CH_2-O-P(O)(OH)(O^-)[Mg^{2+}]_{0.5}$. In certain embodiments of the invention, M+ is an alkali cation, an amino acid cation, or an ammonium cation. In certain embodiments of the invention, the prodrug salts are in solid or semi-solid form, and are not dissolved in aqueous solution.

Another aspect of the invention relates to hydrates of the prodrug salts described above. Hydrates desirably have, for example, ranging from about 1 to about 15 moles of water per mole of prodrug salt. As is described in more detail below, the inventors have determined that prodrug salt hydrates of the present invention have surprisingly desirable stability characteristics, remaining at a stable level of hydration over wide ranges of relative humidities. The inventors surmise that the hydration stability characteristics are due to the high binding energy of the water molecules to the hydrate as well as the special stability of the three dimensional order of the crystalline matrix and its inability to spatially rearrange itself in response to dehydration.

According to one aspect of the invention, prodrug salt hydrates of the invention contain from about 3% to about 17% by weight of water, more preferably from about 13.0% to 16.5% by weight of water. In one embodiment, prodrug salt hydrates of the present invention have the formula

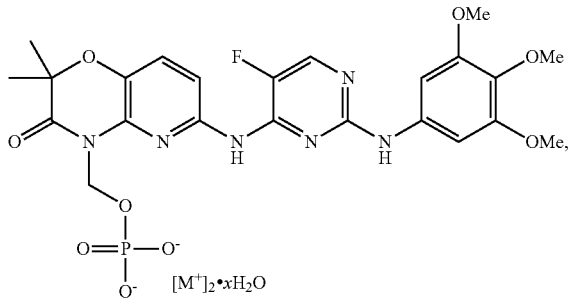

in which x is from about 1 to about 15. More preferably x is from about 5 to about 10. In one particular embodiment, x is from about 5 to about 8. For example, in one embodiment the prodrug salt hydrate of the present invention has the structure:

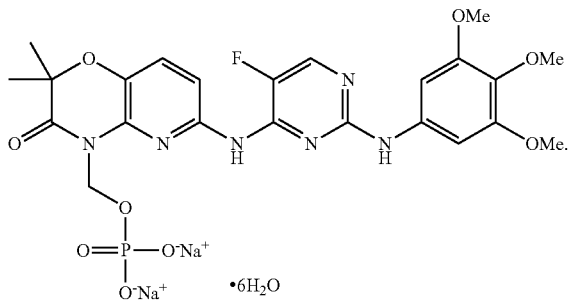

Control of pH in the formation of the salts is desirable. Desirable pH values for the formation of di-$M^+$ salts of compound 4 range from about 8 to about 11, more preferably from about 9 to about 11, even more preferably from about 9.3 to about 10.5. For example, desirable pH values for the formation of the disodium salt of compound 4 fall within these ranges. Desirable pH values for the formation of mono-$M^+$ (e.g., monosodium) salts of compound 4 range from about 5 to about 7, more preferably from about 5 to about 6, even more preferably from about 5.0 to about 5.5.

One embodiment of the invention provides a method for the preparation of a prodrug salt hydrate having the formula

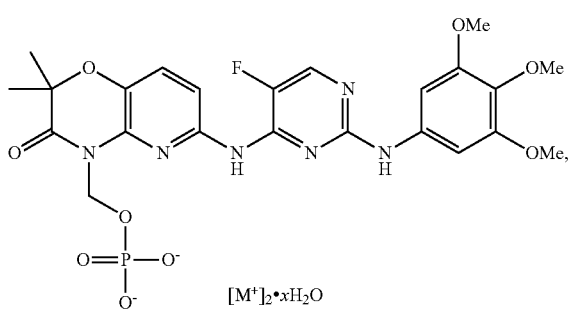

the method comprising precipitating the prodrug salt hydrate from an aqueous solution of the prodrug

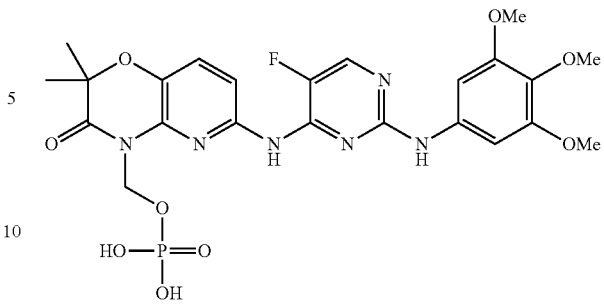

and an [$M^+$]-containing base, the aqueous solution having a pH value in the range of about 9 to about 11. In some embodiments the range is from about 9.3 to about 10.5.

In another embodiment, the invention provides a method for the preparation of a prodrug salt hydrate

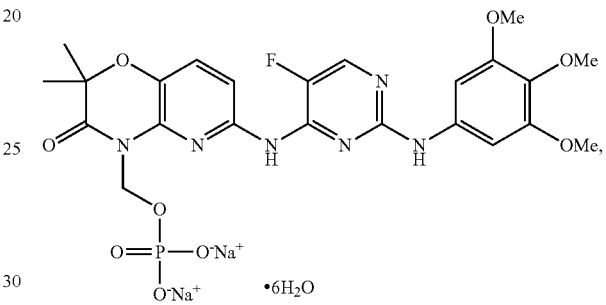

the method comprising precipitating the prodrug salt hydrate from an aqueous solution of the prodrug

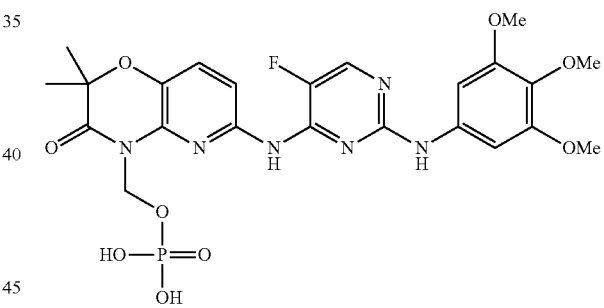

and a sodium-containing base, the aqueous solution having a pH a value in the range of about 9 to about 11. In some embodiments the pH range is from about 9.3 to about 10.5.

One embodiment of the invention provides a method for the preparation of a prodrug salt hydrate having the formula

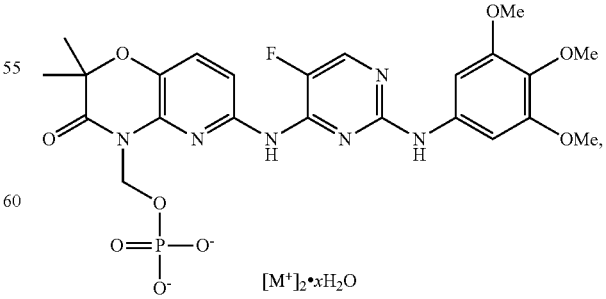

the method comprising adjusting the pH of an aqueous solution of the prodrug

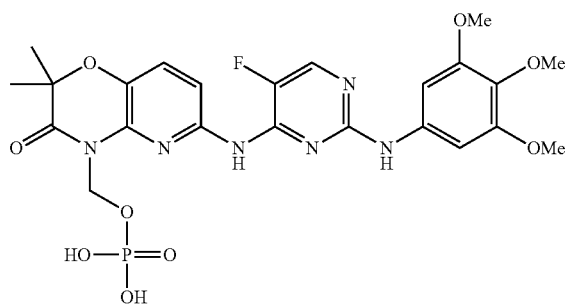

to a value in the range of about 9 to about 11 with an [M⁻]-containing base. In some embodiments the pH is adjusted to a value from about 9.3 to about 10.5.

In another embodiment, the invention provides a method for the preparation of a prodrug salt hydrate

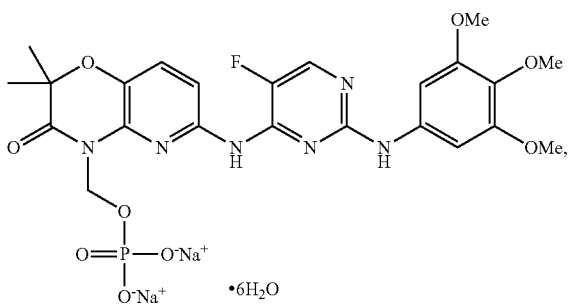

the method comprising adjusting the pH of an aqueous solution of the prodrug

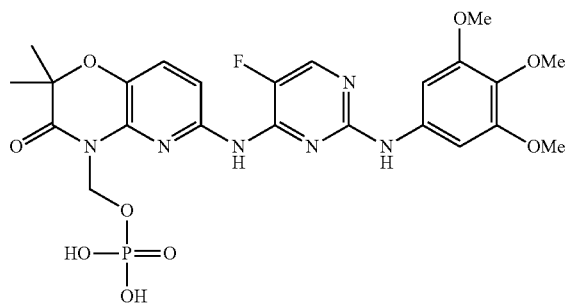

to a value in the range of about 9 to about 11 with a sodium-containing base. In some embodiments the pH is adjusted to a value from about 9.3 to about 10.5.

One embodiment of the invention provides a method for the preparation of a prodrug salt hydrate having the formula

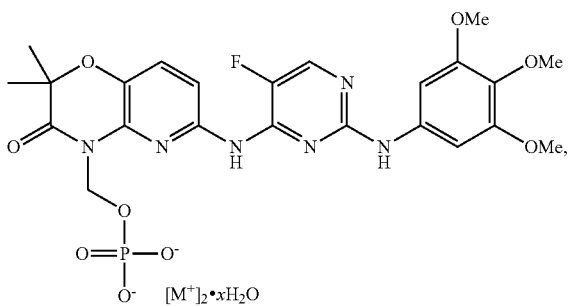

the method comprising:
(i) adjusting the pH of an aqueous solution of the prodrug

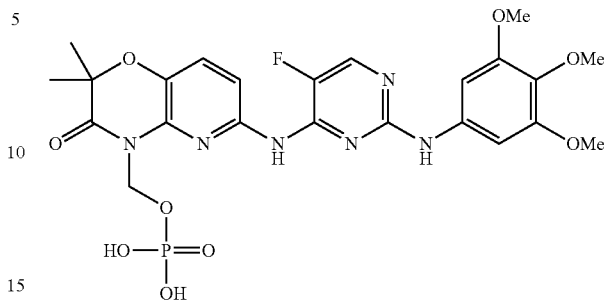

to a value in the range of about 9 to about 11 with an [M⁻]-containing base; and
(ii) precipitating the prodrug salt hydrate from the aqueous solution. In some embodiments the pH is adjusted to a value from about 9.3 to about 10.5.

In another embodiment, the invention provides a method for the preparation of a prodrug salt hydrate

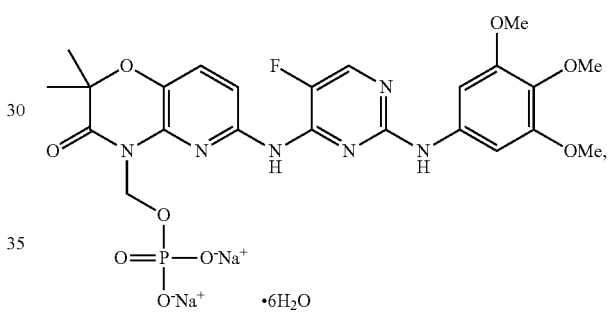

the method comprising:
(i) adjusting the pH of an aqueous solution of the prodrug

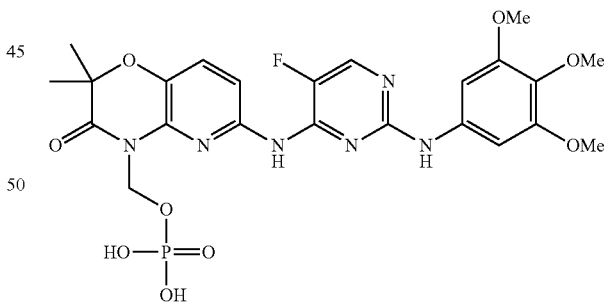

to a value in the range of about 9 to about 11 with a sodium-containing base; and
(ii) precipitating the prodrug salt hydrate from the aqueous solution. In some embodiments the pH is adjusted to a value from about 9.3 to about 10.5.

In some embodiments of the invention precipitating a prodrug salt from an aqueous solution comprises adding an appropriate water-miscible solvent to the aqueous solution. Alternatively, precipitation can be accomplished via salt formation in, or salt addition to, a water/water-miscible solvent mixture to dissolve a prodrug salt, followed by precipitation to provide the prodrug salt hydrate. The addition of a water-miscible solvent to an aqueous prodrug salt solution can hasten the precipitation of a prodrug salt. A water-miscible solvent can be partially water miscible or wholly water miscible. A water-miscible solvent may be a mixture of one or more solvents, wherein one or more of the solvents is water-miscible.

Prodrug salts of the invention may be precipitated at elevated temperatures, ambient temperature, or at sub-ambient temperatures. In one embodiment, the salt is precipitated at ambient temperature. In another embodiment, the salt is precipitated from a warmed solution, either directly or upon cooling. In a specific embodiment, heat is applied to the salt solution prior to precipitation. Heat can be applied to the solution directly or by adding a warmed water-miscible solvent to the aqueous solution. In one embodiment, the prodrug salt solution is heated just before and/or just after adding the water miscible solvent, then allowed to cool to precipitate the salt of the prodrug.

Another embodiment of the invention provides a method for the preparation of a prodrug salt hydrate

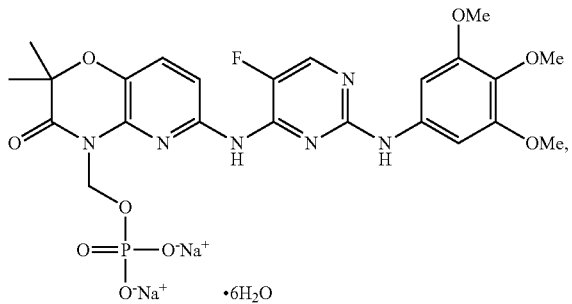

the method comprising:
(i) adjusting the pH of an aqueous solution of the prodrug

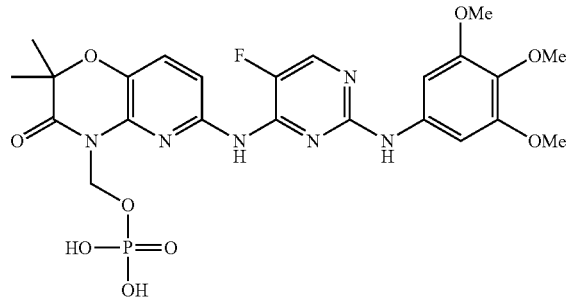

to a value in the range of about 9 to about 11 with a sodium-containing base;
(ii) adding a water-miscible solvent to the aqueous solution;
(iii) heating the aqueous solution before adding the solvent, after adding the water-miscible solvent, or both;
(iv) cooling the aqueous solution to precipitate the prodrug salt hydrate. In some embodiments the pH is adjusted to a value from about 9.3 to about 10.5.

In some embodiments of the invention, one of the above-described methods further comprises isolating the prodrug salt hydrate from the solution. Isolating the prodrug salt hydrate may include, for example, washing the prodrug salt hydrate with at least one wash solvent. Thereafter, substantially all of the wash solvent is removed from prodrug salt hydrate.

In another embodiment, the invention provides a method for the preparation of a prodrug salt hydrate

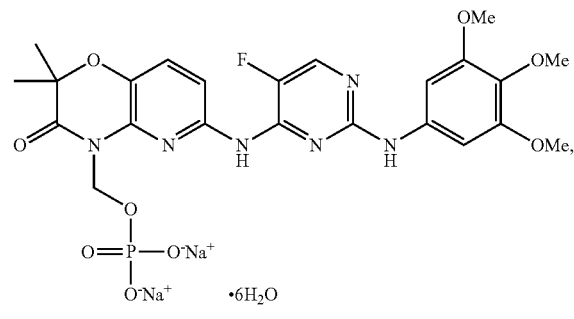

the method comprising:
(i) adjusting the pH of an aqueous solution of the prodrug

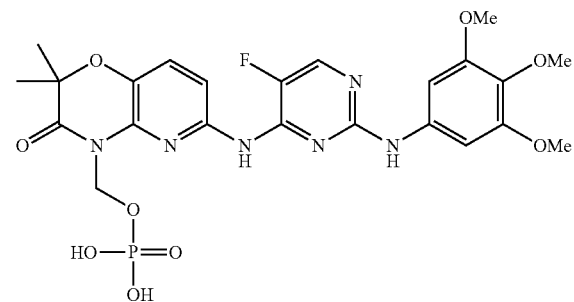

to a value in the range of about 9 to about 11 with a sodium-containing base;
(ii) adding a water-miscible solvent to the aqueous solution;
(iii) heating the aqueous solution, before adding the water miscible solvent, after adding the water-miscible solvent, or before and after adding the water-miscible solvent;
(iv) cooling the aqueous solution to allow precipitation of the prodrug salt hydrate; and
(v) washing the prodrug salt hydrate with at least one wash solvent. In some embodiments the pH is adjusted to a value from about 9.3 to about 10.5.

In some embodiments of the invention, the prodrug salt isolated (e.g., from salt formation in situ and precipitation) is not a desired hydrate form and/or crystalline form. For example, a solid prodrug salt of the invention can be amorphous (solvated or not) or crystalline (solvated or not).

Another aspect of the invention relates to methods of preparation of crystalline forms of hydrates of the prodrug salts described above. In these embodiments, the prodrug salt form is further manipulated to convert it to the desired prodrug salt hydrate and/or crystalline form. For example, in one embodiment, a prodrug salt is isolated and thereafter exposed to conditions under which the solid converts to a desired crystalline and/or hydrate form. For example, using methods described herein, a prodrug salt can be isolated in a crystalline form having less than a desirable amount of water. This crystalline form is exposed to, for example, a moisture-containing environment (e.g., humid or moist atmosphere) to convert it to a desirable hydrate form. In another example, a prodrug salt can be isolated in amorphous form, for example via removing solvent from a solution of the salt under vacuum. The amorphous salt is exposed to a moist atmosphere and is thereby converted over time to a crystalline hydrate.

Depending upon the composition, handling, and isolation techniques, prodrug salts of the invention may be crystalline or amorphous. Also, the aforementioned factors may dictate the water content of the salt form. As mentioned, prodrug salt hydrates of the invention preferably contain from about 3% to about 17% by weight of water, more preferably from about 13.0% to 16.5% by weight of water. In a preferred embodiment, a prodrug having the formula,

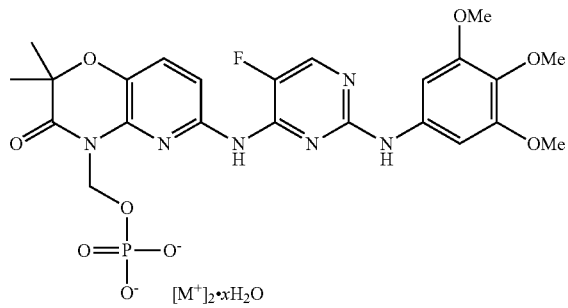

in which x is from about 1 to about 15, is precipitated from an aqueous solution using methods described herein. The prodrug hydrate is isolated as a crystalline or amorphous form. The prodrug hydrate is exposed to a moist environment which over time converts the prodrug hydrate to a crystalline form of desired hydration level. Moist environments include, for example, moist air or moist inert gas; generally "moisture" is used to describe environments having a sufficient degree of moisture to result in hydration of the anhydrous prodrug salt or increased hydration of the prodrug salt hydrate. In a particularly preferred embodiment, the crystalline prodrug hydrate is the disodium hexahydrate form.

In another embodiment, the invention provides a method for the preparation of a crystalline form of the prodrug salt hydrate

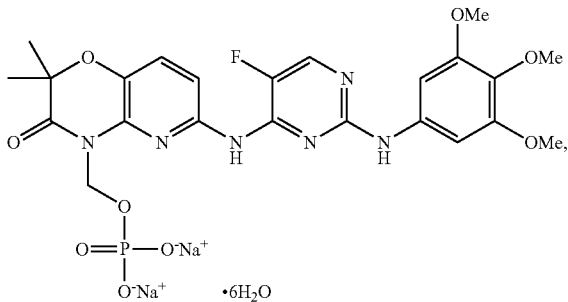

the method comprising:
(i) adjusting the pH of an aqueous solution of the prodrug

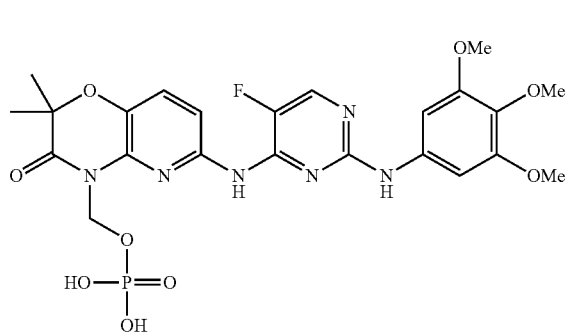

to a value in the range of about 9 to about 11 with a sodium-containing base;

(ii) adding a water-miscible solvent to the aqueous solution;
(iii) heating the aqueous solution, before adding the water miscible solvent, after adding the water-miscible solvent, or before and after adding the water-miscible solvent;
(iv) precipitating a prodrug salt from the aqueous solution via cooling;
(v) washing the prodrug salt with at least one wash solvent;
(vi) removing substantially all of the wash solvent from the prodrug salt; and
(vii) exposing the prodrug salt to moisture, yielding the crystalline form of the prodrug salt hydrate.

In some embodiments the pH is adjusted to a value from about 9.3 to about 10.5. Moist air is typically used as a source of moisture.

In the methods described above, the water-miscible solvent may be, for example, acetonitrile, acetone, isopropanol, methanol or ethanol. In certain embodiments of the methods described above, the water-miscible solvent is isopropanol. As mentioned, the water-miscible solvent may be a mix of two or more solvents, wherein at least one is itself water-miscible.

In the methods described above, the wash solvent may be, for example, isopropanol, methanol, ethanol, acetone, or acetonitrile, or mixtures thereof. In certain embodiments of the methods described above, the precipitated crystals are washed with two wash solvents.

In one embodiment, the invention provides a method for the preparation of a crystalline form of the prodrug salt hydrate

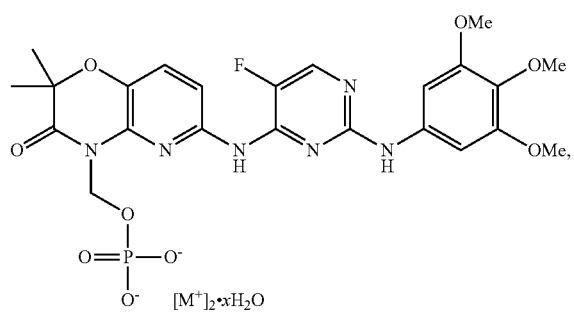

the method comprising
adjusting the pH of an aqueous solution of the prodrug

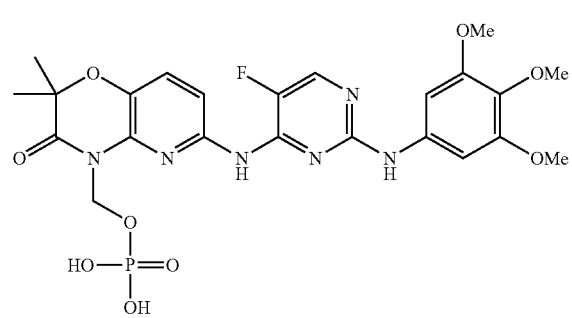

to a value in the range of about 9 to about 11 with an [M$^+$]-containing base;
precipitating a prodrug salt from the aqueous solution; and
exposing the prodrug salt to moisture.

In some embodiments the pH is adjusted to a value from about 9.3 to about 10.5. Moist air is typically used as a source of moisture.

Methods according to this embodiment of the invention may be performed substantially as described above. For example, according to one embodiment of the invention, a method for making a crystalline form of the prodrug salt hydrate

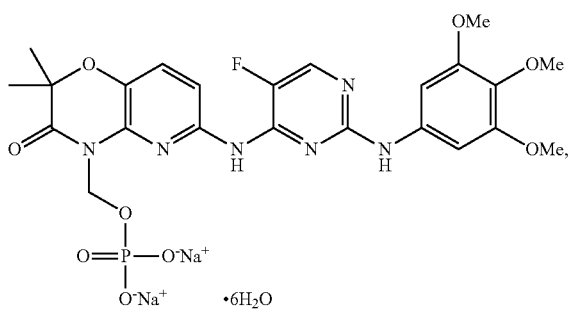

comprises:
(i) adjusting the pH of an aqueous solution of the prodrug

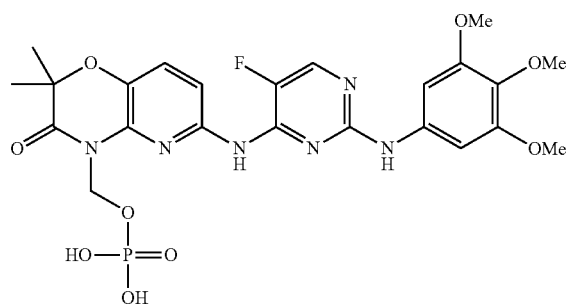

to a value in the range of about 9 to about 11 with a sodium-containing base;
(ii) precipitating a prodrug salt from the aqueous solution; and
(iii) exposing the prodrug salt to moisture.

In some embodiments the pH is adjusted to a value from about 9.3 to about 10.5. Moist air is typically used as a source of moisture.

In a preferred embodiment, the invention provides the method for the preparation of a crystalline form of the prodrug salt hydrate

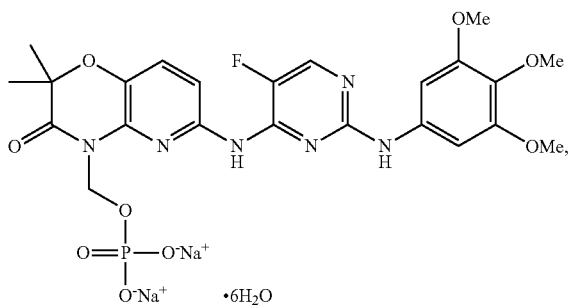

the method comprising the:
(i) adjusting the pH of an aqueous solution of the prodrug

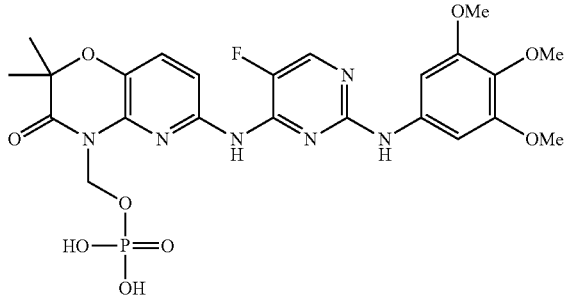

to a value in the range of about 9 to about 11 with NaOH;
(ii) adding isopropanol to the aqueous solution
(iii) heating the aqueous solution, before adding isopropanol, after adding isopropanol, or before and after adding isopropanol;
(iv) cooling the aqueous solution to allow precipitation of a prodrug salt;
(iv) washing the prodrug salt with isopropanol and acetone;
(v) removing substantially all of the solvent from the prodrug salt; and
(vi) exposing the prodrug salt to moisture.

In some embodiments the pH is adjusted to a value from about 9.3 to about 10.5. Moist air or moist inert gas is typically used as a source of moisture.

In the methods described above, the heating steps may be performed, for example, at temperatures above about 50° C.; above about 75° C.; or above about 90° C. In certain embodiments of the invention, the heating step is performed at about the boiling point of the solution.

In the methods described above, the moist air or moist inert gas preferably has a relative humidity of at least about 10%. In embodiments of the methods described above the moist air or moist inert gas has a relative humidity of at least about 20%. In other embodiments of the methods described above, the moist air or moist inert gas has a relative humidity of at least about 30%. In certain embodiments of the methods described above, the moist air or moist inert gas has a relative humidity from about 30% to about 60%.

In the methods described above, the [M$^+$]-containing base may be, for example, a hydroxide, an alkoxide or a carbonate. In the methods described above, the sodium-containing base may be, for example, NaOH, NaOMe, or Na$_2$CO$_3$. In certain embodiments, the sodium-containing base is NaOH.

Another aspect of the invention relates to methods for making forms of mono-M$^+$ (e.g., monosodium) salts of the present invention. In one embodiment of the invention, the invention provides a method for the preparation of a prodrug salt hydrate of the formula

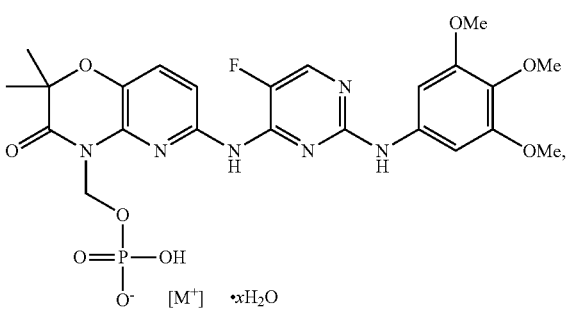

the method comprising:
(i) adjusting the pH of an aqueous solution of the prodrug

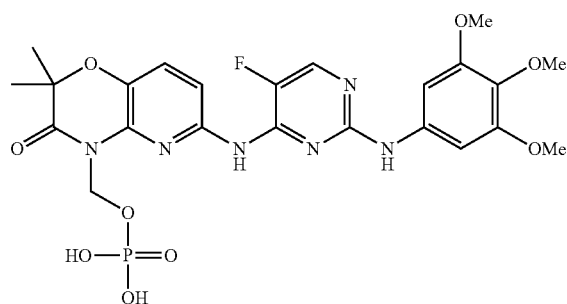

to a value in the range of about 5 to about 6 with an [M+]-containing base; and
(ii) precipitating the prodrug salt hydrate from the aqueous solution.

In some embodiments the pH is adjusted to a value from about 5.0 to about 5.5.

The method for making the mono-M+ salt may be modified as described above for the di-M+ salt and the disodium salts. For example, in one embodiment, the invention provides a method for the preparation of a prodrug salt hydrate

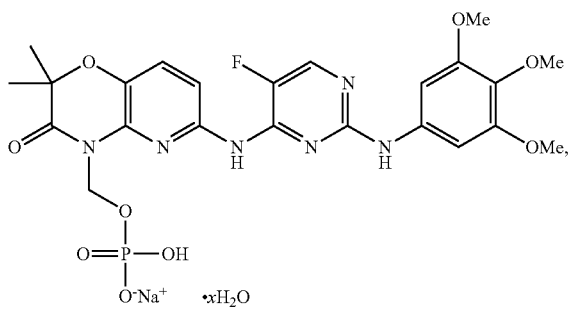

comprising:
(i) adjusting the pH of an aqueous solution of the prodrug

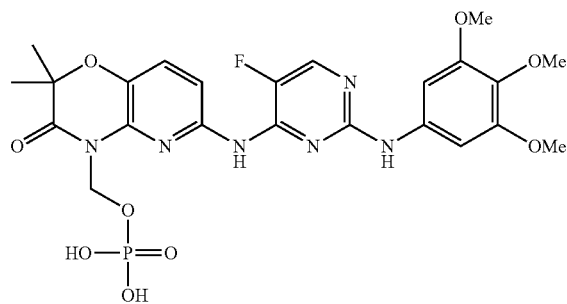

to a value in the range of about 5 to about 6 with a sodium-containing base;
(ii) adding a water-miscible solvent to the aqueous solution;
(iii) heating the aqueous solution, before adding the water miscible solvent, after adding the water-miscible solvent, or before and after adding the water-miscible solvent; and
(iv) cooling the aqueous solution to precipitate the prodrug salt hydrate.

In some embodiments, the pH is adjusted to a value in the range of about 5.0 to about 5.5 with a sodium-containing base.

Another aspect of the invention provides methods of making crystalline hydrate forms of prodrug mono-M+ salts. In one embodiment, an amorphous or crystalline form of the mono-M+ salt is isolated using in situ formation and precipitation as described above. The mono-M+ salt is thereafter exposed to conditions that convert it to a preferred hydrated crystalline form. In a specific example, the mono-M+ salt is exposed to moist air to convert it to a preferred hydrated crystalline form.

Another embodiment of the invention provides a method of preparing a crystalline form of a prodrug salt hydrate having the formula

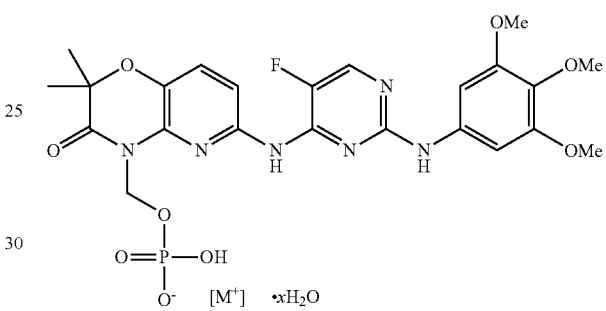

the method comprising
(i) adjusting the pH of an aqueous solution of the prodrug

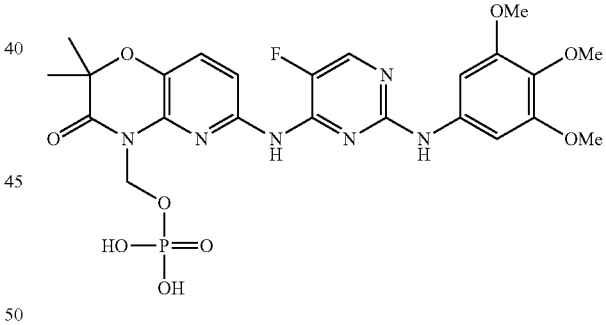

to a value in the range of about 5 to about 7 with an [M+]-containing base;
(ii) precipitating a prodrug salt from the solution; and
(iii) exposing the prodrug salt to moisture, yielding the crystalline form of the prodrug salt hydrate.

Another aspect of the invention provides a pharmaceutical composition comprising a prodrug salt hydrate as prepared by any of the methods described above and a pharmaceutically acceptable carrier, diluent and/or excipient.

Methods of Synthesis

The prodrugs and prodrug salts described herein, as well as intermediates therefore, may be synthesized via a variety of different synthetic routes using commercially available starting materials and/or starting materials prepared by conventional synthetic methods. Suitable exemplary methods that may be routinely used and/or adapted to synthesize active 2,4-pyrimidinediamine compounds can be found in U.S. Pat. No. 5,958,935, U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003 (US 2005/0028212), international application Serial No. PCT/US03/24087 (WO2004/014382), U.S. application Ser. No. 10/903,263 filed Jul. 30, 2004 (US2005/0234049), and international application Serial No. PCT/US2004/24716 (WO 2005/016893), the disclosures of which are incorporated herein by reference. These active 2,4-pyrimidinediamine compounds can be used as starting materials to synthesize the prodrugs. Specific examples describing the synthesis of phosphate prodrug Compound 4, as well as a synthetic intermediate therefore, are provided in the Examples section. All of the prodrugs described herein may be synthesized by routine adaptation of this method.

For example, some embodiments of prodrugs according to structural formula (I) and/or (Ia) can be prepared by reacting the corresponding active 2,4-pyrimidinediamine (i.e., compounds according to structural formulae (I) and/or (Ia) in which each $R^p$ is hydrogen) with an aldehyde or a ketone to give an α-hydroxymethyl amine, which can then be reacted with an electrophile to yield a prodrug. An exemplary synthesis of this type is illustrated in Scheme (I), below:

In Scheme (I), $Y^1$, $Z^1$, $Z^2$, $R^2$, $R^5$, $R^{17}$, $R^{18}$, $R^{19}$ and $R^{20}$ are as defined for structural formula (I) or (Ia). $R^3$ and $R^d$ are as defined in the text, supra. According to Scheme (I), active 2,4-pyrimidinediamine 10 is reacted with ketone 12 to yield a mixture of four products: unreacted starting material 10 (not illustrated) and compounds 14a, 14b and 14c. At this stage, the products can be isolated from one another using standard chromatographic techniques. Reaction with electropholic $R^3$ yields prodrugs 15a, 15b and 15c.

As illustrated above, α-hydroxymethylamines 14a, 14b and 14c can be converted into a variety of different types of prodrugs 15a, 15b and 15c. For example, the α-hydroxymethylamines can be reacted with an alcohol in the presence of a strong acid catalyst, or a carbon-bearing halide (e.g., $CH_3Br$), to yield the corresponding ether derivatives (e.g., compounds in which $R^3$ is $R^f$, where $R^f$ is as previously defined).

Reacting α-hydroxymethylamines 14a, 14b and 14c with a carboxylic acid in the presence of a strong acid catalyst or a carboxylic acid anhydride or a carboxylic acid halide (e.g. with an appropriate acid scavenger) yields the corresponding ester derivatives (e.g., compounds in which $R^3$ is —C(O)$R^f$, where $R^f$ is as defined above).

Reaction of α-hydroxymethylamines 14a, 14b and 14c with a haloformate ester (e.g., Cl—C(O)OCH$_3$) yields the corresponding carbonate derivatives (e.g., compounds in which $R^3$ is —C(O)O$R^f$, where $R^f$ is as previously defined).

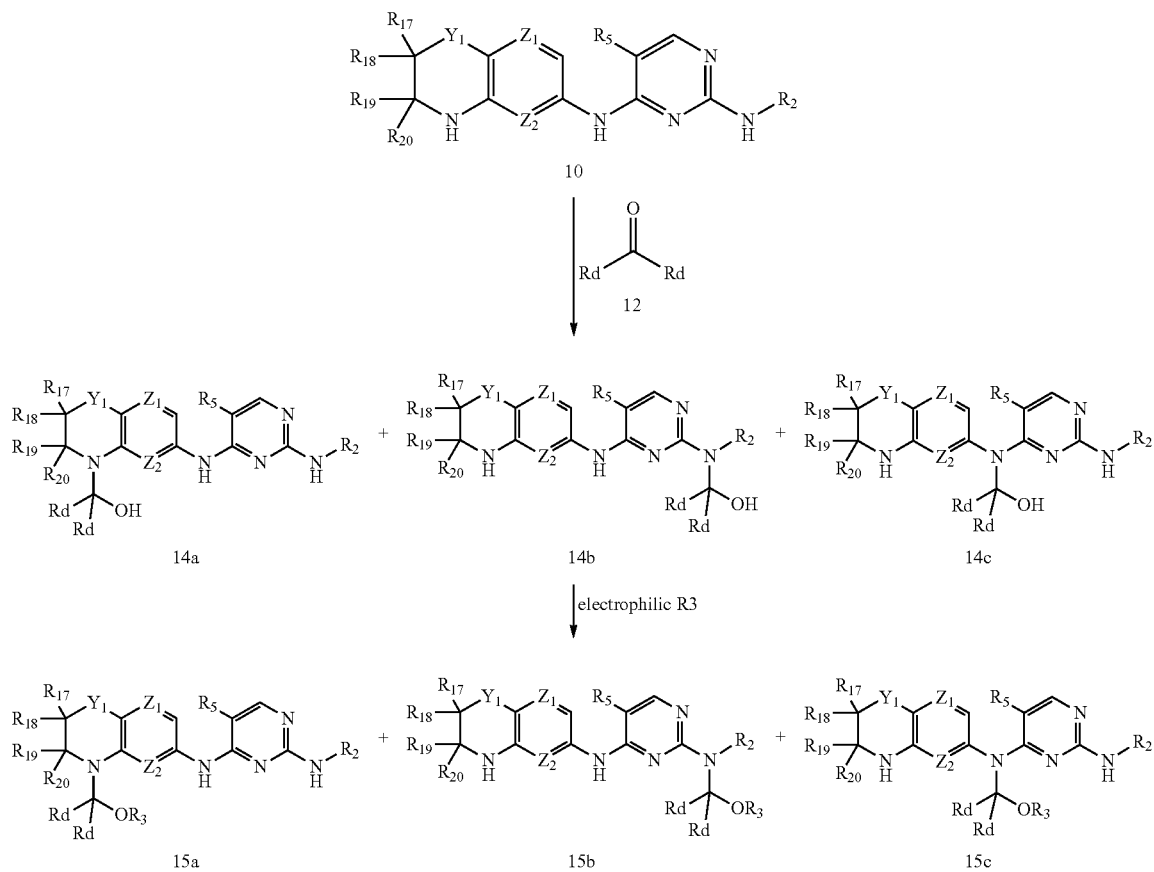

Reaction of α-hydroxymethylamines 14a, 14b and 14c with a haloformamide (e.g., Cl—C(O)N(CH$_3$)$_2$) yields the corresponding carbamate or urethane derivatives (e.g., compounds in which R$^3$ is —C(O)NR$^f$R$^f$, where R$^f$ is as previously defined).

As will be recognized by skilled artisans, other hydroxyl protecting groups could also be used, including, for example, the various different hydroxyl protecting groups described in Green & Wuts, "*Protective Groups in Organic Chemistry,*" 2d Edition, John Wiley & Sons, New York, pp. 10-142, the disclosure of which is incorporated herein by reference.

Alternatively, prodrugs according to structural formulae (I) and (Ia) can be synthesized by nucleophilic substitution of the corresponding phosphate esters. An example of this synthetic route is illustrated in Scheme (II), below:

According to Scheme (II), active 2,4-pyrimidinediamine 10 is reacted with di-tert-butyl chloromethylphosphate 13 in the presence of cesium carbonate to yield a mixture of four products: unreacted starting material 10 (not illustrated) and phosphate esters 17a, 17b and 17c, which are themselves prodrugs as described herein. When R$^2$ is 3,4,5-trimethoxyphenyl phosphate ester 17a is the major product. Reaction of this phosphate ester 17a with R$^3$-AH (where A is O, S, or NR$^{50}$), yields prodrug 19. The minor phosphate esters 17b and 17c can be similarly reacted to yield the corresponding prodrugs.

Di-tent-butyl chloromethyl phosphate 13 can be prepared from di-tent-butyl phosphate as illustrated in Scheme (III), below:

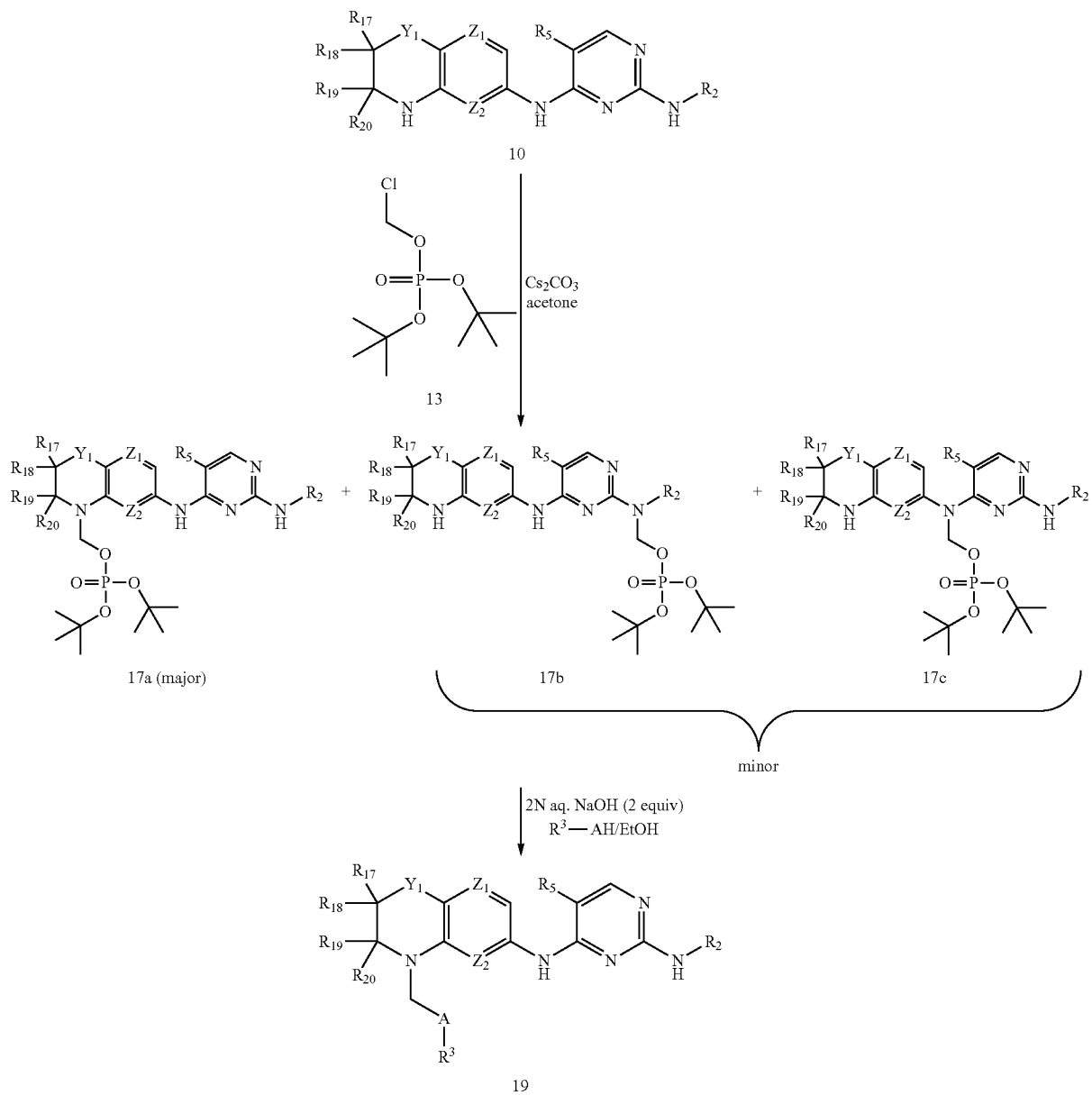

Scheme (III)

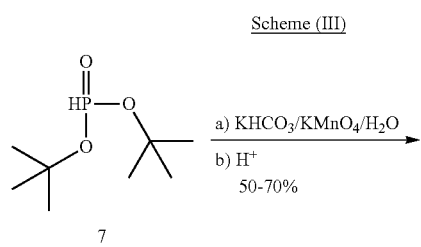
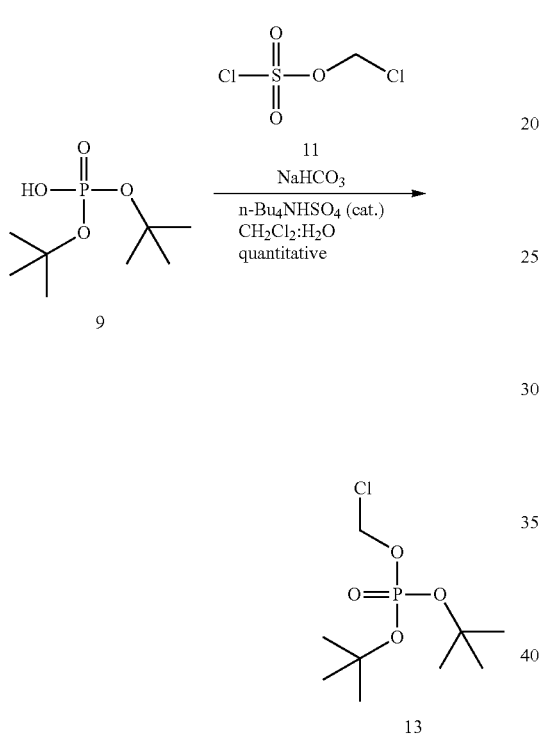

According to Scheme (III), di-tent-butyl phosphate 9 is obtained from the corresponding di-tent-butyl phosphite 7 as described in Krise et al., 1990, J. Med. Chem. 42:3793-3794. Reaction of phosphate 9 with chloromethyl chlorosulfate 11 (available from Synergetica, Inc., Sicklerville, N.J. 08081) as described in Mantyla et al., 2002, Tet. Lett. 43:3793-3794 yields di-tent-butyl chloromethyl phosphate 13, which can be used in Scheme (II), above, crude without purification.

Although the Schemes illustrated above depict the synthesis of prodrugs that include a single progroup, prodrugs having a plurality of progroups could be obtained by adjusting the number of equivalents of reagent 12 or 13 used.

As another alternative to Scheme (I), hydroxymethylamine 14a can be prepared in a two-step process by first reacting active 2,4-pyrimidinediamine 10 with a bis functional electrophile, such as, for example, chloro-iodomethane (I—CH$_2$Cl), to yield a chloro-methyl intermediate, which can then be hydroxylated by reaction with basic hydroxide or reacted with various nucleophilic reagents such as alkoxides, amines or sulfide to make R$^p$. Specific conditions for carrying out reactions of this type that can be used to synthesize the prodrugs described herein, for example, in Bansal et al., 1981, J. Pharm. Sci. 70(8):850-854 and Bansal et al., 1981, J. Pharm. Sci. 70(8):855-857, the disclosures of which are incorporated herein by reference.

An exemplary synthetic route that can be used to synthesize an exemplary phosphate prodrug 16 according to structural formula (Ia) is illustrated in Scheme (IV), below. This method may be routinely adapted to synthesize the full range of phosphate prodrugs described herein.

Scheme (IV)

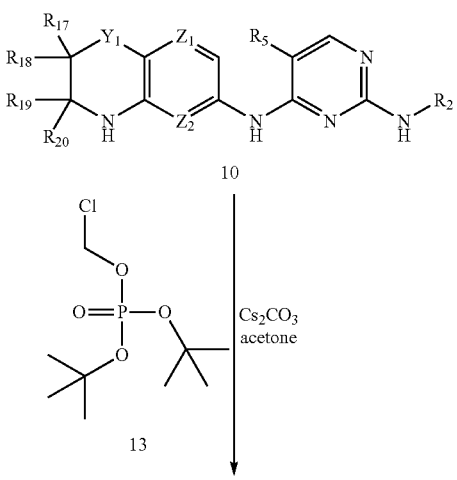

-continued

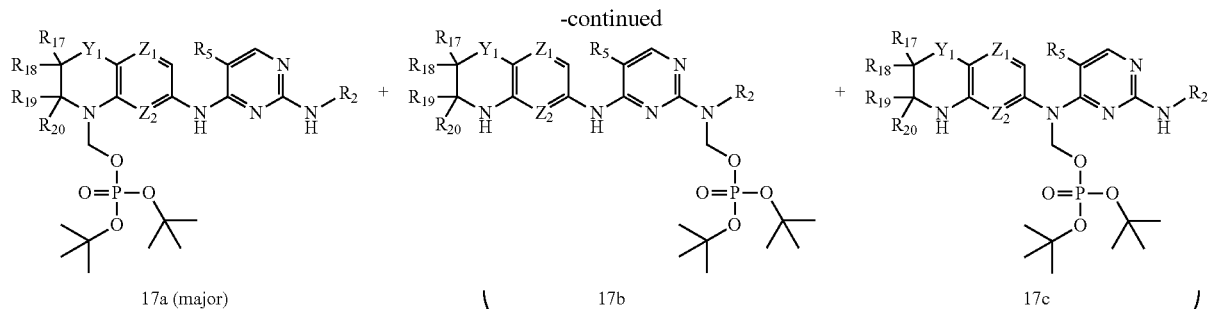

17a (major)    17b    17c
                      minor 15-20% TFA/CH₂Cl₂

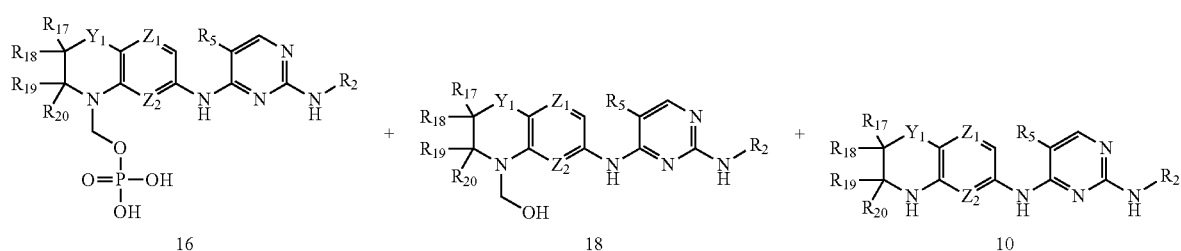

16    18    10

In Scheme (IV), $Y^1$, $Z^1$, $Z^2$, $R^2$, $R^5$, $R^{17}$, $R^{18}$, $R^{19}$ and $R^{20}$ are as defined for structural formula (I) or (Ia). According to Scheme (IV), active 2,4-pyrimidinediamine 10 is reacted with di-tent-butyl chloromethylphosphate 13 in the presence of cesium carbonate to yield a mixture of four products: unreacted starting material 10 (not illustrated) and compounds 17a, 17b and 17c. When $R^2$ is 3,4,5-trimethyoxyphenyl, compound 17a is the major product. At this stage, the major product can be isolated from the minor products using standard chromatographic techniques. Removal of the tert-butyl groups yields a mixture of desired product 16 and impurities 18 and 10. The desired product 16 can be isolated using standard techniques.

An alternative method of obtaining phosphate prodrug 16 is illustrated in Scheme (V); below.

Scheme (V)

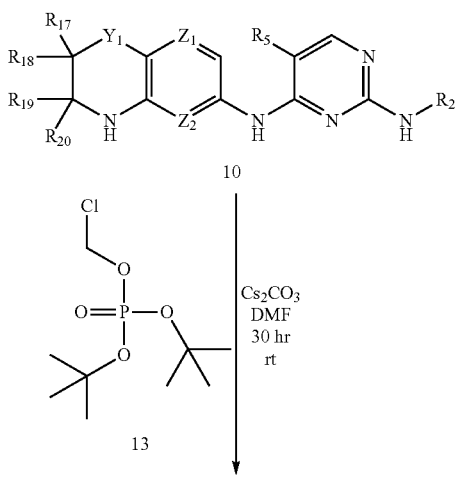

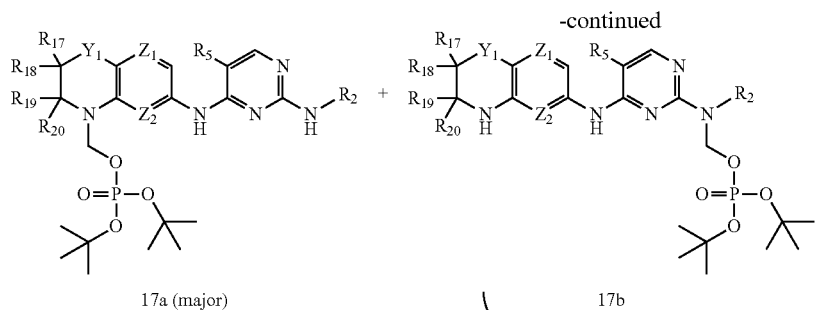
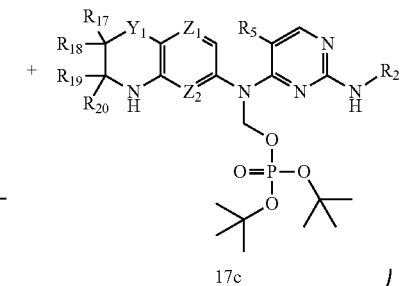

According to Scheme (V), the reaction of active 2,4-pyrimidinediamine 10 again yields a mixture of four products: unreacted pyrimidinediamine 10 (not illustrated) major product 17a and minor products 17b and 17c. Major product 17a can be isolated via crystallization (see the Examples section for suitable conditions), dissolved in a mixture of acetic acid and water (4:1 AcOH:$H_2O$) and heated to 65° C. for approximately 3 hr to yield phosphate prodrug 16 as the major product.

Figure 3:
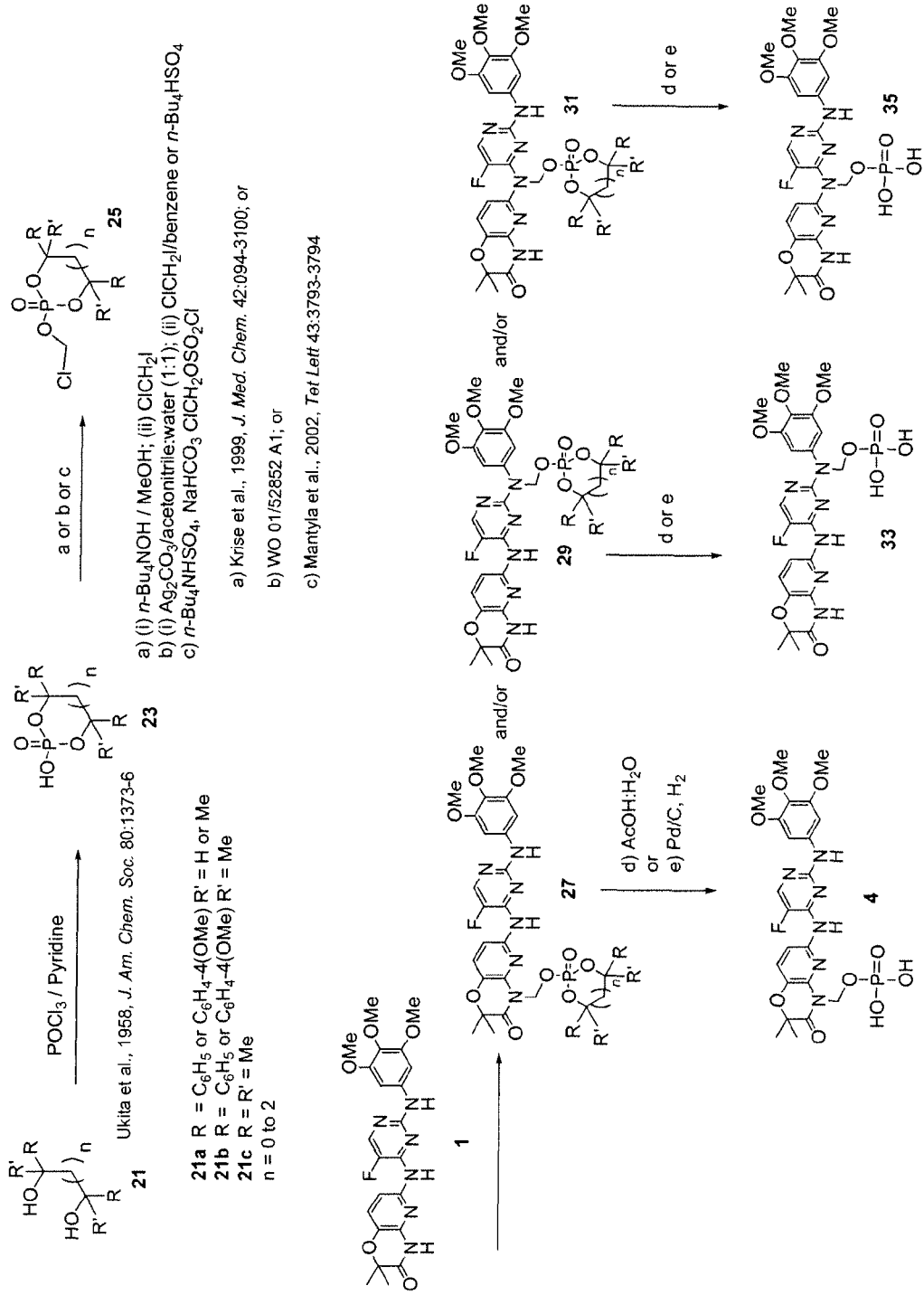
FIG. 3 illustrates an exemplary synthesis of exemplary cyclic phosphate prodrug.

Although Schemes (IV) and (V) illustrate the synthesis of a phosphate prodrug in which the phosphate progroup is —$CH_2$—O—P(O)$(OH)_2$, skilled artisans will appreciate that phosphate prodrugs including other phosphate progroups could be readily obtained according to the same methods by using the appropriate reagent 13. Phosphate ester prodrugs, phosphite prodrugs and phosphite ester prodrugs can also be synthesized via routine adaptation of the methods using the appropriate phosphate ester, phosphite and phosphite ester halides 13. Exemplary methods for synthesizing cyclic phosphate ester prodrugs, which can be used as prodrugs in the various methods described herein, or converted into phosphate prodrugs, are illustrated in FIG. 3. Moreover, while Schemes (I) and (III) depict compound 16 as being the desired product, prodrugs having progroups at other positions within the prodrug molecule could be readily obtained by isolating, for example minor product 17a or 17b and/or by adjusting the number of equivalents of reagent 13 used.

Referring to FIG. 3, diols 21 are converted to the corresponding cyclic phosphates 23 using literature procedures as depicted. Cyclic phosphates 23 are converted to the corresponding chloromethyl phosphate esters 25 in any of the three ways depicted. Compound 1 is converted to cyclic phosphate ester derivatives 27, 29, and 31, via addition of 25 under conditions as previously described for the synthesis of compounds 17a-c. Cyclic phosphate ester derivatives 27, 29, and 31, are converted to the corresponding phosphate derivatives via treatment under acidic conditions as described for the synthesis of compound 16, or via hydrogenation using, for example, palladium catalyst.

Prodrug salts may be prepared in a variety of ways familiar to the skilled artisan, or according to the methods described herein. For example, a prodrug bearing an acidic prodrug group $R^p$ may be converted to the corresponding prodrug salt by treatment with a base, followed by isolation through, for example, concentration, precipitation, or crystallization. If there exists more than one acidic hydrogen in the prodrug, then polyanionic salts may be prepared with the appropriate stoichiometric ratio of base and prodrug. For example, a dianion may be formed from a prodrug containing a —P(O)$(OH)_2$ group with two equivalents of an appropriate base. Preferred salts of prodrugs of the invention include, but are not limited to, sodium, potassium, calcium, magnesium, ammonium, and the like. Alternatively, an organic base may be used to prepare salts of the prodrugs of the invention. Examples of preferred organic bases include, but are not limited to, lysine, arginine, N,N-diethylethanolamine, diethanolamine, ethanolamine, ethylenediamine, meglumine, morpholine, piperazine, piperidine, triethylamine, tromethamine (Tris), benzathine, benzene-ethanamine, adenine, cytosine and guanidine. As described in more detail below, the prodrug salts may be formed in aqueous solution. Alternatively, they may be made in organic solution using an organic base such as sodium methoxide.

The cation may be exchanged by treating a solution of the desired prodrug anion with an appropriate cationic species to form an insoluble salt. The prodrug salt may be further purified by recrystallization or drying in vacuo. Prodrug salt hydrates may be prepared, for example, by salt formation, isolation, or recrystallization from aqueous solution.

Skilled artisans will recognize that in some instances, the active 2,4-pyrimidinediamine compounds used as starting materials may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, may be found, for example, in Greene & Wuts, *Protective Groups in Organic Synthesis*, 3d Edition, John Wiley & Sons, Inc., New York (1999) and the references cited therein (hereinafter "Greene & Wuts").

Inhibition of Fc Receptor Signal Cascades

Many of the prodrugs described herein, and in particular the prodrugs according to structural formulae (I) and (Ia), metabolize to active 2,4-pyrimidinediamine compounds that inhibit Fc receptor signaling cascades that lead to, among other things, degranulation of cells. As a specific example, these active compounds inhibit the FcϵRI and/or FcγRI signal cascades that lead to degranulation of immune cells such as neutrophil, eosinophil, mast and/or basophil cells. Both mast and basophil cells play a central role in allergen-induced disorders, including, for example, allergic rhinitis and asthma. Upon exposure allergens, which may be, among other things, pollen or parasites, allergen-specific IgE antibodies are synthesized by B-cells activated by IL-4 (or IL-13) and other messengers to switch to IgE class specific antibody synthesis. These allergen-specific IgEs bind to the high affinity FcϵRI. Upon binding of antigen, the FcϵR1-bound IgEs are cross-linked and the IgE receptor signal transduction pathway is activated, which leads to degranulation of the cells and consequent release and/or synthesis of a host of chemical mediators, including histamine, proteases (e.g., tryptase and chymase), lipid mediators such as leukotrienes (e.g., LTC4), platelet-activating factor (PAF) and prostaglandins (e.g., PGD2) and a series of cytokines, including TNF-α, IL-4, IL-13, IL-5, IL-6, IL-8, GMCSF, VEGF and TGF-β. The release and/or synthesis of these mediators from mast and/or basophil cells accounts for the early and late stage responses induced by allergens, and is directly linked to downstream events that lead to a sustained inflammatory state.

The molecular events in the FcϵRI signal transduction pathway that lead to release of preformed mediators via degranulation and release and/or synthesis of other chemical mediators are well-known. The FcϵRI is a heterotetrameric receptor composed of an IgE-binding alpha-subunit, a beta subunit, and two gamma subunits (gamma homodimer). Cross-linking of FcϵRI-bound IgE by multivalent binding agents (including, for example IgE-specific allergens or anti-IgE antibodies or fragments) induces the rapid association and activation of the Src-related kinase Lyn. Lyn phosphorylates immunoreceptor tyrosine-based activation motifs (ITAMS) on the intracellular beta and gamma subunits, which leads to the recruitment of additional Lyn to the beta subunit and Syk kinase to the gamma homodimer. These receptor-associated kinases, which are activated by intra- and intermolecular phosphorylation, phosphorylate other components of the pathway, such as the Btk kinase, LAT, and phospholipase C-gamma PLC-gamma). Activated PLC-gamma initiates pathways that lead to protein kinase C activation and Ca$^{2+}$ mobilization, both of which are required for degranulation. FcϵR1 cross-linking also activates the three major classes of mitogen activated protein (MAP) kinases, i.e. ERK1/2, JNK1/2, and p38. Activation of these pathways is important in the transcriptional regulation of proinflammatory mediators, such as TNF-α and IL-6, as well as the lipid mediator leukotriene C4 (LTC4).

The FcγRI signaling cascade is believed to share some common elements with the FcϵRI signaling cascade. Importantly, like FcϵRI, the FcγRI includes a gamma homodimer that is phosphorylated and recruits Syk, and like FcϵRI, activation of the FcγRI signaling cascade leads to, among other things, degranulation. Other Fc receptors that share the gamma homodimer, and which can be regulated by the active 2,4-pyrimidinediamine compounds include, but are not limited to, FcαRI and FcγRIII.

In vitro and cellular assays suitable for confirming the activity of a particular 2,4-pyrimidinediamine compound are described in detail in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003 (US 2005/0028212), international application Serial No. PCT/US03/24087 (WO2004/014382), U.S. application Ser. No. 10/903,263 filed Jul. 30, 2004 (US2005/0234049), and international application Serial No. PCT/US2004/24716 (WO 2005/016893).

The ability of a particular prodrug to metabolize to an active 2,4-pyrimidinediamine compound under the desired conditions of use can be confirmed in in vitro and/or in vivo assays, as previously described.

Uses and Compositions

As previously discussed, the prodrugs and prodrug salts described herein, such as those according to structural formulae (I), (Ia), (IX) and (IXa) metabolize when administered to animals and humans into active compounds that inhibit Fc receptor signaling cascades, especially those Fc receptors including a gamma homodimer, such as the FcϵRI and/or FcγRI signaling cascades, that lead to, among other things, the release and/or synthesis of chemical mediators from cells, either via degranulation or other processes. As also discussed, the active compounds are also potent inhibitors of Syk kinase. As a consequence of these activities, prodrugs of these active compounds may be used in a variety of in vitro, in vivo and ex vivo contexts to regulate or inhibit Syk kinase, signaling cascades in which Syk kinase plays a role, Fc receptor signaling cascades, and the biological responses effected by such signaling cascades. For example, in one embodiment, the prodrugs and prodrug salts may be used to inhibit Syk kinase, either in vitro or in vivo, in virtually any cell type expressing Syk kinase. They may also be used to regulate signal transduction cascades in which Syk kinase plays a role. Such Syk-dependent signal transduction cascades include, but are not limited to, the FcϵRI, FcγRI, FcγRIII, BCR and integrin signal transduction cascades. The prodrugs and prodrug salts may also be used in vitro or in vivo to regulate, and in particular inhibit, cellular or biological responses effected by such Syk-dependent signal transduction cascades. Such cellular or biological responses include, but are not limited to, respiratory burst, cellular adhesion, cellular degranulation, cell spreading, cell migration, cell aggregation, phagocytosis, cytokine synthesis and release, cell maturation and Ca$^{2+}$ flux. Importantly, the prodrugs and prodrug salts may be used to inhibit Syk kinase in vivo as a therapeutic approach towards the treatment or prevention of diseases mediated, either wholly or in part, by a Syk kinase activity. Non-limiting examples of Syk kinase mediated diseases that may be treated or prevented with the prodrugs and prodrug salts are those discussed in more detail, below.

In another embodiment, the prodrugs and prodrug salts may be used to regulate or inhibit the Fc receptor signaling cascades and/or FcεRI- and/or FcγRI-mediated degranulation as a therapeutic approach towards the treatment or prevention of diseases characterized by, caused by and/or associated with the release or synthesis of chemical mediators of such Fc receptor signaling cascades or degranulation. Such treatments may be administered to animals in veterinary contexts or to humans. Diseases that are characterized by, caused by or associated with such mediator release, synthesis or degranulation, and that can therefore be treated or prevented with the active compounds include, by way of example and not limitation, atopy or anaphylactic hypersensitivity or allergic reactions, allergies (e.g., allergic conjunctivitis, allergic rhinitis, atopic asthma, atopic dermatitis and food allergies), low grade scarring (e.g., of scleroderma, increased fibrosis, keloids, post-surgical scars, pulmonary fibrosis, vascular spasms, migraine, reperfusion injury and post myocardial infarction), diseases associated with tissue destruction (e.g., of COPD, cardiobronchitis and post myocardial infarction), diseases associated with tissue inflammation (e.g., irritable bowel syndrome, spastic colon and inflammatory bowel disease), inflammation and scarring.

Recent studies have shown that activation of platelets by collagen is mediated through the same pathway used by immune receptors, with an immunoreceptor tyrosine kinase motif on the FcRγ playing a pivotal role (Watson & Gibbons, 1998, Immunol. Today 19:260-264), and also that FcRγ plays a pivotal role in the generation of neointimal hyperplasia following balloon injury in mice, most likely through collagen-induced activation of platelets and leukocyte recruitment (Konishi et al., 2002, Circulation 105:912-916). Thus, the prodrugs described herein can also be used to inhibit collagen-induced platelet activation and to treat or prevent diseases associated with or caused by such platelet activation, such as, for example, intimal hyperplasia and restenosis following vascular injury.

In addition to the myriad diseases discussed above, cellular and animal empirical data confirm that the active 2,4-pyrimidinediamine compounds described in U.S. application Ser. No. 10/631,029 filed Jul. 29, 2003 (US 2005/0028212), international application Serial No. PCT/US03/24087 (WO2004/014382), U.S. application Ser. No. 10/903,263 filed Jul. 30, 2004 (US2005/0234049), and international application Serial No. PCT/US2004/24716 (WO 2005/016893) are also useful for the treatment or prevention of autoimmune diseases, as well as the various symptoms associated with such diseases. Thus, prodrugs and prodrug salts of these active compounds are useful for treating or preventing such diseases and/or symptoms. The types of autoimmune diseases that may be treated or prevented with such prodrugs generally include those disorders involving tissue injury that occurs as a result of a humoral and/or cell-mediated response to immunogens or antigens of endogenous and/or exogenous origin. Such diseases are frequently referred to as diseases involving the nonanaphylactic (i.e., Type II, Type III and/or Type IV) hypersensitivity reactions.

As discussed previously, Type I hypersensitivity reactions generally result from the release of pharmacologically active substances, such as histamine, from mast and/or basophil cells following contact with a specific exogenous antigen. As mentioned above, such Type I reactions play a role in numerous diseases, including allergic asthma, allergic rhinitis, etc.

Type II hypersensitivity reactions (also referred to as cytotoxic, cytolytic complement-dependent or cell-stimulating hypersensitivity reactions) result when immunoglobulins react with antigenic components of cells or tissue, or with an antigen or hapten that has become intimately coupled to cells or tissue. Diseases that are commonly associated with Type II hypersensitivity reactions include, but are not limited, to autoimmune hemolytic anemia, erythroblastosis fetalis and Goodpasture's disease.

Type III hypersensitivity reactions, (also referred to as toxic complex, soluble complex, or immune complex hypersensitivity reactions) result from the deposition of soluble circulating antigen-immunoglobulin complexes in vessels or in tissues, with accompanying acute inflammatory reactions at the site of immune complex deposition. Non-limiting examples of prototypical Type III reaction diseases include the Arthus reaction, rheumatoid arthritis, serum sickness, systemic lupus erythematosis, certain types of glomerulonephritis, multiple sclerosis and bullous pemphingoid.

Type IV hypersensitivity reactions (frequently called cellular, cell-mediated, delayed, or tuberculin-type hypersensitivity reactions) are caused by sensitized T-lymphocytes which result from contact with a specific antigen. Non-limiting examples of diseases cited as involving Type IV reactions are contact dermatitis and allograft rejection.

Autoimmune diseases associated with any of the above nonanaphylactic hypersensitivity reactions may be treated or prevented with the prodrugs and prodrug salts according to structural formulae (I), (Ia), (IX) and (IXa). In particular, the methods may be used to treat or prevent those autoimmune diseases frequently characterized as single organ or single cell-type autoimmune disorders including, but not limited to: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, as well as those autoimmune diseases frequently characterized as involving systemic autoimmune disorder, which include but are not limited to: systemic lupus erythematosis (SLE), rheumatoid arthritis, Sjogren's syndrome, Reiter's syndrome, polymyositis-dermatomyositis, systemic sclerosis, polyarteritis nodosa, multiple sclerosis and bullous pemphigoid.

It will be appreciated by skilled artisans that many of the above-listed autoimmune diseases are associated with severe symptoms, the amelioration of which provides significant therapeutic benefit even in instances where the underlying autoimmune disease may not be ameliorated. Many of these symptoms, as well as their underlying disease states, result as a consequence of activating the FcγR signaling cascade in monocyte cells. As the prodrugs of structural formulae (I), (Ia), (IX) and (IXa) metabolize to 2,4-pyrimidinediamine compounds that are potent inhibitors of such FcγR signaling in monocytes and other cells, the methods find use in the treatment and/or prevention of myriad adverse symptoms associated with the above-listed autoimmune diseases.

As a specific example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The methods may be used to treat or ameliorate any one, several or all of these symptoms of RA. Thus, in the context of RA, the methods are considered to provide therapeutic benefit (discussed more generally, infra) when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria includes Paulu's criteria and radiographic progression (e.g. Sharp score).

In some embodiments, therapeutic benefit in patients suffering from RA is achieved when the patient exhibits an ARC20. In specific embodiments, ARCs of ARC50 or even ARC70 may be achieved.

Systemic lupus erythematosis ("SLE") is typically associated with symptoms such as fever, joint pain (arthralgias), arthritis, and serositis (pleurisy or pericarditis). In the context of SLE, the methods are considered to provide therapeutic benefit when a reduction or amelioration of any of the symptoms commonly associated with SLE are achieved, regardless of whether the treatment results in a concomitant treatment of the underlying SLE.

Multiple sclerosis ("MS") cripples the patient by disturbing visual acuity; stimulating double vision; disturbing motor functions affecting walking and use of the hands; producing bowel and bladder incontinence; spasticity; and sensory deficits (touch, pain and temperature sensitivity). In the context of MS, the methods are considered to provide therapeutic benefit when an improvement or a reduction in the progression of any one or more of the crippling effects commonly associated with MS is achieved, regardless of whether the treatment results in a concomitant treatment of the underlying MS.

When used to treat or prevent such diseases, the prodrugs and prodrug salts described herein may be administered singly, as mixtures of one or more prodrugs and prodrug salts or in mixture or combination with other agents useful for treating such diseases and/or the symptoms associated with such diseases. The prodrugs and prodrug salts may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The prodrugs and prodrug salts may be administered in the form of compounds per se, or as pharmaceutical compositions comprising a prodrug.

Another aspect of the invention relates to pharmaceutical compositions of the prodrugs, prodrug salts, prodrug salt hydrates, and crystals thereof as described herein. Accordingly, one embodiment of the invention provides a pharmaceutical composition comprising a prodrug, prodrug salt, prodrug salt hydrate or crystal, and a pharmaceutically-acceptable carrier, excipient and/or diluent. The prodrug, prodrug salt, prodrug salt hydrate or crystal may be made, for example, by any of the methods described herein. Preferably, the mole ratio of the prodrug, prodrug salt, prodrug salt hydrate, or crystal to the corresponding drug compound is greater than about 18:1. For example, when the pharmaceutical composition includes the prodrug salt hydrate

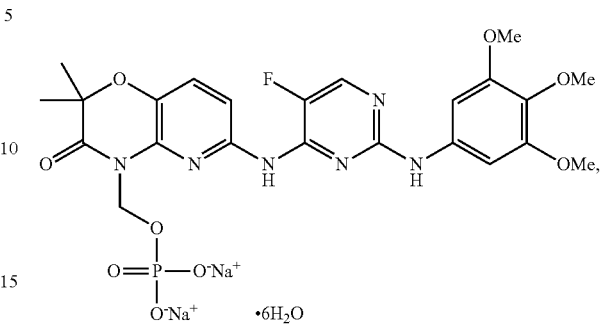

the pharmaceutical composition has a mole ratio of prodrug salt hydrate to the corresponding drug compound

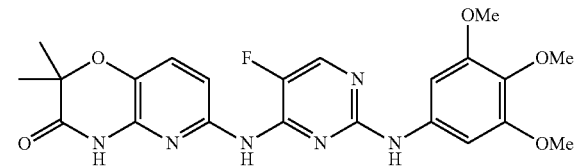

of at least about 10:1. Preferably, the ratio is at least about 18:1.

Pharmaceutical compositions comprising the prodrug(s) and prodrug salt(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the prodrugs into preparations which can be used pharmaceutically.

The prodrug may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the prodrug(s) and prodrug salt(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings. Phosphate prodrugs in which the progroup(s) is of the formula —$(CR^dR^d)_y$—O—$P(O)(OH)_2$, and certain phosphate prodrug salts in which the progroup(s) is of the formula —$(CR^dR^d)_y$—O—$P(O)(O^-)_2[M^+]_2$ or —$(CR^dR^d)_y$—O—$P(O)(OH)(O^-)[M^+]$, where each $R^d$ is, independently of the others, selected from hydrogen and lower alkyl and y is 1 or 2 and that exhibit a water-solubility in the range of about 0.1 to 1000 mg/ml at physiological pH are especially suited for oral administration via tablets and capsules. When administered to Sprague-Dawley rats orally from capsules, prodrug Compound 4 exhibits a bioavailability of drug Compound 1 of about 30% (see FIG. 5), with absorption being nearly identical to that of active drug Compound 1 (see FIG. 6). Other phosphate prodrugs and prodrug salts having water-solubility properties similar to those of prodrug Compound 4 are expected to exhibit similar pharmacokinetic properties.

A specific exemplary tablet formulation for prodrug Compound 4 (as well as other phosphate-containing prodrugs) contains about 50-400 mg prodrug compound (or a salt thereof), about 0.05 to 0.5 wt % colloidal silicon dioxide, about 0.5 to 5.0 wt % croscarmellose sodium, about 0.25 to 5.0 wt % magnesium stearate and about 20 to 80 wt % microcrystalline cellulose. If desired, the tablets can be coated with a film, such as a hypromellose film carboxymethyl cellulose or fructose, which can optionally contain coloring agents, such as for example FD&C blue #1, PD&C green #3, FD&C yellow #6 and titanium dioxide.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, CREMOPHORE™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the prodrug or prodrug salt, as is well known.

For buccal administration, the compositions may take the form of tablets or lozenges formulated in conventional manner.

For rectal and vaginal routes of administration, the prodrug(s) or prodrug salt(s) may be formulated as solutions (for retention enemas) suppositories or ointments containing conventional suppository bases such as cocoa butter or other glycerides.

For nasal administration or administration by inhalation or insufflation, the prodrug(s) or prodrug salt(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the prodrug(s) or prodrug salt(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the prodrug(s) or prodrug salt(s) can be formulated as a depot preparation for administration by implantation or intramuscular injection. The prodrug(s) or prodrug salt(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the prodrug(s) or prodrug salt(s) for percutaneous absorption may be used. To this end, permeation enhancers may be used to facilitate transdermal penetration of the prodrug(s) or prodrug salt(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems may be employed. Liposomes and emulsions are well-known examples of delivery vehicles that may be used to deliver prodrug(s) or prodrug salt(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the prodrug(s) or prodrug salt(s). The pack may, for example, comprise metal or plastic foil, such as a blister pack. The pack or dispenser device may be accompanied by instructions for administration.

Effective Dosages

The prodrug(s) or prodrug salt(s) described herein, or compositions thereof, will generally be used in an amount effective to achieve the intended result, for example in an amount effective to treat or prevent the particular disease being treated. The prodrug(s) or prodrug salt(s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit in the context of RA also includes the ACR20, or ACR50 or ACR70, as previously described. Therapeutic benefit also generally includes halting or slowing the progression of the disease, regardless of whether improvement is realized.

For prophylactic administration, the prodrug(s) or prodrug salt(s) may be administered to a patient at risk of developing one of the previously described diseases. For example, if it is unknown whether a patient is allergic to a particular drug, the prodrug(s) or prodrug salt(s) may be administered prior to administration of the drug to avoid or ameliorate an allergic response to the drug. Alternatively, prophylactic administration may be applied to avoid the onset of symptoms in a patient diagnosed with the underlying disorder. For example, the prodrug(s) or prodrug salt(s) may be administered to an allergy sufferer prior to expected exposure to the allergen. Prodrug(s) or prodrug salt(s) may also be administered prophylactically to healthy individuals who are repeatedly exposed to agents known to one of the above-described maladies to prevent the onset of the disorder. For example, prodrug(s) or prodrug salt(s) may be administered to a healthy individual who is repeatedly exposed to an allergen known to induce allergies, such as latex, in an effort to prevent the individual from developing an allergy. Alternatively, prodrug(s) or prodrug salt(s) may be administered to a patient suffering from asthma prior to partaking in activities which trigger asthma attacks to lessen the severity of, or avoid altogether, an asthmatic episode.

The amount of prodrug(s) or prodrug salt(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular prodrug(s) or prodrug salt(s) the conversation rate and efficiency into active drug compound under the selected route of administration, etc. Determination of an effective dosage of prodrug(s) or prodrug salt(s) for a particular use and mode of administration is well within the capabilities of those skilled in the art.

Effective dosages may be estimated initially from in vitro activity and metabolism assays. For example, an initial dosage of prodrug or prodrug salt for use in animals may be formulated to achieve a circulating blood or serum concentration of the metabolite active compound that is at or above an $IC_{50}$ of the particular compound as measured in as in vitro assay, such as the in vitro CHMC or BMMC and other in vitro assays described in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003 (US 2005/0028212), international application Serial No. PCT/US03/24087 (WO2004/014382), U.S. application Ser. No. 10/903,263 filed Jul. 30, 2004 (US2005/0234049), and international application Serial No. PCT/US2004/24716 (WO 2005/016893). Calculating dosages to achieve such circulating blood or serum concentrations taking into account the bioavailability of the particular prodrug via the desired route of administration is well within the capabilities of skilled artisans. For guidance, the reader is referred to Fingl & Woodbury, "General Principles," In: *Goodman and Gilman's The Pharmaceutical Basis of Therapeutics*, Chapter 1, pp. 1-46, latest edition, Pagamonon Press, and the references cited therein.

Initial dosages of prodrug or prodrug salt can also be estimated from in vivo data, such as animal models. Animal models useful for testing the efficacy of the active metabolites to treat or prevent the various diseases described above are well-known in the art. Suitable animal models of hypersensitivity or allergic reactions are described in Foster, 1995, Allergy 50(21Suppl):6-9, discussion 34-38 and Tumas et al., 2001, J. Allergy Clin. Immunol. 107(6):1025-1033. Suitable animal models of allergic rhinitis are described in Szelenyi et al., 2000, Arzneimittelforschung 50(11):1037-42; Kawaguchi et al., 1994, Clin. Exp. Allergy 24(3):238-244 and Sugimoto et al., 2000, Immunopharmacology 48(1):1-7. Suitable animal models of allergic conjunctivitis are described in Carreras et al., 1993, Br. J. Ophthalmol. 77(8):509-514; Saiga et al., 1992, Ophthalmic Res. 24(1):45-50; and Kunert et al., 2001, Invest. Ophthalmol. Vis. Sci. 42(11):2483-2489. Suitable animal models of systemic mastocytosis are described in O'Keefe et al., 1987, J. Vet. Intern. Med. 1(2):75-80 and Bean-Knudsen et al., 1989, Vet. Pathol. 26(1):90-92. Suitable animal models of hyper IgE syndrome are described in Claman et al., 1990, Clin. Immunol. Immunopathol. 56(1):46-53. Suitable animal models of B-cell lymphoma are described in Hough et al., 1998, Proc. Natl. Acad. Sci. USA 95:13853-13858 and Hakim et al., 1996, J. Immunol. 157(12):5503-5511. Suitable animal models of atopic disorders such as atopic dermatitis, atopic eczema and atopic asthma are described in Chan et al., 2001, J. Invest. Dermatol. 117(4): 977-983 and Suto et al., 1999, Int. Arch. Allergy Immunol. 120(Suppl 1):70-75. Animal models suitable for testing the bioavailability and/or metabolism of prodrugs into active metabolites are also well-known. Ordinarily skilled artisans can routinely adapt such information to determine dosages of particular prodrugs and prodrug salts suitable for human administration. Additional suitable animal models are described in the Examples section.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active metabolite compound, the bioavailability of the prodrug or prodrug salt, its metabolism kinetics and other pharmacokinetic properties, the mode of administration and various other factors, discussed above. Dosage amount and interval may be adjusted individually to provide plasma levels of the prodrug(s), prodrug salt(s) and/or active metabolite compound(s) which are sufficient to maintain therapeutic or prophylactic effect. For example, the prodrugs may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of prodrug(s), prodrug salt(s) and/or active metabolite compound(s) may not be related to plasma concentration. Skilled artisans will be able to optimize effective local dosages without undue experimentation.

Preferably, the prodrugs will metabolize into active compound(s) that will provide therapeutic or prophylactic benefit without causing substantial toxicity. Toxicity of the active and other metabolites, as well as the unmetabolized prodrug may be determined using standard pharmaceutical procedures. The dose ratio between toxic and therapeutic (or prophylactic) effect is the therapeutic index. Prodrug(s) and prodrug salt(s) that exhibit high therapeutic indices are preferred.

The inventions having been described, the following examples are offered by way of illustration and not limitation.

EXAMPLES

1. Synthesis of Prodrug Compound 4

1.1 N4-(2,2-dimethyl-4-[(di-tert-butyl phosphonoxy) methyl]-3-oxo-5-pyrido[1,4]oxazin-6-yl)-5-fluoro-N2-(3,4,5-trimethoxyphenyl)-2,4-pyrimidinediamine (Compound 3)

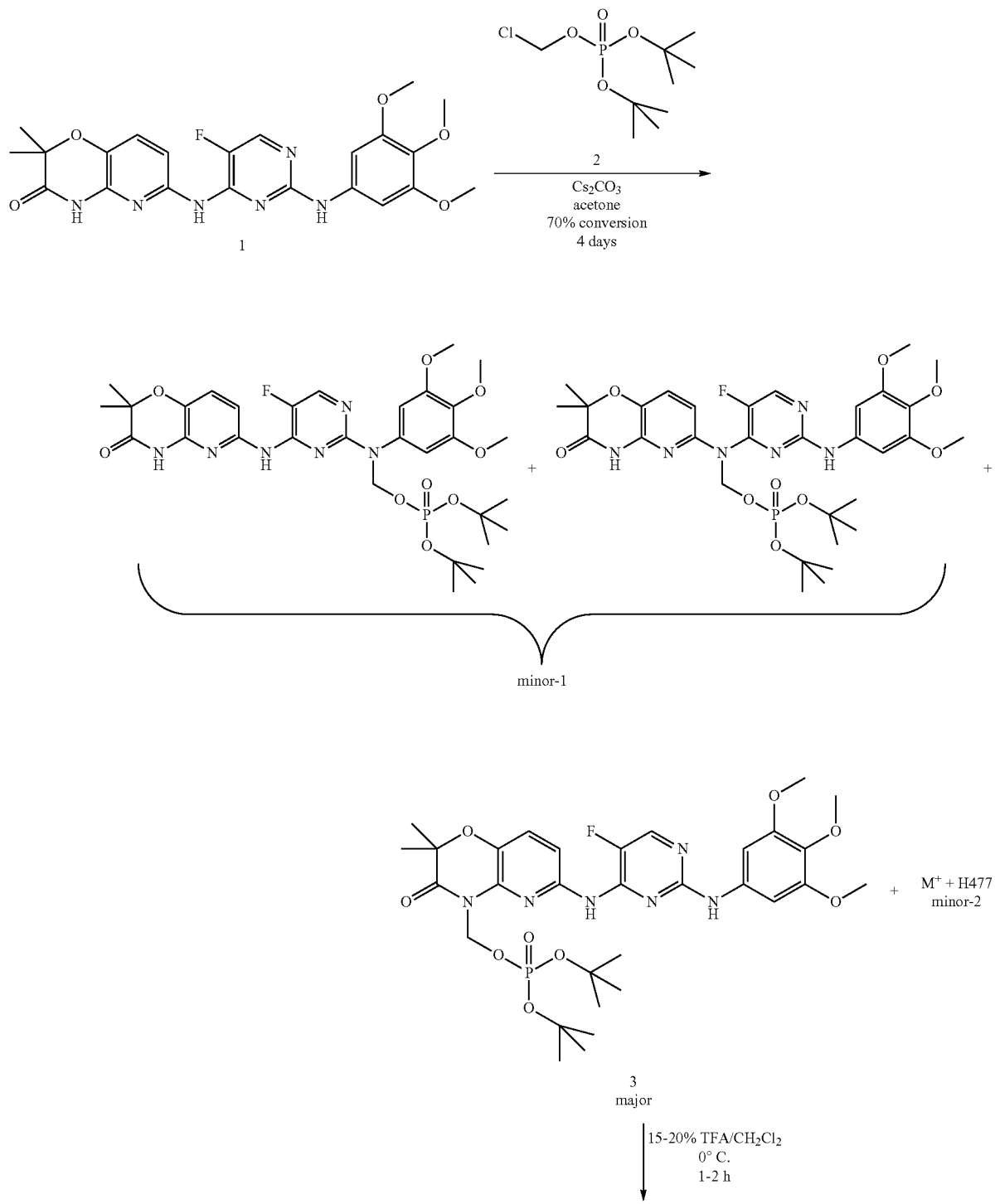

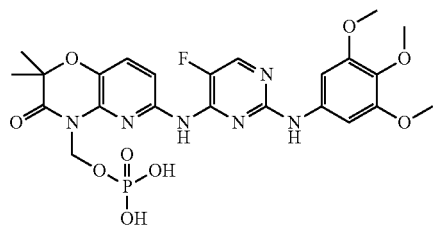
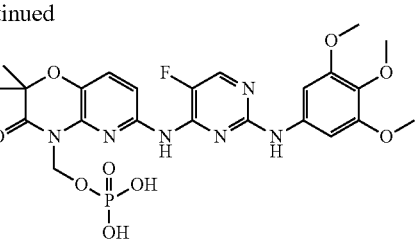

N4-(2,2-dimethyl-3-oxo-4H-5-pyrido[1,4]oxazin-6-yl)-5-fluoro-N2-(3,4,5-trimethoxyphenyl)-2,4-pyrimidinediamine (1, 1.0 g, 2.12 mmol), $Cs_2CO_3$ (1.0 g, 3.07 mmol) and di-tent-butyl chloromethyl phosphate (2, 0.67 g, 2.59 mmol) in acetone (20 mL) was stirred at room temperature under nitrogen atmosphere. Progress of the reaction was monitored by LC/MS. Crude reaction mixture displayed three product peaks with close retention times with $M^{30}+H$ 693 (minor-1), 693 (major; 3) and 477 (minor-2) besides starting material (Compound 1). Upon stirring the contents for 4 days (70% consumption), the reaction mixture was concentrated and diluted with water. The resultant pale yellow precipitate formed was collected by filtration and dried. The crude solid was purified by silica gel (pretreated with 10%$NEt_3$/$CH_2Cl_2$ followed by eluting with hexanes) column chromatography by gradient elution with 70% EtOAc/hexanes-100% EtOAc). The fractions containing Compound 1 and $M^++H$ 693 were collected and concentrated. The resulting crude white solid was subjected to repurification in the similar manner as described previously but by eluting with 30%-50%-75%-100% EtOAc/hexanes. The major product peak with $M^++H$ 693 was collected as a white solid (270 mg, 18%) and was characterized as N4-(2,2-dimethyl-4-[(di-tert-butyl phosphonoxy)methyl]-3-oxo-5-pyrido[1,4]oxazin-6-yl)-5-fluoro-N2-(3,4,5-trimethoxyphenyl)-2,4-pyrimidinediamine (Compound 3). $^1$H NMR (DMSO-d6): δ 9.21 (s, 1H), 9.17 (s, 1H), 8.16 (d, 1H, J=2.6 Hz), 7.76 (d, 1H, J=8.5 Hz), 7.44 (d, 1H, J=8.5 Hz), 7.02 (s, 2H), 5.78 (d, 1H, $J^3_{PH}$=6.1 Hz), 3.64 (s, 6H), 3.58 (s, 3H), 1.45 (s, 6H), 1.33 (s, 9H). LCMS: ret. time: 14.70 min.; purity: 95%; MS (m/e): 693 (MH$^+$). $^{31}$P NMR (DMSO-d6): −11.36.

1.2. N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (Compound 4)

Trifluoroacetic acid (1.5 mL) was added dropwise as a neat for 5 min to N4-(2,2-dimethyl-4-[(di-tert-butyl phosphonoxy)methyl]-3-oxo-5-pyrido[1,4]oxazin-6-yl)-5-fluoro-N2-(3,4,5-trimethoxyphenyl)-2,4-pyrimidinediamine (Compound 3, 120 mg, 0.173 mmol) dissolved in $CH_2Cl_2$ (10 mL) at 0° C. under nitrogen atmosphere. The contents were allowed to stir for 1.5 h. Progress of the reaction mixture was monitored by LC/MS. After complete consumption of the starting material, reaction mixture was concentrated, dried and triturated with ether. The ethereal layer was decanted and dried to provide the crude solid. LC/MS analysis of the crude displayed three peaks with $M^++H$ 581, 471 and 501. The peak corresponding to $M^++H$ 581 was collected by preparative HPLC chromatographic purification. The fractions were lyophilised and dried to provide 53 mg (52%) of off white fluffy solid and characterized as N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (Compound 4). $^1$H NMR (DMSO-d6): δ 9.21 (br s, 2H), 8.16 (d, 1H, J=2.6 Hz), 7.93 (d, 1H, J=8.5 Hz), 7.39 (d, 1H, J=8.5 Hz), 7.05 (s, 2H), 5.79 (d, 1H, $J^3_{PH}$=6.6 Hz), 3.67 (s, 6H), 3.59 (s, 3H), 1.44 (s, 6H). LCMS: ret. time: 8.52 min.; purity: 95%; MS (m/e): 581 (MH$^-$). $^{31}$P NMR (DMSO-d6): −2.17.

2. Alternative Synthesis of Prodrug Compound 4

An alternative method of synthesizing prodrug Compound 4 which alleviates the need for column chromatography and HPLC purification is provided below.

2.1 Synthesis of N4-(2,2-dimethyl-4-[(di-tert-butyl phosphonoxy)methyl]-3-oxo-5-pyrido[1,4]oxazin-6-yl)-5-fluoro-N2-(3,4,5-trimethoxyphenyl)-2,4-pyrimidinediamine (Compound 3)

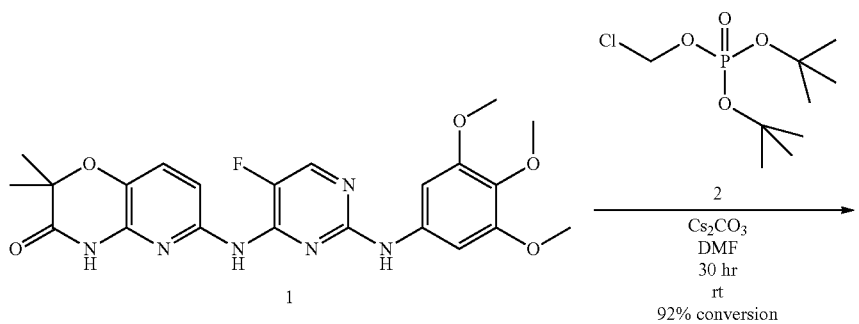

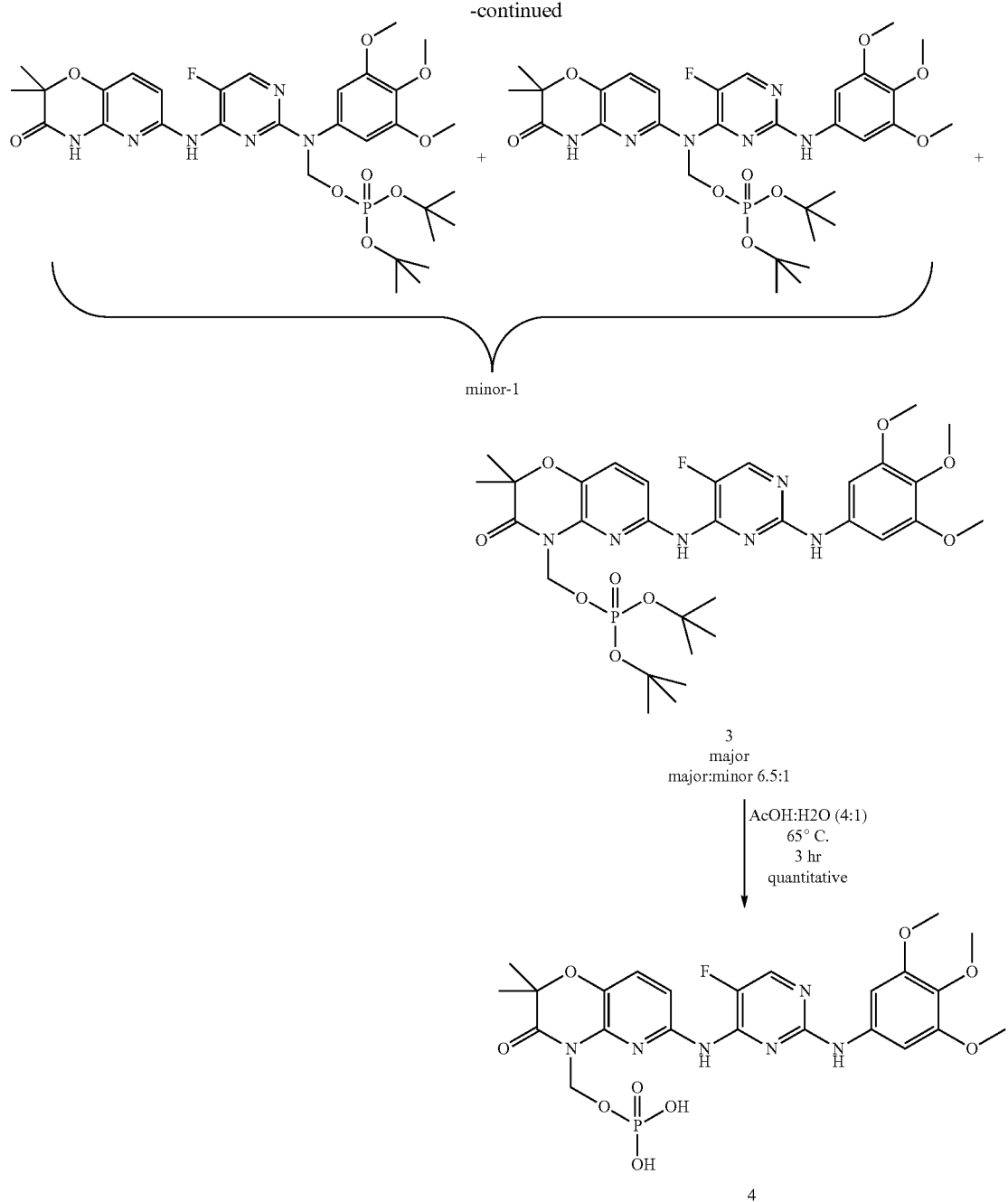

N4-(2,2-dimethyl-3-oxo-4H-5-pyrido[1,4]oxazin-6-yl)-5-fluoro-N2-(3,4,5-trimethoxyphenyl)-2,4-pyrimidinediamine (Compound 1, 19.73 g, 41.97 mmol), $Cs_2CO_3$ (15.04 g, 46.16 mmol) and di-tent-butyl chloromethyl phosphate (13.0 g, 50.38 mmol) in DMF (100 mL) was stirred at room temperature under nitrogen atmosphere. Progress of the reaction was monitored by in process LC/MS. Crude reaction mixture displayed two product peaks (ratio 1:6.5) with close retention times displaying $M^1$+H 693 (minor) and 693 (major) besides starting material (Compound 1). Initial yellow reaction mixture turned to olive green as the reaction progressed. Workup was carried out as follows 1). Upon stirring the contents for 30 h (92% consumption), reaction mixture was poured onto ice-water (400 mL) and stirred the contents by adding brine solution (200 mL). Fine yellow tan solid formed was filtered, washed with water and dried overnight.

2). The solid (35 g) was dissolved in MTBE (500 mL) and washed with water (400 mL). Aqueous layer was extracted with MTBE (2×350 mL) till the absence of UV on TLC. Combined organic layers were dried over anhydrous $Na_2SO_4$ and decanted.

Note: step 2 can be done directly, however, DMF extraction back into solution leads to difficulty in the crystallization step.

3). The dark red clear solution was subjected to 10 g of activated charcoal treatment, heated to boil and filtered.

4). The dark red clear solution was concentrated by normal heating to 400 mL of its volume and left for crystallization. The solid crystallized as granules was filtered, crushed the granules to powder, washed with MTBE (400 mL) and dried under high vacuum. See step 7 for the workup of mother liquor. Weight of the solid: 17 g; purity: 90% (Compound 3), 6.26% (Compound 1), 1.8% (minor M+ 693).

5). At this stage solid was taken in 500 ml of ethyl ether and heated to boil. Cooled and filtered to remove undissolved material. Filtrate was concentrated.

6). Above concentrate was subjected to crystallization in MTBE (300 mL). The white solid formed was filtered, washed with MTBE (100 mL) and dried under high vacuum to provide the desired N4-(2,2-dimethyl-4-[(di-tert-butyl phosphonoxy)methyl]-3-oxo-5-pyrido[1,4]oxazin-6-yl)-5-fluoro-N2-(3,4,5-trimethoxyphenyl)-2,4-pyrimidinediamine (Compound 3) in 97% purity. $^1$H NMR (DMSO-d6): δ 9.21 (s, 1H), 9.17 (s, 1H), 8.16 (d, 1H, J=2.6 Hz), 7.76 (d, 1H, J=8.5 Hz), 7.44 (d, 1H, J=8.5 Hz), 7.02 (s, 2H), 5.78 (d, 1H, $J^3_{PH}$=6.1 Hz), 3.64 (s, 6H), 3.58 (s, 3H), 1.45 (s, 6H), 1.33 (s, 9H). LCMS: ret. time: 14.70 min.; purity: 95%; MS (m/e): 693 (MH$^+$). $^{31}$P NMR (DMSO-d6): −11.36. Weight of the solid: 15.64 g (yield: 55%); purity: 97% (Compound 3), 3% (Compound 1).

7). The mother liquor was concentrated and steps 5 and 6 were repeated to provide Compound 3.

2.2. Synthesis of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (Compound 4)

N4-(2,2-dimethyl-4-[(di-tert-butyl phosphonoxy)methyl]-3-oxo-5-pyrido[1,4]oxazin-6-yl)-5-fluoro-N2-(3,4,5-trimethoxyphenyl)-2,4-pyrimidinediamine (Compound 3); (15.0 g, 21.67 mmol) dissolved in AcOH:H$_2$O (225 mL, 4:1) was heated at 65° C. (oil bath temp). The progress of the reaction was monitored by in process LC/MS. The reaction mixture transformed to faint tan white solid after 1 h of heating. At this point most of Compound 3 converted to mono des t-butyl product. After 3 h of heating, consumption of SM and complete conversion of intermediate (mono des t-butylated) to product was observed.

Reaction mixture was cooled, poured onto ice-water (200 mL), stirred for 20 min and filtered. The clear white filter cake was washed with water (600 ml) and acetone (200 mL) successively, dried for 2 h followed by drying under high vacuum over P$_2$O$_5$ in a desiccator. Weight of the solid: 12.70 g; purity: 97% (Compound 3) and 3% (Compound 1) $^1$H NMR indicated acetic acid presence (1:1)

To remove acetic acid, the solid was taken in acetonitrile (300 mL) and concentrated by rotovap vacuum. This process was repeated 2 times with acetonitrile and toluene (3×300 mL). The solid obtained was dried under high vacuum at 50° C.

Finally, the solid was taken in acetone (400 mL), filtered and dried to provide solid N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (Compound 4). $^1$H NMR (DMSO-d6): δ 9.21 (br s, 2H), 8.16 (d, 1H, J=2.6 Hz), 7.93 (d, 1H, J=8.5 Hz), 7.39 (d, 1H, J=8.5 Hz), 7.05 (s, 2H), 5.79 (d, 1H, $J^3_{PH}$=6.6 Hz), 3.67 (s, 6H), 3.59 (s, 3H), 1.44 (s, 6H). LCMS: ret. time: 8.52 min.; purity: 95%; MS (m/e): 581 (MH$^-$). $^{31}$P NMR (DMSO-d6): −2.17.

3. Synthesis of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine mono calcium salt (Prodrug Salt 6)

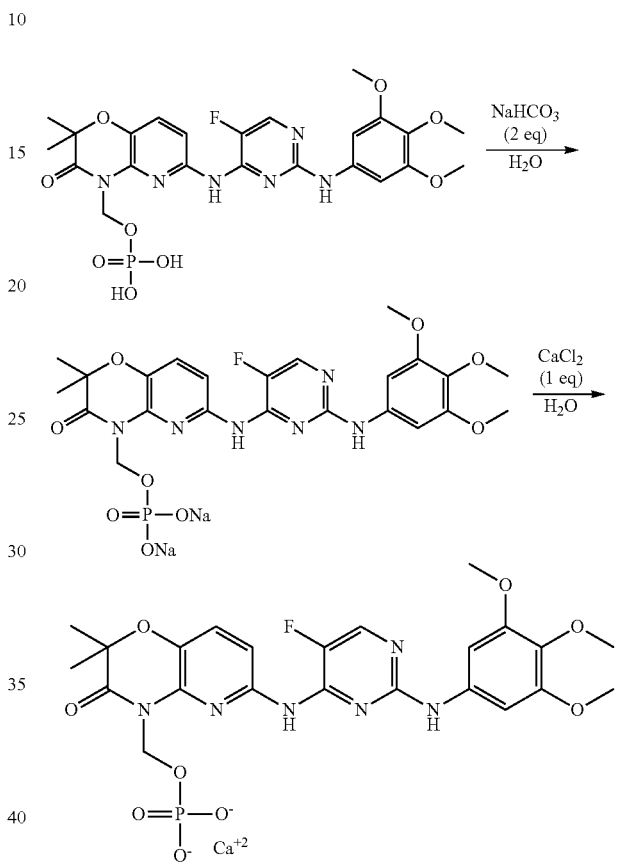

Aqueous (10 mL) NaHCO$_3$ (0.17 g, 2.02 mmol) solution was added dropwise to a suspension of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (0.5 g, 0.86 mmol) in water (5 mL) at room temperature while stirring the contents. The clear solution formed was treated with aqueous (10 mL) CaCl$_2$ (0.11 g in 10 mL water, 0.99 mmol) n a dropwise manner at room temperature. The addition resulted in the precipitation of a white solid from reaction mixture. Upon completion of addition, the contents were stirred for a period of 30 min, filtered, washed with water (40 mL) and dried. The clear white solid was taken in water (30 mL) and heated on a stir plate to boil. The solution was cooled, filtered and dried. The white solid collected and further dried under high vacuo at 80° C. for 32 h to provide 0.41 g (83%) of solid N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine mono calcium salt (Prodrug Salt 6).

Ca(OAc)$_2$ may also used in place of CaCl$_2$ in this preparation.

4. Synthesis of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine disodium salt hexahydrate and monosodium salt hydrate

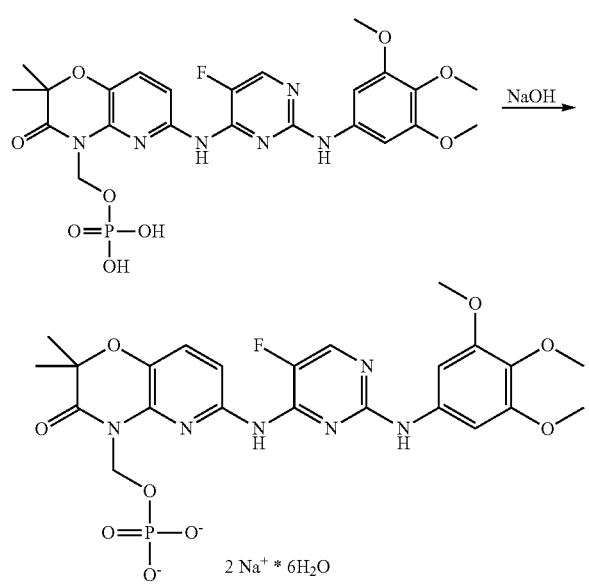

A round-bottomed flask was charged with 10.00 g N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (Compound 4) and 140 mL water into a round bottom flask to form a slurry having a pH between 3.6 and 3.7. The pH was adjusted to in the range of 9.3 to 10.3 by addition of 1 M aqueous NaOH, initially forming a turbid solution, which returned to a suspension upon prolonged stirring. The mixture was heated at reflux, then the turbid solution was hot filtered through filter paper. The solid collected in the filter paper was rinsed with 10 mL hot water. Isopropanol (75 mL) was added to the filtrate, yielding a clear solution, which was allowed to cool to room temperature over about 1.5 hours with stirring, during which time a solid precipitated. The precipitate was collected by filtration, rinsed with 47 mL isopropanol, and taken up in 73 mL acetone to form a slurry, which was stirred for 1.5 hours at room temperature. The solid was again collected by filtration and rinsed with 18 mL acetone, then dried at about 40° C. under vacuum until substantially all isopropanol and acetone was removed (i.e., below 0.5 wt % each). The product was exposed to air at about 40% relative humidity and room temperature until the water content stabilized at about 15% by Karl Fisher titration, yielding 8.18 g of the title compound. $^1$H NMR (D$_2$O): δ 7.67 (d, 1H, J=3.8 Hz), 7.49 (d, 1H, J=8.8 Hz), 6.87 (d, 1H, J=8.8 Hz), 6.50 (s, 2H), 5.52 (d, 1H, $J^3_{PH}$=2.0 Hz), 3.53 (s, 3H), 3.47 (s, 6H), 1.32 (s, 6H). $^{31}$P NMR (D$_2$O): 2.75. The prodrug salt hydrate was obtained as a pure-white, highly crystalline material. Microscopic investigation indicated that the crystallites are plate-like with a particle size of less than 10 μm. Polarized light microscopy revealed birefringence corroborating the crystalline nature of the hydrate.

The monosodium salt can be prepared from N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine and sodium hydroxide by a proper pH control; pH of 5-5.5 results in predominantly the formation of monosodium salt.

5. Preparation of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine dipotassium salt

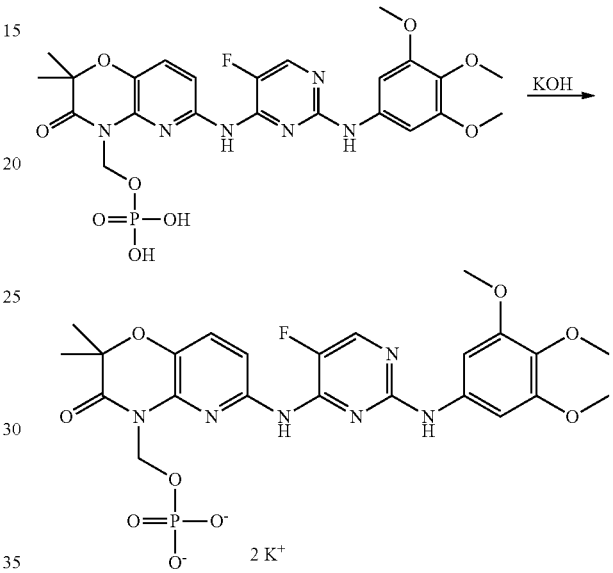

A suspension of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine, acetic acid complex (1.0 g, 1.56 mmol) in water (15 mL) was heated at 70° C. (oil bath temp) for 10 min (pH=2.9). To the above stirring suspension, aqueous KOH (2.1 M, 1.5 ml) was added dropwise and the pH was observed as 5.9. At this point 2.5 M aqueous KOH was added dropwise while monitoring the pH. When the pH reached to 10.5 (after 0.95 mL), addition was stopped and the clear solution stirred at the same temperature for 15 min. The warm solution was filtered into a conical flask and washed the filter paper with water to a combined volume of 45 mL. The filtrate was transferred onto a hot plate and isopropanol (175 mL) was added portionwise to the hot solution, until the turbidity persisted upon heating. Water was then added dropwise until the solution was just clear at its boiling point. The conical flask was removed from the hot plate and allowed to cool to room temperature. A crystalline solid formed, which was collected by suction filtration, washed with minimum amount of isopropanol and dried for 30 min. The resultant white solid was dried under vacuum overnight at 70° C., yielding N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine dipotassium salt, (0.95 g, 1.44 mmol, 92%, 99% pure) $^1$H NMR (D$_2$O): δ7.68 (d, 1H, J=3.8 Hz), 7.49 (d, 1H, J=8.8 Hz), 6.87 (d, 1H, J=8.8 Hz), 6.51 (s, 2H), 5.52 (d, 1H, $J^3_{PH}$=2.0 Hz), 3.54 (s, 3H), 3.48 (s, 6H), 1.32 (s, 6H). $^{31}$P NMR (D$_2$O): 2.7

6. Preparation of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine di-L-Arginine Salt

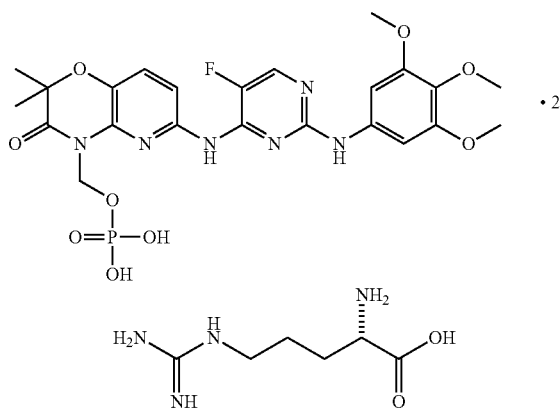

A suspension of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (0.25 g, 0.43 mmol) and L-arginine (0.15 g, 0.86 mmol) in EtOH (15 mL) was heated at 90° C. (oil bath temp) for 10 min. Water (7.5 mL) was added dropwise to the hot stirring suspension until it became a clear solution. After 1 h of heating with stirring, the hot solution was filtered into an Erlenmeyer flask. The filtrate in the Erlenmeyer flask was brought to boiling on a hot plate, the allowed to cool to room temperature. A solid formed, which was collected by gravity filtration and dried under vacuum overnight at 80° C. to form the subject prodrug salt hydrate (0.28 g, 0.3 mmol, 69%). $^1$H NMR (D$_2$O): δ7.64 (d, 1H, J=3.5 Hz), 7.42 (d, 1H, J=8.8 Hz), 6.80 (d, 1H, J=8.8 Hz), 6.45 (s, 2H), 5.53 (d, 1H, J$^3_{PH}$=2.8 Hz), 3.57 (t, 2H, J=6.0 Hz), 3.51 (s, 3H), 3.44 (s, 6H), 3.01 (t, 4H, J=6.5 Hz), 1.74-1.69 (m, 4H), 1.55-1.46 (m, 4H), 1.30 (s, 6H). $^{31}$P NMR (D$_2$O): 2.56.

7. Preparation of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine di-L-lysine Salt

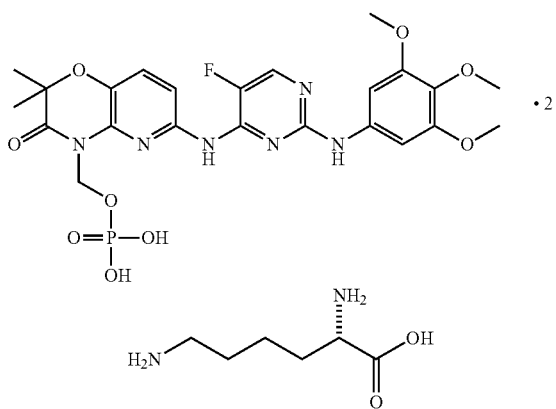

A suspension of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine (0.25 g, 0.43 mmol) and L-lysine (0.125 g, 0.86 mmol) in EtOH (15 mL) was heated at 90° C. (oil bath temp) for 10 min. Water (4.5 mL) was added dropwise to the hot stirring suspension until it formed a clear solution. After 1 h of heating and stirring, the reaction mixture filtered, cooled and concentrated under vacuum. Precipitation of the crude concentrate was observed upon addition of EtOH (5 mL). The resultant solid was stirred overnight at room temperature in t-BuOMe after concentration of the mixture. The white solid was collected by gravity filtration and dried under vacuum overnight at 80° C. (0.32 g, 83%). $^1$H NMR (D$_2$O): δ 7.67 (d, 1H, J=3.8 Hz), 7.47 (d, 1H, J=8.8 Hz), 6.84 (d, 1H, J=8.8 Hz), 6.48 (s, 2H), 5.54 (d, 1H, J$^3_{PH}$=3.5 Hz), 3.57 (t, 2H, J=6.0 Hz), 3.51 (s, 3H), 3.44 (s, 6H), 2.86 (t, 4H, J=6.7 Hz), 1.77-1.70 (m, 4H), 1.62-1.52 (app q, 4H, J 6.3 Hz), 1.38-1.26 (m, 10H). $^{31}$P NMR (D$_2$O): 2.59.

8. Synthesis of N4-(2, 2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine mono magnesium salt

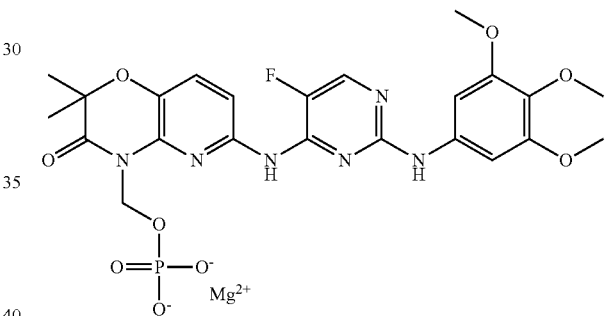

A suspension of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine dipotassium salt (0.5 g, 0.76 mmol) in 10 mL water was placed onto preheated oil bath at 80° C. and stirred till the suspension formed a clear solution. The hot solution was filtered, and the filter paper was washed with another 10 mL of water. The clear filtrate was heated while stirring at 80° C. MgCl$_2$ (0.076 g, 0.8 mmol) was dissolved in water (10 mL), filtered into a flask through a filter column (rinsing with 10 mL water), and heated at 90° C. (pH=7.52). The preheated dipotassium salt solution was added dropwise to the above MgCl$_2$ solution for 15 min while stirring the contents. The initial white frothing suspension formed slowly turned to clear white solid upon heating the contents at 80° C. for 1.5 h (pH=6.3-6.7). The solid was collected by suction filtration and washed with water until there was no chloride ion was detected (AgNO$_3$ test). The solid was suction dried for 2 h, then by vacuum dried at 70° C. overnight to provide N4-(2, 2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine mono magnesium salt (0.43 mg, 93%).

9. Synthesis of Prodrug Compound 8

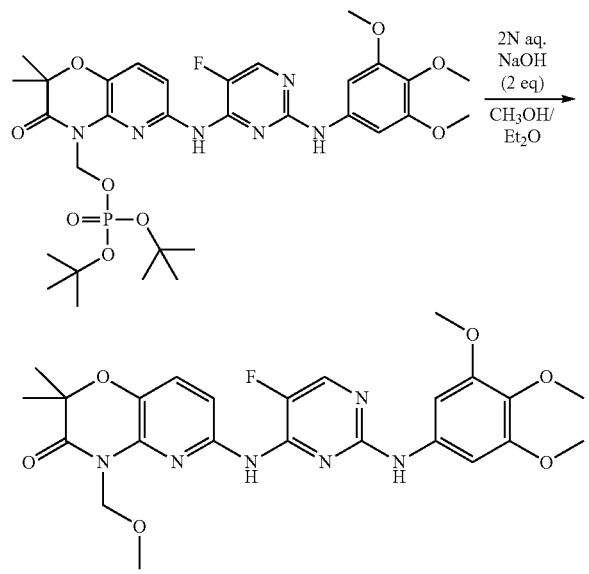

N4-(2,2-dimethyl-4-[(di-tert-butyl phosphonoxy)methyl]-3-oxo-5-pyrido[1,4]oxazin-6-yl)-5-fluoro-N2-(3,4,5-trimethoxyphenyl)-2,4-pyrimidinediamine (prepared as described above) (0.2 g, 0.29 mmol) was added to a mixture of MeOH(5 mL) and Et$_2$O (5 mL). 2N aq. NaOH (0.023 g, 0.58 mmol) was added at once while stirring the contents at room temperature. Progress of the reaction was monitored by LC/MS. After 8 h of stirring, the solid precipitated was filtered and dried to provide N4-(2,2-dimethyl-4-methoxymethyl-3-oxo-5-pyrido[1,4]oxazin-6-yl)-5-fluoro-N2-(3,4,5-trimethoxyphenyl)-2,4-pyrimidinediamine (Compound 8) as a white solid (0.11 g, 74%). $^1$H NMR (DMSO-d6): δ 9.47 (s, 1H), 9.15 (s, 1H), 8.16 (d, 1H, J=3.8 Hz), 7.87 (d, 1H, J=8.5 Hz), 7.37 (d, 1H, J=8.5 Hz), 7.03 (s, 2H), 5.40 (s, 2H), 3.66 (s, 6H), 3.59 (s, 3H), 3.27 (s, 3H), 1.44 (s, 6H). LCMS: ret. time: 12.88 min.; purity: 92%; MS (m/e): 515 (MH$^+$).

10. The Active 2,4-Pyrimidinediamine Compounds are Tolerated in Animals

The ability of numerous biologically active 2,4-pyrimidinediamine compounds to exert their activity at doses below those exhibiting toxicity in animals has been demonstrated previously (see, e.g., U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003 (US 2005/0028212), international application Serial No. PCT/US03/24087 (WO2004/014382), U.S. application Ser. No. 10/903,263 filed Jul. 30, 2004 (US2005/0234049), and international application Serial No. PCT/US2004/24716 (WO 2005/016893).

The safety pharmacology of active Compound 1 has been studied in a core battery of studies (respiratory, CNS, cardiovascular, and HERG). A slight reduction in heart rate and increase in RR interval was noted at 50 mg/kg in the cardiovascular study and a slight effect on a few behavioral parameters at 50 mg/kg was also noted in the CNS (Irwin) study. Otherwise the safety pharmacology studies determined that Compound 1 was well tolerated. GLP toxicology studies included negative mutagenicity and clastogenicity studies (Ames, chromosomal aberration, and mouse micronucleus). In 28-day toxicity studies in rats and monkeys, higher doses had evidence of a reversible effect on hematology, liver transaminase (mild effect in the rat only), spleen and thymus size (rat only) and bone marrow cellularity (rat and monkey). Immunophenotyping in the rat study revealed a significant decrease in the percentage of CD3+ cells in high dose rats while a significant increase in CD45RA+ cells was noted following recovery. Histopathology was noteworthy only for mild reductions in marrow cellularity at high doses. There was no evidence for untoward effects on humoral immunity in the anti-KLH antibody assessment. The No Observed Adverse Effect Level (NOAEL) is 10-30 mg/kg/day for rats and 100 mg/kg/day for monkeys.

11. Drug Compound 1 is Biologically Active in In Vitro Assays

Compound 1 blocks FcεRI-dependent activation of Cord-Blood Derived Primary Human Mast Cells (CHMC) in a dose-dependent manner with an EC$_{50}$ of approximately 43 nM as assessed by measuring the activity of tryptase released upon degranulation. Compound 1 does not inhibit ionomycin-induced degranulation of CHMCs. Ionomycin is a calcium ionophore that induces CHMC degranulation bypassing early FcR signaling, thus indicating that Compound 1 is specific to FcR signaling, and not degranulation per se. Compound 1 also inhibits the FcεRI-dependent production and release of LTC4 (EC$_{50}$=39 nM) and all cytokines tested (EC$_{50}$ ranging from 158 nM-462 nM).

12. Drug Compound 1 is Effective in Animal Models of Rheumatoid Arthritis

The biologic activity of Compound 1 in IC-mediated vascular edema (Arthus reaction in the rat), in collagen antibody-induced arthritis in the mouse, and in a rat model of collagen-induced arthritis.

12.1. Arthus Reaction

IC-mediated acute inflammatory tissue injury is implicated in a variety of human autoimmune diseases, including vasculitis, serum sickness, systemic lupus erythematosus, RA, and glomerulonephritis. The classical experimental model for IC-mediated tissue injury is the Reverse Passive Arthus (RPA) reaction. Intravenous injection of antigen (ovalbumin, OVA) following intradermal injection of antibodies specific to OVA (rabbit anti-OVA IgG) results in perivascular deposition of IC and a rapid inflammatory response characterized by edema, neutrophil infiltration, and hemorrhage at the injection sites (Szalai, et al., 2000, J. Immunol. 164(1):463-468).

A single oral treatment of rats with Compound 1 one hour prior to antigen/antibody administration reduced the cutaneous RPA reaction and inflammatory edema in a dose-dependent manner. Administration of 10 mg/kg oral Compound 1 inhibited extravascular leakage of Evans blue dye (OD$_{610}$) from tissue biopsies by 80% compared with vehicle control.

12.2. Collagen Antibody-Induced Arthritis

The anti-inflammatory activity of Compound 1 was evaluated in the mouse collagen antibody-induced arthritis (CAIA) model in which an anti-type II collagen antibody cocktail is applied to induce arthritis (Teroto et al., 1992, J. Immunol. 148(7):2103-2108; McCoy et al., 2002, J. Clin. Invest. 110 (5):651-658; Kagari et al., 2002, J. Immunol. 169(3):1459-1466). This passive model differs from the traditional rodent collagen-induced arthritis (CIA) in that disease symptoms appear quickly (developing within 24-48 hrs after an IV-injection of antibodies), arthritis is inducible in both CIA-susceptible and CIA-resistant mouse strains, and it allows evaluation of inflammation that is independent of antibody production.

CAIA was induced in Balb/c mice by intravenous injection of Arthrogen-CIA® Monoclonal Antibody Blend (Chemicon International, Inc., Temecula, Calif.) via the tail vein, followed 2 days later by an intraperitoneal injection of LPS. Oral Compound 1 treatment was started within 4 hours of antibody administration (Day 0). The severity of the arthritis in hind-paws was scored daily (scale of 0-4 per paw, sum of scores for both hind paws). By Day 5, both control groups, saline and vehicle, reached their peak clinical score with a disease incidence of 100%.

Reduced inflammation and swelling was evident in animals treated with Compound 1, and the arthritis progressed more slowly. Treatment with Compound 1 (b.i.d.) significantly reduced clinical arthritis ($p<0.05$) compared with animals treated with vehicle only, while lower dose levels of Compound 1 showed a trend toward reduced arthritis severity, disease incidence, and time of onset; however, the differences were not significant ($p>0.05$).

12.3. Collagen-Induced Arthritis

One of the experimental models for IC-mediated tissue injury is the CIA in rodents (Kleinau et al., 2000, J. Exp. Med. 191:1611-1616). Injection of type II collagen (CII) into rodents produces an immune reaction that characteristically involves inflammatory destruction of cartilage and bone of the distal joints with concomitant swelling of surrounding tissues. CIA in rats is commonly used to evaluate compounds that might be of potential use as drugs for treatment of rheumatoid arthritis and other chronic inflammatory conditions and is induced in susceptible strains of either mice or rats by injection of CII in incomplete Freund's adjuvant (IFA). Administration of this emulsion gives rise to polyarthritis, characterized by synovial hyperplasia, infiltration of mononuclear cells, pannus formation, and destruction of cartilage and bone. It has been previously well documented that antibodies to CII are a prerequisite for CIA in mice, as B-cell deficient mice do not develop arthritis (Svensson et al., 1998, Clin. Exp. Immunol. 111:521-526).

Syngeneic LOU rats were immunized on Day 0 with native chicken CII/IFA. Oral treatment began at the onset of arthritis symptoms (Day 10). A total of 59 rats were treated with either a vehicle control or Compound 1 at one of four dose levels (1, 3, 10, and 30 mg/kg, q.d. by p.o. gavage). Hind limbs were scored daily for clinical arthritis severity using a standardized method based on the degree of joint inflammation. High resolution digital radiographs of hind limbs were obtained at the conclusion of the study (Day 28). These limbs were also analyzed for histopathologic changes. IgG antibodies to native CII were measured in quadruplicate by ELISA. There was a significant reduction ($p<0.05$) in arthritis severity that was evident within 7 days after initiation of therapy in the high-dose (30 mg/kg) group that continued to improve throughout the study. By Day 28, the clinical score in the animals treated with vehicle alone was 6.08±0.67 compared to 2.54±0.98 in the Compound 1 30 mg/kg group ($p<0.001$). Blinded radiographs at study termination (Day 28), demonstrated a significant reduction in joint damage: 3.66±0.71 (vehicle) vs. 1.63±0.67 (Compound 1) ($p<0.02$) (E. Brahn. 2004). Blinded composite histopathologic studies confirmed the regression of pannus and erosions: Mean modified Mankin scores were 11.8±0.9 (vehicle) vs. 3.7±0.9 (30 mg/kg Compound 1) ($p<0.001$). Antibodies to native CII were not decreased in Compound 1-treated rats.

13. The Prodrug Compounds are Orally Bioavailable

Prodrug Compound 4 was tested for oral bioavailability. For the study, the prodrug was dissolved in various vehicles (e.g. PEG 400 solution and CMC suspension) for intravenous and oral dosing in the rats. Where indicated, the active metabolite Compound 1 compound (drug) was formulated and administered in the same vehicles. Following administration of the prodrug and/or drug, plasma samples were obtained and extracted. The plasma concentrations of the prodrug and/or drug were determined by high performance liquid chromatography/tandem mass spectrometry (LC/MS/MS) methods. Pharmacokinetic analyses were performed based on the plasma concentration data. The pharmacokinetic parameters of interest include Clearance (CL), Volume of distribution at steady-state (Vss), terminal half-life ($t_{1/2}$), and oral bioavailability (% F).

The results of these various pharmacokinetic experiments are illustrated in FIGS. 4-12.

Figure 4:
Figure 4:
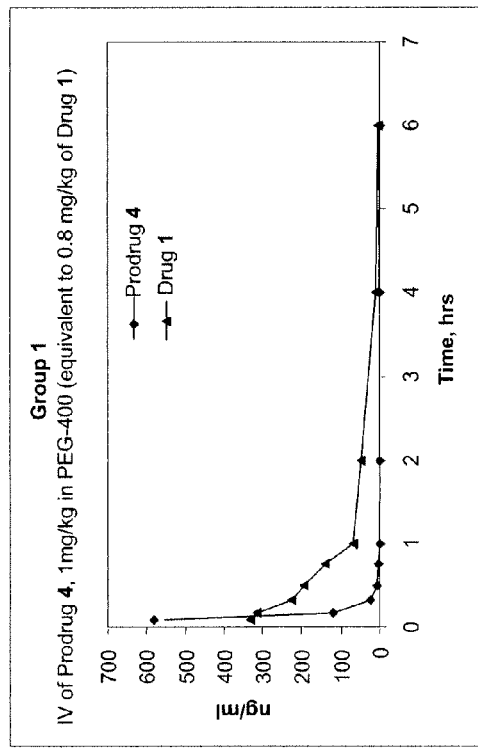

Referring to FIG. 4, PK profiles are shown for IV and PO administration in Sprague-Dawley rats. For IV administration, Compound 4 was dissolved in PEG-400 and administered at a dose of 1 mg/kg. Rapid disappearance of prodrug Compound 4 was observed and drug Compound 1 was found in plasma samples obtained from the jugular vein. Given orally in the same vehicle, no prodrug Compound 4 was present systemically, but high levels of drug metabolite Compound 1 were observed.

FIG. 5 summarizes the PK parameters for the study described in FIG. 4. Prodrug Compound 4 is rapidly cleared and, in part, converted to drug Compound 1. Given orally at a dose of 4 mg/kg, bioavailability was determined to be 29.9%. This bioavailability number is based on data obtained from a previous study (data not shown) in which drug Compound 1 was administered as an IV bolus dose at 1 mg/kg.

Figure 6:
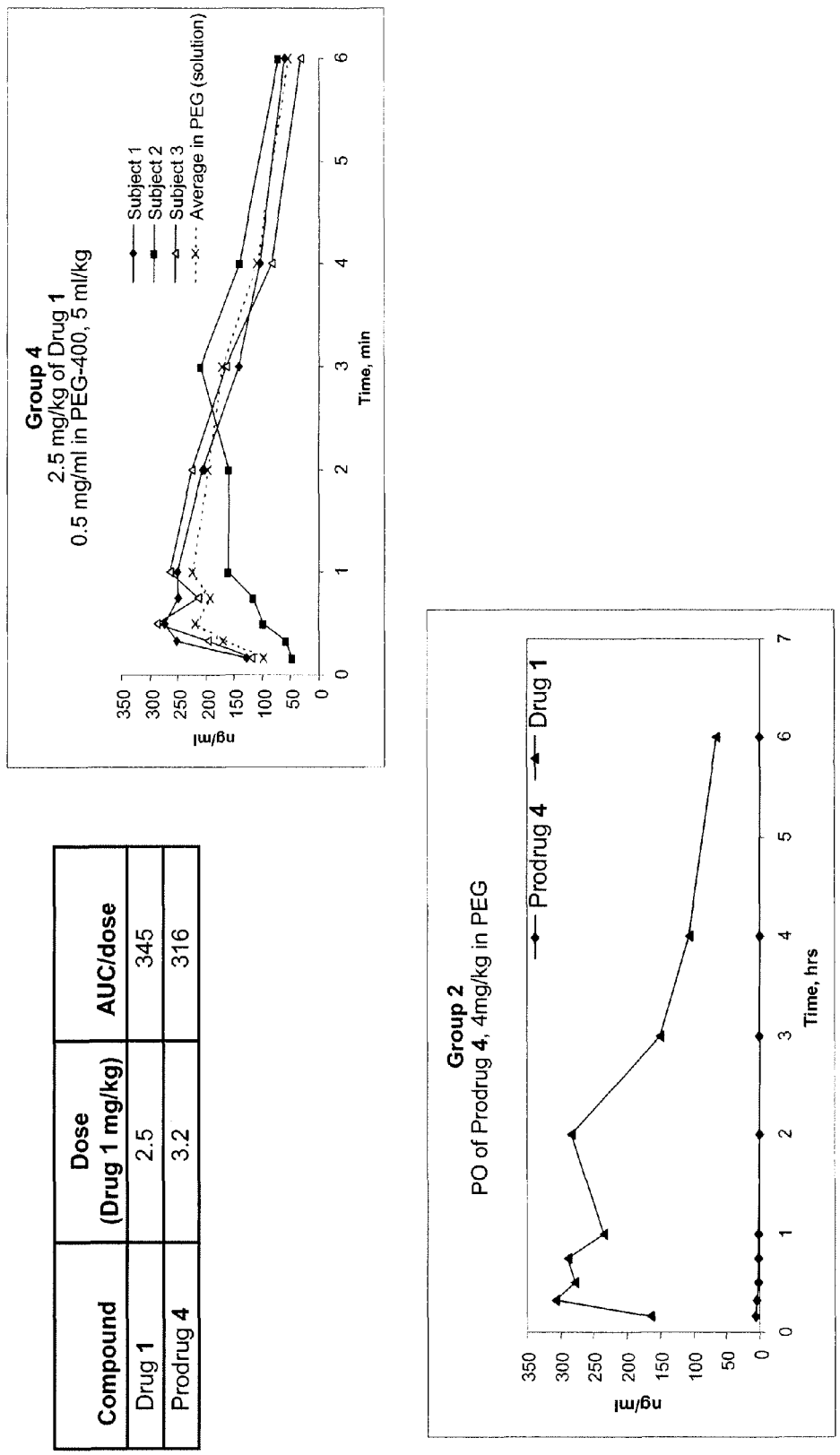

FIG. 6 compares drug Compound 1 exposure in Sprague-Dawley rats following oral administration of either drug Compound 1 (2.5 mg/kg in PEG-400) or prodrug Compound 4 (4 mg/kg in PEG-400). The values for AUC/dose are nearly identical indicating that the prodrug Compound 4 is absorbed equally as well as drug Compound 1.

Figure 7:
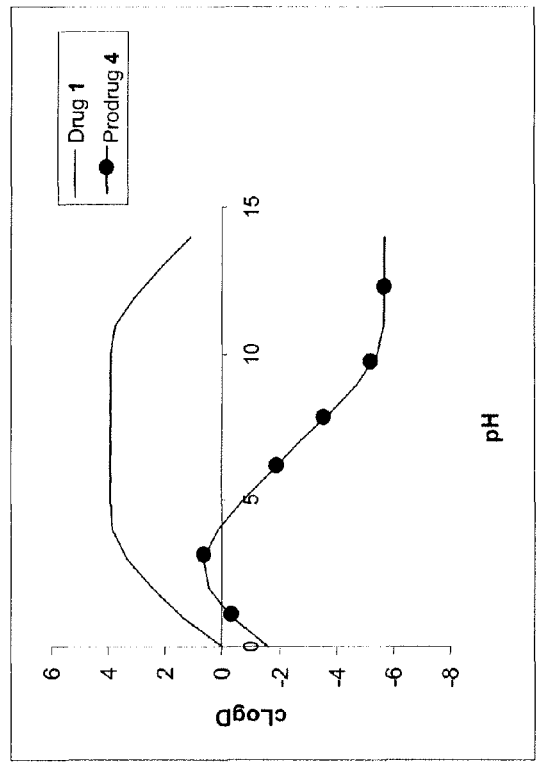

FIG. 7 shows a plot of cLogD vs pH calculated using in-situ predictions for both Compound 1 and Compound 4. Compound 1 is highly liphophyllic and only weakly ionizable (measured solubility is less than 1 mcg/ml in phosphate buffer at pH=7.5, data not shown). In contrast, Compound 4 is highly polar at neutral pH. Measured solubility values are consistent with the predicted cLogD values at pH=7.5.

Figure 8:
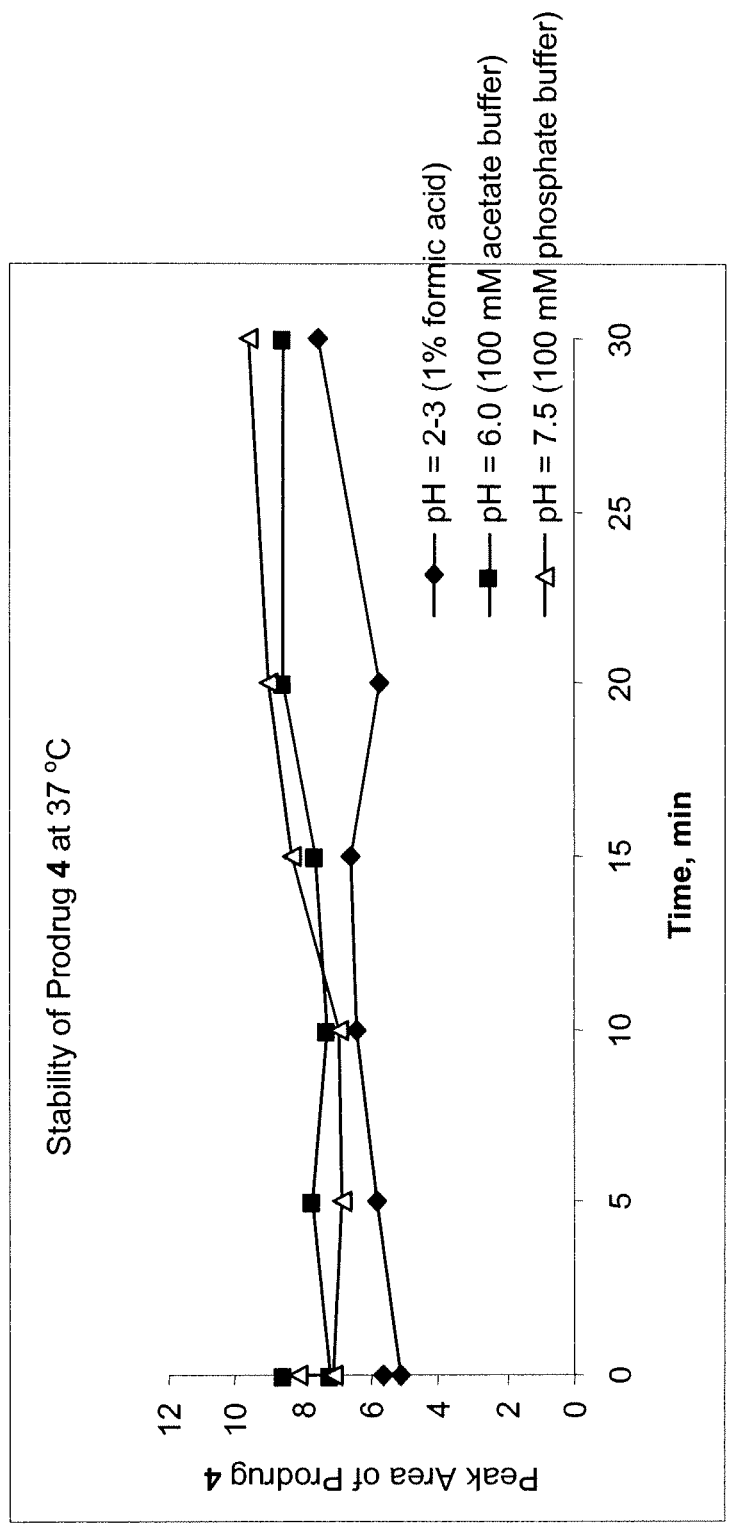

FIG. 8 demonstrates that prodrug Compound 4 is stable under acidic and neutral conditions at 37° C.

Figure 9:
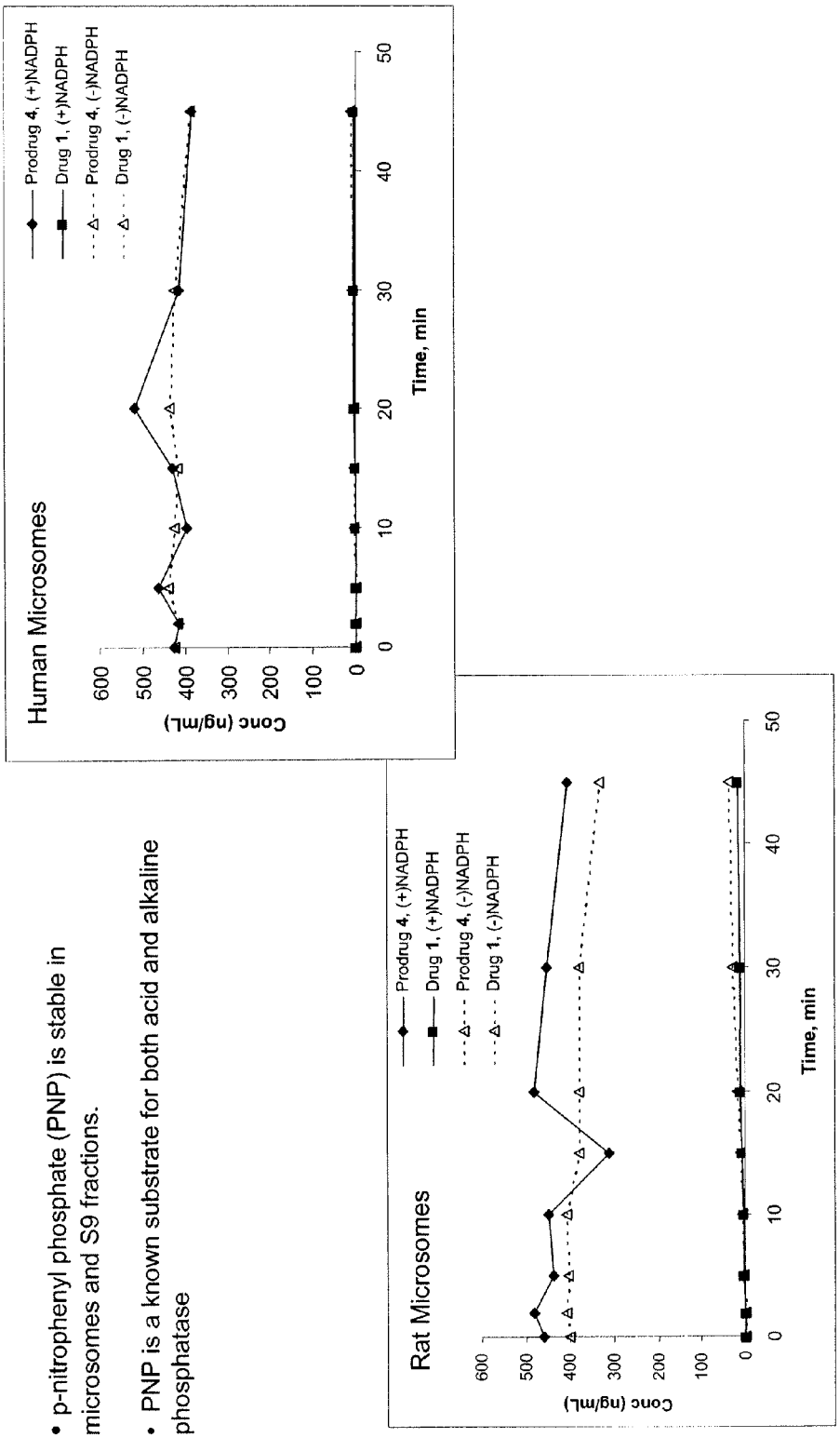

FIG. 9 illustrates the conversion of prodrug Compound 4 to drug Compound 1 in microsome preparations. Prodrug Compound 4 failed to convert to drug Compound 1 in microsomal preparations obtained from Xenotech. In follow-up studies using intestinal and hepatic microsomes obtained from a different source, conversion of Compound 4 to Compound 1 was observed (data not shown).

Figure 10:
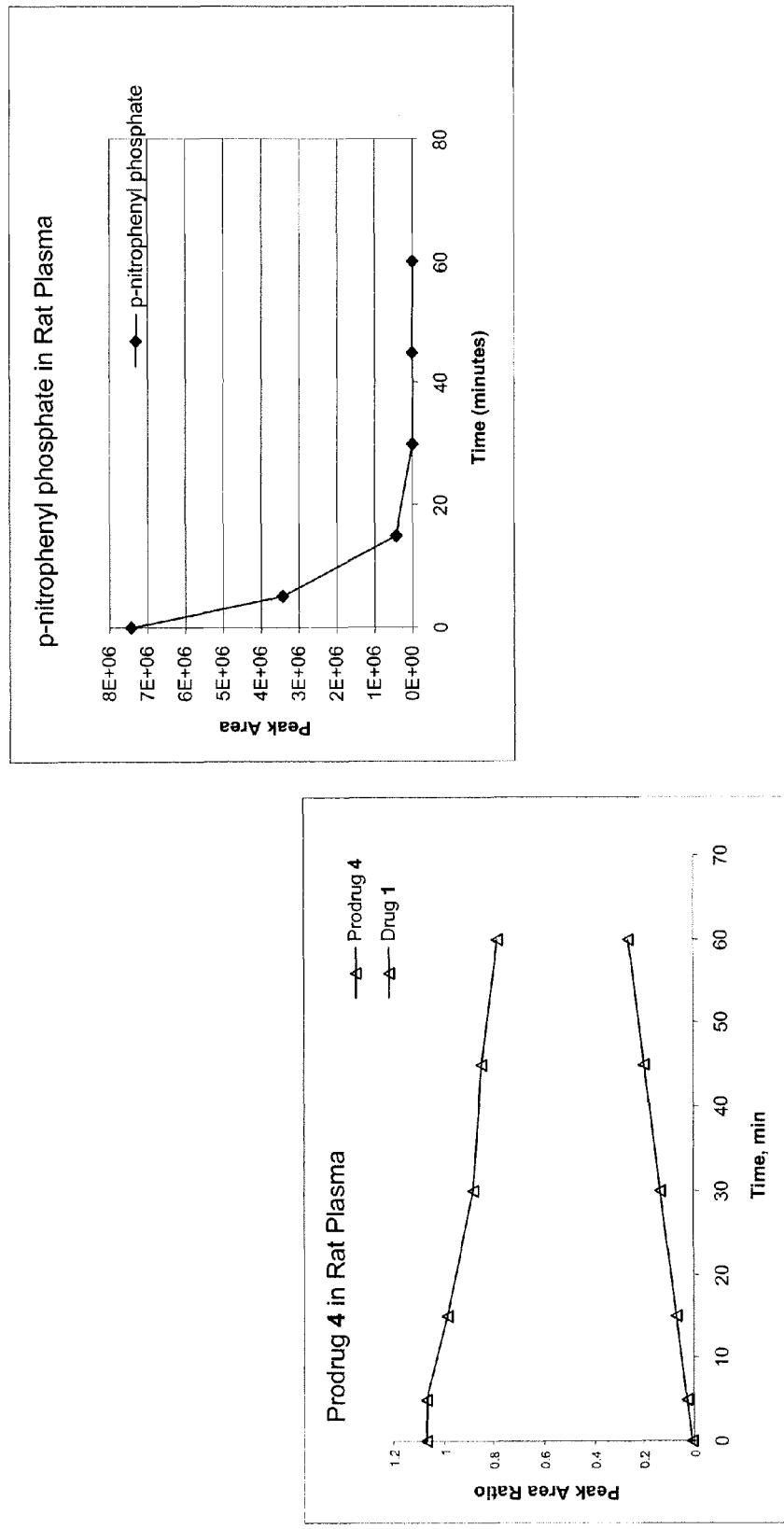

FIG. 10 illustrates that prodrug Compound 4 is unstable in rat plasma—hydrolysis to drug Compound 1 is observed and the conversion to Compound 1 is thought to be catalyzed by phosphatase enzymes. The presence of Phosphatase activity in rat plasma was confirmed using p-nitrophenyl phosphate—a known substrate for phosphatase.

Figure 11:
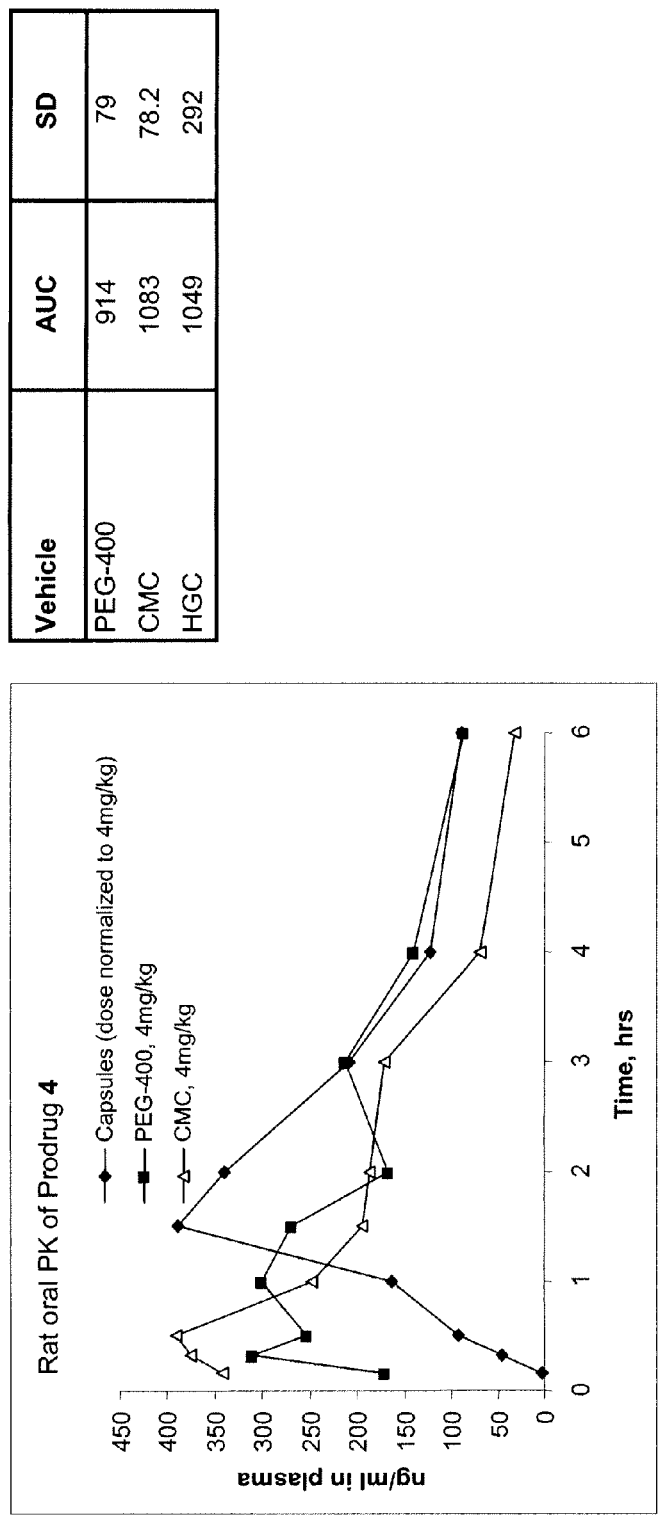

FIG. 11 illustrates the absorption of prodrug Compound 4 from different vehicles. Unlike drug Compound 1, absorption of prodrug Compound 4 is not dependent on formulation. Prodrug Compound 4 is absorbed equally well in solution formulations (PEG-400 and carboxymethylcellulose (CMC)) and as a powder in hard gelatin capsules.

Based on the pharmacokinetic data, the oral bioavailability (% F) of prodrug Compound 4 from all three vehicles tested (PEG-400 solution; CMC Solution; and powder in capsules) was determined to be approx. 30%.

14. Prodrug Salt Hydrates are Stable

Prodrug salt hydrate 32 was subjected to thermal analysis, moisture sorption analysis, and X-ray powder diffraction (XRPD) analysis to determine its stability and crystallinity.

Differential scanning calorimetry (DSC) thermograms were obtained using a DSC Q 100 (TA Instruments, New Castle, Del.). The temperature axis and cell constant of the DSC cell were calibrated with indium (10 mg, 99.9% pure, melting point 156.6° C., heat of fusion 28.4 J/g). Samples (2.0-5.0 mg) were weighed in aluminum pans on an analytical balance. Aluminum pans without lids were used for the analysis. The samples were equilibrated at 25° C. and heated to 250-300° C. at a heating rate of 10° C/min under continuous nitrogen flow. Thermogravimetric analysis (TGA) of the samples was performed with a Q 50 (TA Instruments, New Castle, Del.). Samples (2.0-5.0 mg) were analyzed in open aluminum pans under a nitrogen flow (50 mL/min) at 25° C. to 210° C. with a heating rate of 10° C/min.

The sample for moisture analysis was allowed to dry at 25° C. for up to 4 hours under a stream of dry nitrogen. The relative humidity was then increased stepwise from 10 to 90% relative humidity (adsorption scan) allowing the sample to equilibrate for a maximum of four hours before weighing and moving on to the next step. The desorption scan was measured from 85 to 0% relative humidity with the same equilibration time. The sample was then dried at 80° C. for 2 hours or until no weight loss was observed under a stream of dry nitrogen.

X-ray powder diffraction data were collected using a Miniflex Tabletop XRD system (Rigaku/MSC, The Woodlands, Tex.) from 5° to 45° 2θ with steps of 0.1°, and the measuring time was 1.0 second/step. All samples were ground to similar size before exposure to radiation. The powder samples were illuminated using CuKα radiation (λ=1.54056 Å) at 30 kV and 15 mA.

Variable temperature XRPD data were collected using a Huber Imaging Plate Guinier Camera 670 employing Ni-filtered CuKα$_1$ radiation (λ=1.5405981 Å) produced at 40 kV and 20 mA by a Philips PW1120/00 generator fitted with a Huber long fine-focus tube PW2273/20 and a Huber Guinier Monochromator Series 611/15. The original powder was packed into a Lindemann capillary (Hilgenberg, Germany) with an internal diameter of 1 mm and a wall thickness of 0.01 mm. The sample was heated at an average rate of 5 Kmin$^{-1}$ using a Huber High Temperature Controller HTC 9634 unit with the capillary rotation device 670.2. The temperature was held constant at selected intervals for 10 min while the sample was exposed to X-rays and multiple scans were recorded. A 2θ-range of 4.00-100.0° was used with a step size of 0.005° 2θ.

Figure 12:
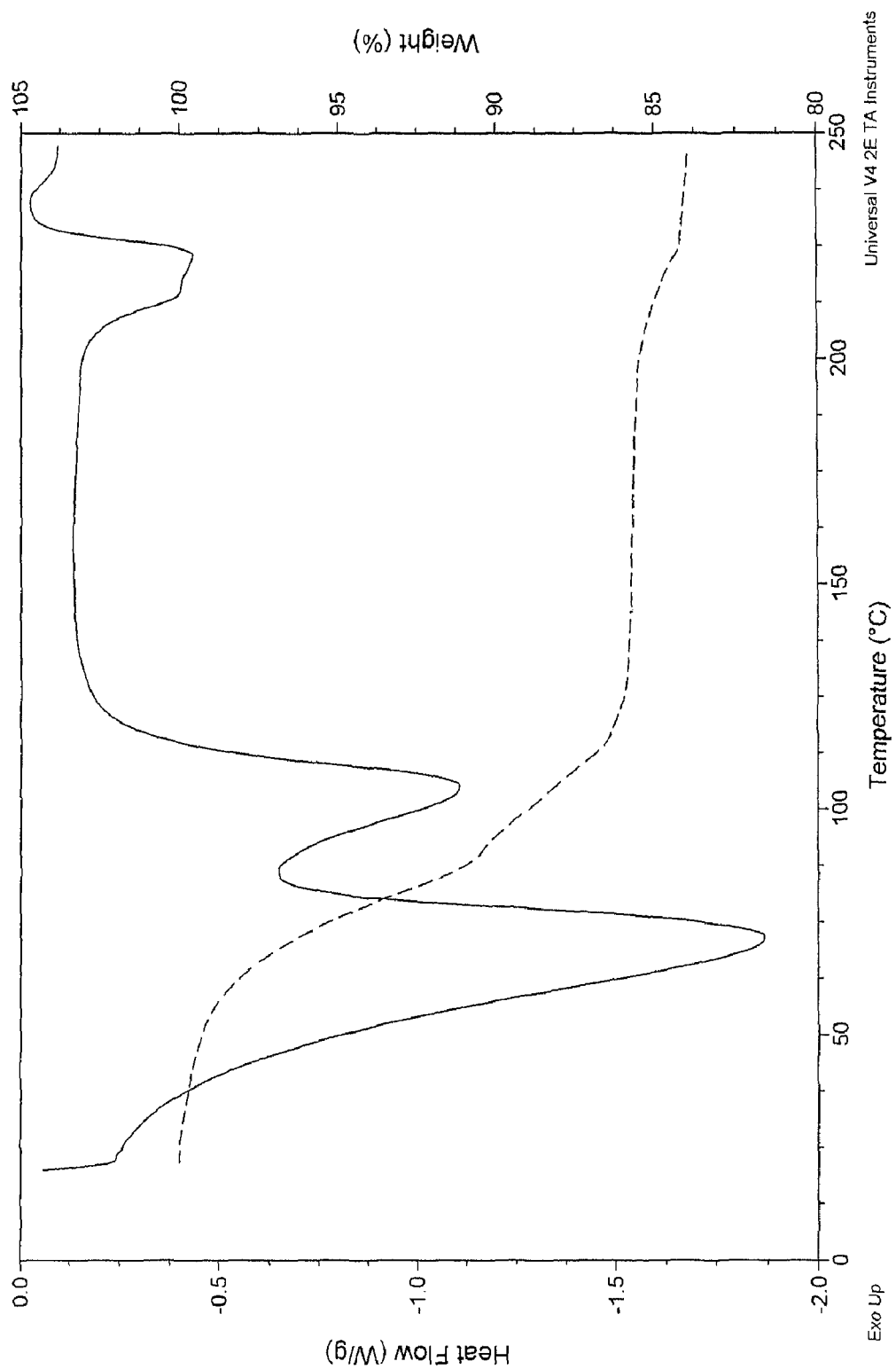
FIGS. 12-15 provide graphs illustrating various structural data for prodrug salt hydrate 32.

FIG. 12 presents the DSC and TGA thermograms of a sample of prodrug salt hydrate 32. The DSC thermogram reveals three endothermic transitions: an initial peak with an onset temperature of 42.98±2.01° C. and a peak temperature of 70.26±1.78° C., immediately followed by another endotherm with an onset of 90.33±3.21° C. and a peak at 106.19±2.89° C. The enthalpy value associated with the first transition is 209.70±12.34 J/g while the second transition requires about 67.24±4.56 J/g. In accordance with the DSC transitions, TGA analysis indicates three distinct stages of weight change. During the first step, the sample loses 9.64±0.18% of mass followed by a subtle change in slope leading to another weight loss of 5.13±0.11%. The sample thus loses a total of about 14.74±0.14% up to a temperature of 150° C. These results are in harmony with Karl Fisher titration data which indicates that the water content of the sample is approximately 14.82±0.17%, corresponding to 6 moles of water per mole of prodrug salt. Thus, the first two transitions in the thermal profile of prodrug salt 32 are due to dehydration of the sample. The final DSC transition starts at 206.54±4.63° C. with peak maxima at 223.35±2.27° C. and enthalpy of 35.26±5.44 J/g and is thought to be due to melting. The TGA indicates a weight loss during this transition, which is attributed to mass loss due to decomposition of the sample.

Figure 13:
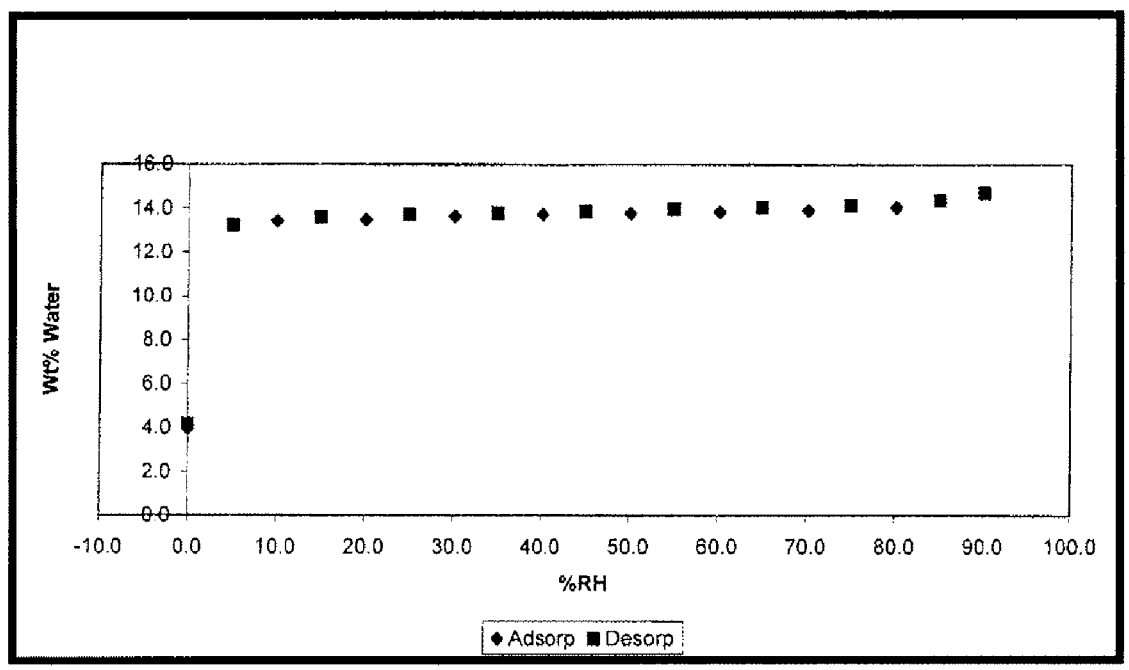

The moisture sorption profile of a sample of prodrug salt hydrate 32, shown in FIG. 13, demonstrates that the hexahydrate form is stable over a wide range of relative humidities. When the sample is dried at ambient temperature and about 0% relative humidity the sample tends to lose majority of its moisture content. As observed in the FIG. 13, the moisture content of the sample is approximately 4.0% under dry conditions. This indicates that approximately 4 water molecules per prodrug salt 32 are lost at this low humidity. However, as soon as the humidity is increased, the sample regains all of its water molecules and returns to approximately 14.0% water content. Notably, this shift from 4.0 to 14.0% water occurs in a very narrow range (0-10%) of relative humidities. Compared to the change occurring in this narrow humidity range, the change in moisture content over 10.0 to 95.0% relative humidity is relatively small.

While not intending to be bound to any particular explanation, the inventors surmise that this behavior can be explained by the behavior of an isomorphous solvate—desolvate system. At low humidity, the sample loses majority of the water molecules, yet retains the three dimensional order of the crystal lattice. The dehydrated, unrearranged lattice remains extremely hygroscopic, and resorbs water as soon as the humidity is increased. Once the water molecules have been regained, the lattice becomes stable, and no further change in hydration is observed.

Figure 14:
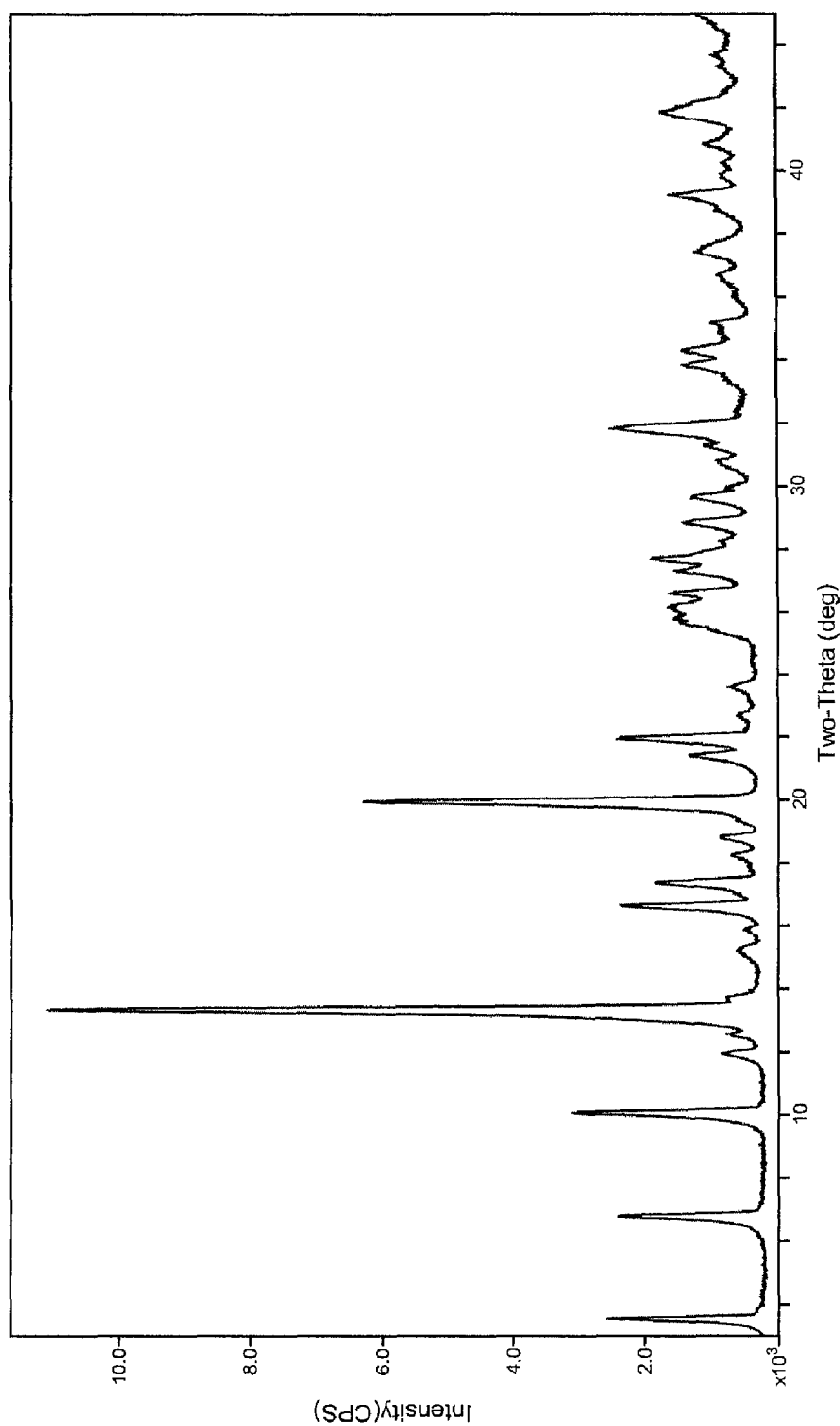

FIG. 14 presents the XRPD pattern of a sample of prodrug salt 32. As is evident from the pattern, the sample has a well defined crystal structure and a high degree of crystallinity. The XRPD data is summarized in Tables 1 and 2, below.

TABLE 1

Table 1. Peak Search Report (39 Peaks, Max P/N = 37.3)
X-ray Source

| | |
|---|---|
| Source | Cu |
| Filter | Ni |
| kV | 30 |
| mA | 15 |
| Kα (Å) | 1.54059 |
| scan | 3 to 45 |
| scan speed | 2.00/min |
| Method | continuous |
| Count | cps |

TABLE 2

Table 2. XRPD pattern of prodrug salt 32 (PEAK: 47-pts/Parabolic Filter, Threshold = 3.0, Cutoff = 0.1%, BG = 3/1.0, Peak – Top = Summit)

| 2-Theta | d(Å) | Height | H % | FWHM | XS(Å) |
|---|---|---|---|---|---|
| 3.380 | 26.1226 | 3315 | 56.7 | 0.198 | 3488 |
| 6.620 | 13.3412 | 1468 | 25.1 | 0.225 | 982 |
| 9.890 | 8.9360 | 1547 | 26.5 | 0.218 | 953 |
| 11.750 | 7.5252 | 1192 | 20.4 | 0.292 | 443 |
| 12.350 | 7.1610 | 813 | 13.9 | 0.268 | 517 |
| 13.150 | 6.7273 | 5846 | 100.0 | 0.362 | 305 |
| 13.510 | 6.5489 | 823 | 14.1 | 0.421 | 244 |
| 15.020 | 5.8938 | 423 | 7.2 | 0.343 | 326 |
| 15.710 | 5.6365 | 186 | 3.2 | 0.163 | 3043 |
| 16.421 | 5.3940 | 997 | 17.0 | 0.253 | 545 |
| 17.190 | 5.1543 | 1696 | 29.0 | 0.257 | 518 |
| 17.661 | 5.0177 | 113 | 1.9 | 0.110 | >5000 |
| 18.060 | 4.9079 | 206 | 3.5 | 0.216 | 743 |
| 18.600 | 4.7667 | 849 | 14.5 | 0.225 | 665 |
| 19.730 | 4.4960 | 2948 | 50.4 | 0.277 | 440 |
| 21.240 | 4.1797 | 1745 | 29.8 | 0.419 | 237 |
| 21.750 | 4.0828 | 1479 | 25.3 | 0.308 | 362 |
| 22.479 | 3.9521 | 100 | 1.7 | 0.138 | >5000 |
| 23.400 | 3.7985 | 458 | 7.8 | 0.323 | 334 |
| 24.237 | 3.6692 | 123 | 2.1 | 0.240 | 533 |
| 25.280 | 3.5201 | 1053 | 18.0 | 0.613 | 148 |
| 25.840 | 3.4451 | 1502 | 25.7 | 0.723 | 123 |
| 27.150 | 3.2818 | 1037 | 17.7 | 0.508 | 183 |
| 27.510 | 3.2397 | 1563 | 26.7 | 0.477 | 198 |
| 28.640 | 3.1143 | 644 | 11.0 | 0.269 | 423 |
| 29.470 | 3.0285 | 931 | 15.9 | 0.331 | 313 |
| 30.531 | 2.9256 | 308 | 5.3 | 0.262 | 436 |
| 31.640 | 2.8256 | 1761 | 30.1 | 0.412 | 235 |
| 33.650 | 2.6613 | 549 | 9.4 | 0.472 | 199 |
| 34.110 | 2.6264 | 670 | 11.5 | 0.603 | 150 |
| 34.990 | 2.5623 | 140 | 2.4 | 0.051 | >5000 |
| 36.379 | 2.4676 | 248 | 4.2 | 0.467 | 202 |
| 37.251 | 2.4119 | 494 | 8.5 | 0.393 | 248 |
| 38.540 | 2.3341 | 337 | 5.8 | 0.411 | 235 |
| 39.030 | 2.3059 | 519 | 8.9 | 0.582 | 157 |
| 39.631 | 2.2723 | 172 | 2.9 | 0.210 | 576 |
| 40.650 | 2.2177 | 306 | 5.2 | 0.198 | 634 |
| 41.640 | 2.1672 | 767 | 13.1 | 0.517 | 180 |
| 43.482 | 2.0796 | 155 | 2.6 | 0.531 | 175 |

Figure 15:
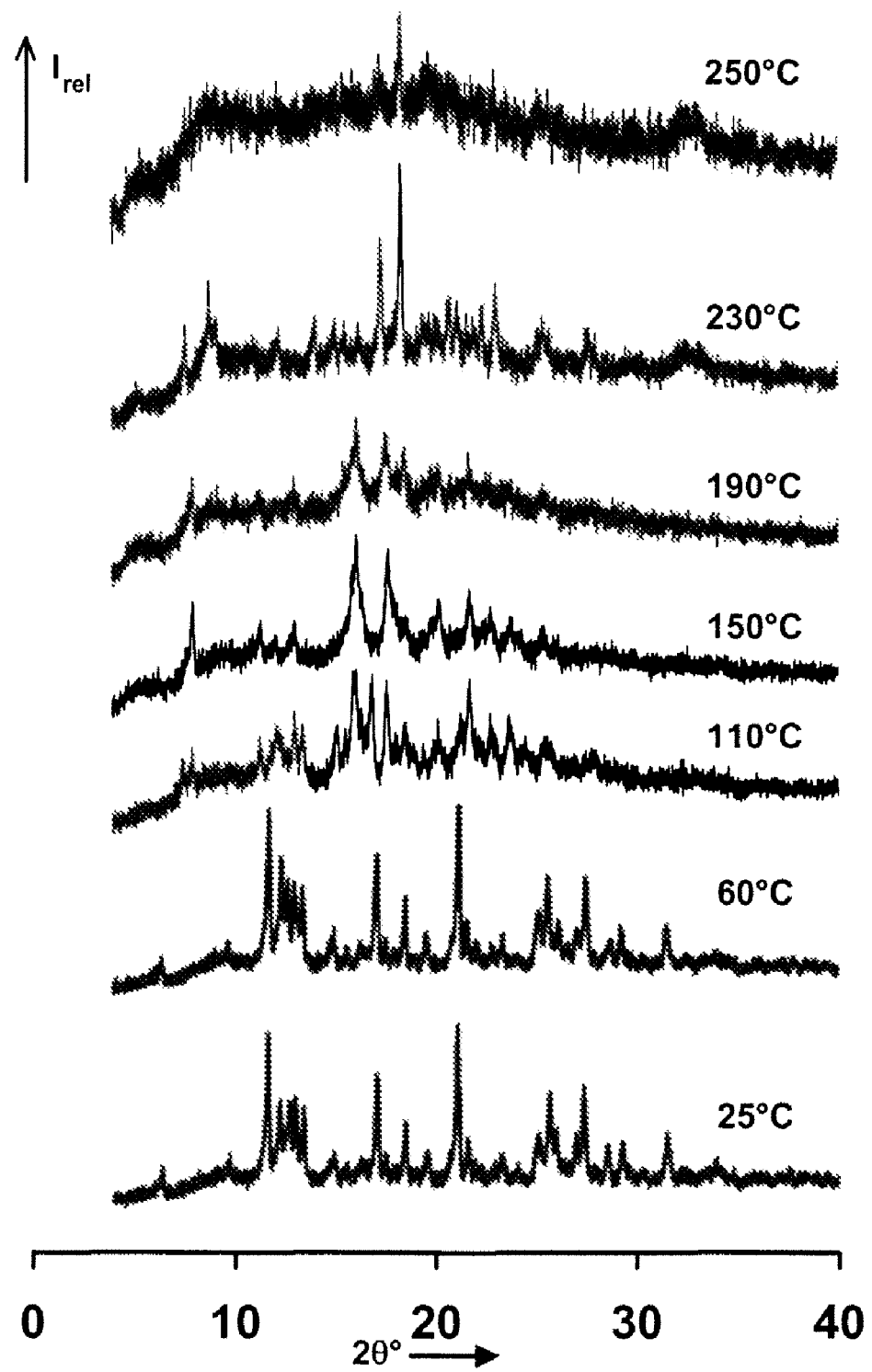

Variable temperature XRPD data, shown in FIG. 15, provides further evidence of the existence of an isomorphous solvate—desolvate system. As is evident in FIG. 15, the powder patterns obtained at 25° C. and 60° C. are substantially identical. From the thermal analysis described above, it is known that the sample starts dehydrating as early as 40° C. and peaks at around 70° C. to lose 4 of its 6 water molecules. The XRPD does not indicate any structural changes at 60° C., suggesting that the loss of water molecules does not change the three dimensional order of the crystal lattice. Structural changes in the sample are noted as the temperature rises to about 110° C. As the thermal data demonstrates, almost all of the water molecules are lost around this temperature. This suggests that once the all of the water molecules are lost, the crystal does undergo structural rearrangement. As suggested by the loss of peaks in the XRPD, as the temperature increases the crystal lattice collapses, and the material eventually decomposes.

Single crystal x-ray diffraction of prodrug salt hydrate 32 was performed, and indicated that the crystal of the invention contains substantially no methanol, and six molecules of water per prodrug molecule. The experimentally determined crystal unit cell parameters and data collection parameters for prodrug salt hydrate 32 are summarized in Table 3.

TABLE 3

Table 3. Single crystal x-ray diffraction data for prodrug salt hydrate 32.

| Crystal Data | |
|---|---|
| Formula | C23 H36 F N6 Na2 O15 P |
| Formula Weight | 732.53 |
| Crystal System | Monoclinic |
| Space Group | P2$_1$/c (No. 14) |
| a (Å) | 27.7282(5) |
| b (Å) | 7.9776(1) |
| c (Å) | 15.1739(3) |
| alpha (°) | 90 |
| beta (°) | 103.206(1) |
| gamma (°) | 90 |
| V(Å$^3$) | 3267.8(1) |
| Z | 4 |
| D (Calc) [g/cm$^3$] | 1.485 |
| μ (MoKalpha) [/mm] | 0.194 |
| F(000) | 1528 |
| Crystal size [mm] | 0.80 × 0.15 × 0.02 |
| Data collection | |
| Temperature (K) | 113 |
| Radiation (Å) | MoKalpha 0.71073 |
| Theta Min-Max [Deg} | 3.4, 27.8 |
| Dataset | −36: 36; −10: 10; −19: 19 |
| Tot., Uniq data, R (int.) | 26192, 7582, 0.089 |
| Obsxerved Data [I > 2.0 sigma(I)] | 4452 |
| Refinement | |
| Nref, Npar | 7582, 474 |
| R, wR2, S | 0.0514, 0.1312, 1.06 |
| w = 1/[\s^2^(Fo^2^) + (0.0587P)^2^ + 0.9541P] where P = (Fo^2^ + 2Fc^2^)/3 | |
| Max. and Av. Shift/Error | <0.001, <0.001 |
| Min. and Max. Resd. Dens. [e/Å$^3$] | −0.52, 1.27 |

The behavior of prodrug salt hydrate 32 indicates that it can be expected to have long-term stability upon storage. The hexahydrate form is stable over a wide range of relative humidities, and requires substantial heating (e.g. greater than 40° C.) to begin to lose included water molecules. High humidity does not affect the hexahydrate; extremely low humidity (i.e. less than 10% RH) can cause dehydration of the hexahydrate, but re-exposure to ambient conditions engenders reformation of the hexahydrate. The lack of observed structural changes under low humidity conditions, and heating up to 110° C., allows for water loss to be reversible the loss to be reversible upon cooling. Additionally, the prodrug salt hydrate 32 has increased solubility (10 mg/mL in water) with respect to the parent phosphate prodrug 4 and the calcium salt, prodrug salt 6 (15 μg/mL in water).

What is claimed is:

1. A crystal comprising the prodrug salt hydrate,

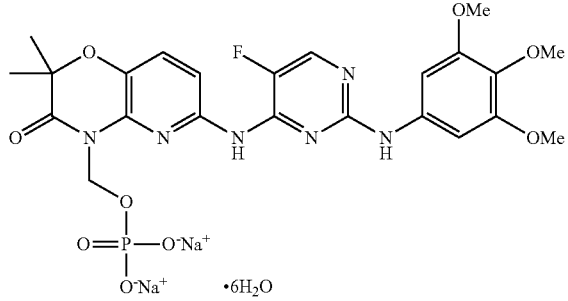

having characteristic powder X-ray diffraction peaks at two theta values of 3.4°±0.1°, 6.6°±0.1°, 9.9°±0.1°, 13.2°±0.1°, 17.2°±0.1°, 19.7°±0.1°, 21.2°±0.1°, and 21.8±0.1°.

2. A crystal comprising the prodrug salt hydrate,

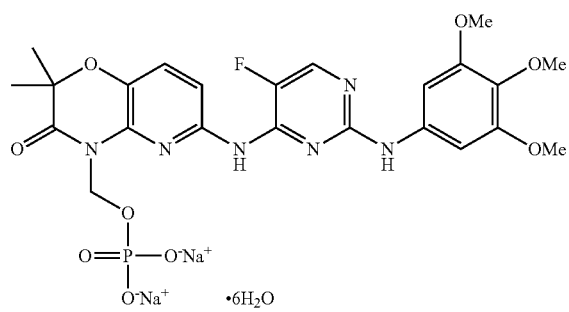

having space group symmetry P2₁/c and characteristic unit cell parameters of a=27.73 Å; b=7.98 Å; c=15.17 Å; alpha=90°; beta=103.2°; and gamma=90°.

3. A pharmaceutical composition comprising the prodrug salt hydrate according to claim 1 or 2 and a pharmaceutically-acceptable carrier, excipient and/or diluent.

4. A method of administering to a subject a 2,4-pyrimidinediamine compound, the method comprising administering to the subject the prodrug salt hydrate according to claim 1 or 2 or the pharmaceutical composition according to claim 3.

5. A method of inhibiting cell degranulation in a subject, comprising administering to the subject an amount of the prodrug salt hydrate according to claim 1 or 2 or the pharmaceutical composition according to claim 3, wherein the cell degranulation is associated with rheumatoid arthritis.

6. A method of inhibiting an activity of a Syk kinase in a subject, comprising administering to the subject an amount of the prodrug salt hydrate according to claim 1 or 2 or the pharmaceutical composition according to claim 3 effective to inhibit the Syk kinase activity.

7. A method of inhibiting an Fc receptor signal transduction cascade in a subject, comprising administering to the subject an amount of the prodrug salt hydrate according to claim 1 or 2 or the pharmaceutical composition according to claim 3 effective to inhibit the Fc receptor signal transduction cascade.

8. The method of claim 7 in which the Fc receptor is selected from the group consisting of FcαRI, FcγRI, FcγRIII and FcεRI.

9. A method of treating an autoimmune disease in a subject, and/or one or more symptoms associated therewith, comprising administering to the subject an amount of the prodrug salt hydrate according to claim 1 or 2 or the pharmaceutical composition according to claim 3 effective to treat the autoimmune disease, wherein the autoimmune disease is selected from the group consisting of Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis, membranous glomerulopathy, systemic lupus erythematosis, rheumatoid arthritis, Sjogren's syndrome, Reiter's syndrome, polymyositis-dermatomyositis, systemic sclerosis, polyarthritis nodosa, multiple sclerosis and bullous pemphigoid.

10. A method of treating rheumatoid arthritis in a subject, comprising administering to a subject suffering from rheumatoid arthritis an amount of the prodrug salt hydrate according to claim 1 or 2 or the pharmaceutical composition according to claim 3 effective to provide therapeutic benefit.

11. The method of claim 10 in which the amount of the prodrug salt hydrate administered is effective to achieve a serum concentration of the corresponding drug that is at or above the IC₅₀ of Syk inhibition of the drug, as measured in an in vitro assay.

12. A method for the preparation of the prodrug salt hydrate according to claim 1 or 2, the method comprising:
adjusting the pH of an aqueous solution of the prodrug

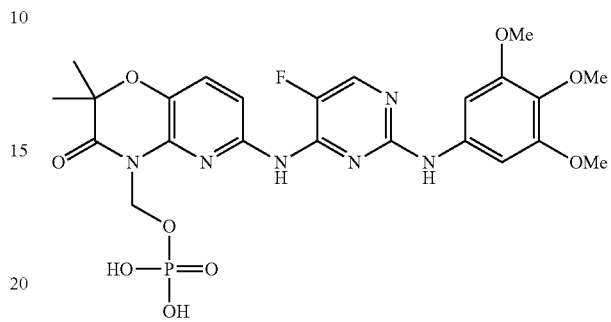

to a value in the range of about 8 to about 11 with a [Na⁺]-containing base; and
precipitating the prodrug salt hydrate from the aqueous solution.

13. The method of claim 12, in which the pH is adjusted to a value in the range of about 9 to 11.

14. The method of claim 13, in which the pH is adjusted to a value in the range of about 9.3 to about 10.5.

15. The method of claim 12, in which the [Na⁺]-containing base is NaOH, NaOMe, or Na₂CO₃.

16. The method of claim 12, in which the precipitating the prodrug salt hydrate from the solution comprises adding a water-miscible solvent to the aqueous solution.

17. The method of claim 16, in which the water-miscible solvent is selected from the group consisting of acetonitrile, acetone, isopropanol, methanol, ethanol, and mixtures thereof.

18. The method of claim 16, in which the aqueous solution is heated before adding the water miscible solvent, after adding the water miscible solvent, or both before and after adding the water miscible solvent, then allowed to cool to precipitate the prodrug salt hydrate.

19. The method of claim 12, further comprising isolating the prodrug salt hydrate from the aqueous solution.

20. A method for the preparation of a crystalline form of the prodrug salt hydrate according to claim 1 or 2, the method comprising:
(a) adjusting the pH of an aqueous solution of the prodrug

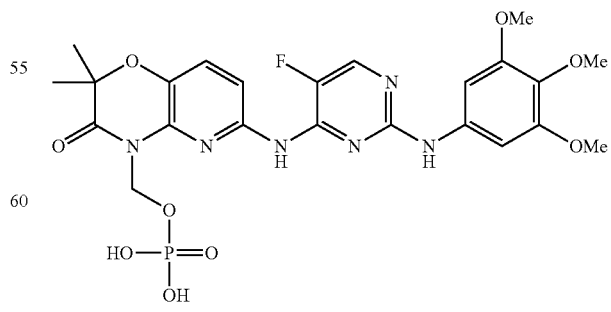

to a value in the range of about 9 to about 11 with a [Na⁺]-containing base;

(b) precipitating a prodrug salt hydrate from the aqueous solution; and
(c) exposing the prodrug salt to moisture, yielding the crystalline form of the prodrug salt hydrate.

21. The method according to claim 20 further comprising:
(i) prior to (b),
  1) adding a water-miscible solvent to the aqueous solution, and
  2) heating the aqueous solution, before adding the water miscible solvent, after adding the water-miscible solvent, or before and after adding the water-miscible solvent;
(ii) performing (b) via cooling the aqueous solution; and
(iii) prior to (c), 1) washing the prodrug salt hydrate with a wash solvent, and 2) removing substantially all of the wash solvent.

22. The crystal of claim 1 wherein the X-ray diffraction peaks are generated in response to radiation of wavelength 1.54059 Å.

* * * * *